US010988775B2

(12) United States Patent
Gao et al.

(10) Patent No.: US 10,988,775 B2
(45) Date of Patent: Apr. 27, 2021

(54) WHEAT PLANTS RESISTANT TO POWDERY MILDEW

(71) Applicant: Institute of Genetics and Developmental Biology Chinese Academy of Sciences, Beijing (CN)

(72) Inventors: Caixia Gao, Beijing (CN); Jin-Long Qiu, Beijing (CN); Yanpeng Wang, Beijing (CN)

(73) Assignee: INSTITUTE OF GENETICS AND DEVELOPMENTAL BIOLOGY CHINESE ACADEMY OF SCIENCES, Beijing (CN)

(*) Notice: Subject to any disclaimer, the term of this patent is extended or adjusted under 35 U.S.C. 154(b) by 22 days.

(21) Appl. No.: 15/745,479

(22) PCT Filed: Jul. 15, 2016

(86) PCT No.: PCT/GB2016/052149
§ 371 (c)(1),
(2) Date: Jan. 17, 2018

(87) PCT Pub. No.: WO2017/013409
PCT Pub. Date: Jan. 26, 2017

(65) Prior Publication Data
US 2018/0208939 A1 Jul. 26, 2018

(30) Foreign Application Priority Data
Jul. 17, 2015 (WO) ................ PCT/CN2015/084370

(51) Int. Cl.
*A01H 1/00* (2006.01)
*A01H 5/10* (2018.01)
*C12N 15/82* (2006.01)
*A01H 6/46* (2018.01)

(52) U.S. Cl.
CPC ........... *C12N 15/8282* (2013.01); *A01H 1/00* (2013.01); *A01H 5/10* (2013.01); *A01H 6/4678* (2018.05); *C12N 2310/20* (2017.05)

(58) Field of Classification Search
None
See application file for complete search history.

(56) References Cited

FOREIGN PATENT DOCUMENTS

WO  WO2014062989 A2  4/2014
WO  WO2015109752 A1  7/2015

OTHER PUBLICATIONS

Piffanelli et al., "A barley cultivation-associated polymorphism conveys resistance to powdery mildew", Nature, Aug. 19, 2004, pp. 887-891, vol. 430.
Elliott et al., "Functional Conservation of Wheat and Rice Mlo Orthologs in Defense Modulation to the Powdery Mildew Fungus", Molecular Plant-Microbe Interactions, Jan. 1, 2002, pp. 1069-1077, vol. 15, No. 10.
Wang et al., "Simultaneous editing of three homoeoalleles in hexaploid bread wheat confers heritable resistance to powdery mildew", Nature Biotechnology, Jul. 20, 2014, pp. 947-951, vol. 32, No. 9.
Varallyay et al., "Virus-induced gene silencing of Mlo genes induces powdery mildew resistance in Triticum aestivum", Official Journal of the Virology Division of the International Union of Microbiological Societies, Mar. 24, 2012, pp. 1345-1350, vol. 157, No. 7.

*Primary Examiner* — Phuong T Bui
(74) *Attorney, Agent, or Firm* — Greer, Burns & Crain, Ltd.

(57) ABSTRACT

In one aspect, this disclosure relates to a wheat plant, plant part or plant cell that has increased resistance to powdery mildew, wherein said plant comprises a loss of function mutation in the coding regions of two alleles selected from TaMLO-A1, TaMLO-B1 and TaMLO-D1 and reduced expression of the third TaMLO allele. In another aspect, this disclosure provides a method for producing a wheat plant, plant part or plant cell with increased resistance to powdery mildew, wherein the method comprises using targeted genome modification comprising introducing a loss of function mutation into the coding regions of two MLO alleles selected from TaMLO-A1, TaMLO-B1 and TaMLO-D1 and decreasing expression of the third TaMLO allele.

12 Claims, 14 Drawing Sheets
Specification includes a Sequence Listing.

Figure 5

TCGCTGCTGCTGGCCGTGACGGCAGGACCCATCTCCGGGATATGCATCTCCGAaagcttgtcgacggatccatggtgagcaaggggcgaggagctgtt
caccgggtggtgcccatcctgtgtcgagctgagctgagcggcgacgtgaacggccacaagttcagcgtgtccggcgaggggcgatgccacctacggc
aagctgaccctgaagttcatctgcaccaccggcaagctgcccgtgccctgcctgaccacctcgtgaccaccttcacctacggcgtgcagtgcttcagcc
gctaccccgaccacatgaagcagcacgacttcttcaagtcggccatgccggaggcgcaccatctcttcttcaaggacgacggcaa
ctacaagaccccgaggcgcggtgaagttcgagggcgacaccctggtgaaccgcatcgagctgaagggcatcgactttaaggaggacggcaacatcctg
gggcacaagctggagtacaactacaacagccacaacgtctatatcatggccgacaagcagaagaacggcatcaaggtgaacttcaagatccgccaca
acattgaggacggcagcgtgcagctgcccgaccacctaccagcagaacaccccatcggcgaccccgctgctgcccgacaactactacctgag
cacccagtccgctgagcaagtaaccaccagtcactgtcctgcactgagcgcctgagttcgtgaccgccgcggatcactcacggcatggac
gagctgtacaagtaaccggcgagctgcaagagccccaacggccaaactcgcgtgaccctctctctctattctctactctctatctaaatgtgtg
agtagtttcccgataaggggaatttaggttcgctctattggtttcgtcatgtgttggagcatataagaaacccatagtatgttgtatttgtaaaat
acttctataataaaatttctaattccttaaaaccaaaatccagtactactaaatcagctctcctaaagtcctatagatctttgtcgtgaataaaac
cagacacgagacgactaaactggagcccgacgcccgttcgaagctagaagtaccgcttaggcaggagcgcgttaggaaggagatgctaaggcaggg
ttggttacgttgactccccgtaggttggtttaaatgatgaagtggacggaaggaaggagaacaaggaaggttgcaggccctgtg
caaggtaagaagatggaaatttgatagagtgtaccgctactatacgctaaggaatgcttgtatttataccctaccccctaataac
cccttatcaatttaagaaaaataatccgataggctattcagagccatgaatagctctagcatcaaaactcaaagaggatgtaaaa
cctcaccaaaatcgaaggagttcttaactcaaaagatcttcaagataaaagatcttttcaagtacccaccggtgacgggatcgcatgcga
ttCGCTGCTGCTCGGCCGTGACGCAGGACCCATCTCCGGGATATGCATCTCCGA

SEQ ID NO. 49

Figure 6A-1 tcgtgccctctctagagataatgagcattgcatgtctaagttataaaaattaccacatatttttttgtc
acacttgtttgaagtgcagtttatctatctttatacatatatttaaactttactctacgaataatataatct
atagtactacaataatatcagtgttttagagaatcatataaatgaacagttagacatggtctaaaggacaat
tgagtattttgacaacaggactctacagttttatcttttagtgtgcatgtgttctcctttttttttgcaaa
tagcttcacctatataatacttcatccatttattagtacatccatttagggtttagggttaatggttttta
tagactaatttttttagtacatctatttattctatttagcctctaaattaagaaaactaaaactctattt
tagttttttatttaataatttagatataaaatagaataaaataaagtgactaaaaattaaacaaataccct
ttaagaaattaaaaaaactaaggaaacatttttcttgtttcgagtagataatgccagcctgttaaacgccgt
cgacgagtctaacggacaccaaccagcgaaccagcagcgtcgcgtcgggccaagcgaagcagacggcacggc
atctctgtcgctgcctctggaccctctcgatcgagagttccgctccaccgttggacttgctccgctgtcgg
catccagaaattgcgtggcggagcggcagacgtgagccggcacggcaggcggcctcctcctcctcacggc
accggcagctacgggggattcctttcccaccgctccttcgctttcccttcctcgccgccgtaataaataga
caccccctccacacctctttccccaacctcgtgttgttcggagcgcacacacacacaaccagatctcccc
aaatccacccgtcggcacctccgcttcaaggtacgccgctcgtcctcccccccccccctctctaccttctc
tagatcggcgttccggtccatggttagggcccggtagttctacttctgttcatgtttgtgttagatccgtgt
ttgtgttagatccgtgctgctagcgttcgtacacggatgcgacctgtacgtcagacacgttctgattgctaa
cttgccagtgtttctctttggggaatcctgggatggctctagccgttccgcagacgggatcgatttcatgat
tttttttgtttcgttgcatagggtttggtttgccctttcctttatttcaatatatgccgtgcacttgtttg
tcgggtcatcttttcatgctttttttgtcttggttgtgatgatgtggtctggttgggcggtcgttctagat
cggagtagaattaattctgtttcaaactacctggtggatttattaattttggatctgtatgtgtgtgccata
catattcatagttacgaattgaagatgatggatggaaatatcgatctaggataggtatacatgttgatgcgg
gttttactgatgcatatacagagatgcttttgttcgcttggttgtgatgatgtggtgtggttgggcggtcg
ttcattcgttctagatcggagtagaatactgtttcaaactacctggtgtatttattaattttggaactgtat
gtgtgtgtcatacatcttcatagttacgagtttaagatggatggaaatatcgatctaggataggtatacatg
ttgatgtgggttttactgatgcatatacatgatggcatatgcagcatctattcatatgctctaaccttgagt
acctatctattataataaacaagtatgttttataattattttgatcttgatatacttggatgatggcatatg
cagcagctatatgtggattttttagccctgccttcatacgctatttatttgcttggtactgtttctttttgt
cgatgctcaccctgttgtttggtgttacttctgcaaaagcttgccaagctatcaaacaagtttgtacaaaaa

Figure 6A-2 agctgaacgagaaacgtaaaatgatataaatatcaatatattaaattagattttgcataaaaaacagactac
ataatactgtaaaacacaacatatccagtcactatggcggccgcattaggcaccccaggctttacactttat
gcttccggctcgtataatgtgtggattttgagttaggatccggcgagatttcaggagctaaggaagctaaa
atggagaaaaaatcactggatataccaccgttgatatatcccaatggcatcgtaaagaacattttgaggca
tttcagtcagttgctcaatgtacctataaccagaccgttcagctggatattacggcctttttaaagaccgta
aagaaaaataagcacaagttttatccggcctttattcacattcttgcccgcctgatgaatgctcatccggaa
ttccgtatggcaatgaaagacggtgagctggtgatatgggatagtgttcacccttgttacaccgttttccat
gagcaaactgaaacgttttcatcgctctggagtgaataccacgacgatttccggcagtttctacacatatat
tcgcaagatgtggcgtgttacggtgaaaacctggcctatttccctaaagggtttattgagaatatgttttc
gtctcagccaatccctgggtgagtttcaccagttttgatttaaacgtggccaatatggacaacttcttcgcc
cccgttttcaccatgggcaaatattatacgcaaggcgacaaggtgctgatgccgctggcgattcaggttcat
catgccgtctgtgatggcttccatgtcggcagaatgcttaatgaattacaacagtactgcgatgagtggcag
ggcggggcgtaatctagaggatccggcttactaaaagccagataacagtatgcgtatttgcgcgctgatttt
tgcggtataagaatatatactgatatgtatacccgaagtatgtcaaaaagaggtgtgctatgaagcagcgta
ttacagtgacagttgacagcgacagctatcagttgctcaaggcatatatgatgtcaatatctccggtctggt
aagcacaaccatgcagaatgaagcccgtcgtctgcgtgccgaacgctggaaagcggaaaatcaggaagggat
ggctgaggtcgcccggtttattgaaatgaacggctcttttgctgacgagaacagggactggtgaaatgcagt
ttaaggtttacacctataaaagagagagccgttatcgtctgtttgtggatgtacagagtgatattattgaca
cgcccgggcgacggatggtgatcccctggccagtgcacgtctgctgtcagataaagtctcccgtgaactt
acccggtggtgcatatcggggatgaaagctggcgcatgatgaccaccgatatggccagtgtgccggtctccg
ttatcggggaagaagtggctgatctcagccaccgcgaaaatgacatcaaaaacgccattaacctgatgttct
ggggaatataaatgtcaggctcccttatacacagccagtctgcaggtcgaccatagtgactggatatgttgt
gttttacagtattatgtagtctgttttttatgcaaaatctaatttaatatattgatatttatatcatttac
gtttctcgttcagctttcttgtacaaagtggttcgataattccttaattaactagttctagagcggccgcc
accgcggtggagctcgaatttccccgatcgttcaaacatttggcaataaagtttcttaagattgaatcctg
ttgccggtcttgcgatgattatcatataatttctgttgaattacgttaagcatgtaataattaacatgtaa
tgcatgacgttatttatgagatgggtttttatgattagagtcccgcaattatacatttaatacgcgataga
aaacaaaatatagcgcgcaaactaggataaattatcgcgcgcggtgtcatctatgttact

Figure 6B tctagaATGgtggatctacgcacgctcggctacagtcagcagcagcaagagaagatcaaaccgaaggtgcgt
tcgacagtggcgcagcaccacgaggcactggtgggccatgggtttacacacgcgcacatcgttgcgctcagc
caacacccggcagcgttagggaccgtcgctgtcacgtatcagcacataatcacggcgttgccagaggcgaca
cacgaagacatcgttggcgtcggcaaacagtggtccggcgcacgcgccctggaggccttgctcacggatgcg
ggggagttgagaggtccgccgttacagttggacacaggccaacttgtgaagattgcaaaacgtggcggcgtg
accgcaatggaggcagtgcatgcatcgcgcaatgcactgacgggtgccccctgAACCTGACCCCGGACCA
AGTGGTGGCTATCGCCAGCCACGATGGCGGCAAGCAAGCGCTCGAAACGGTGCAGCGGCTGTTGCCGGTGC
TGTGCCAGGACCATGGCCTGACCCCGGACCAAGTGGTGGCTATCGCCAGCAACAATGGCGGCAAGCAAGCG
CTCGAAACGGTGCAGCGGCTGTTGCCGGTGCTGTGCCAGGACCATGGCCTGACTCCGGACCAAGTGGTGGC
TATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCAAGCAAGCGCTCGAAACG
GTGCAGCGGCTGTTGCCGGTGCTGTGCCAGGACCATGGCCTGACCCCGGACCAAGTGGTGGCTATCGCCAG
CAACAATGGCGGCAAGCAAGCGCTCGAAACGGTGCAGCGGCTGTTGCCGGTGCTGTGCCAGGACCATGGCC
TGACTCCGGACCAAGTGGTGGCTATCGCCAGCCACGATGGCGGCAAGCAAGCGCTCGAAACGGTGCAGCGG
CTGTTGCCGGTGCTGTGCCAGGACCATGGCCTGACCCCGGACCAAGTGGTGGCTATCGCCAGCAACGGTGG
CGGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACAATGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTGG
TGGCTATCGCCAGCAACGGTGGCGGCAAGCAAGCGCTCGAAACGGTGCAGCGGCTGTTGCCGGTGCTGTGC
CAGGACCATGGCCTGACCCCGGACCAAGTGGTGGCTATCGCCAGCCACGATGGCGGCAAGCAAGCGCTCGA
AACGGTGCAGCGGCTGTTGCCGGTGCTGTGCCAGGACCATGGCCTGACCCCGGACCAAGTGGTGGCTATCG
CCAGCAACAATGGCGGCAAGCAAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTGTGCCAGGACCATGGCCTGACC
CCGGACCAAGTGGTGGCTATCGCCAGCAACAATGGCGGCAAGCAAGCGCTCGAAACGGTGCAGCGGCTGTT
GCCGGTGCTGTGCCAGGACCATGGCCTGACCCCGGACCAAGTGGTGGCTATCGCCAGCAACGGTGGCGGCA
AGCAAGCGCTCGAAAGCATTGTGCCCAGCTGAGCCGGCCTGATCCGGCGTTGGCCGCGTTGAcccaacgac
cacctcgtcgccttggcctgcctcggcggacgtcctgccatggatgcagtgaaaaagggattgccgcacgcg
ccggaattgatcagaagagtcaatcgccgtattggcgaacgcacgtcccatcgcgttgccggatcc

Figure 6C-1 tctagaATGgtggatctacgcacgctcggctacagtcagcagcagcaagagaagatcaaaccgaaggtgcgt
tcgacagtggcgcagcaccacgaggcactggtgggccatgggtttacacacgcgcacatcgttgcgctcagc
caacaccggcagcgttagggaccgtcgctgtcacgtatcagcacataatcacggcgttgccagaggcgaca
cacgaagacatcgttggcgtcggcaaacagtggtccggcgcacgcgccctggaggccttgctcacggatgcg
ggggagttgagaggtccgccgttacagttggacacaggccaacttgtgaagattgcaaaacgtggcggcgtg
accgcaatggaggcagtgcatgcatcgcgcaatgcactgacgggtgccccctgAACCTGACCCCGGACCA
AGTGGTGGCTATCGCCAGCAACAAGGGCGGCAAGCAAGCGCTCGAAACGGTGCAGCGGCTGTTGCCGGTGC
TGTGCCAGGACCATGGCCTGACCCCGGACCAAGTGGTGGCTATCGCCAGCAACAAGGGCGGCAAGCAAGCG
CTCGAAACGGTGCAGCGGCTGTTGCCGGTGCTGTGCCAGGACCATGGCCTGACCCCGGACCAAGTGGTGGC
TATCGCCAGCAACAAGGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAACG
GTGCAGCGGCTGTTGCCGGTGCTGTGCCAGGACCATGGCCTGACCCCGGACCAAGTGGTGGCTATCGCCAG
CAACAAGGGCGGCAAGCAAGCGCTCGAAACGGTGCAGCGGCTGTTGCCGGTGCTGTGCCAGGACCATGGCC
TGACCCCGGACCAAGTGGTGGCTATCGCCAGCAACATTGGCGGCAAGCAAGCGCTCGAAACGGTGCAGCGG
CTGTTGCCGGTGCTGTGCCAGGACCATGGCCTGACCCCGGACCAAGTGGTGGCTATCGCCAGCAACGGTGG
CGGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACAAGGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTGG
TGGCTATCGCCAGCAACATTGGCGGCAAGCAAGCGCTCGAAACGGTGCAGCGGCTGTTGCCGGTGCTGTGC
CAGGACCATGGCCTGACCCCGGACCAAGTGGTGGCTATCGCCAGCAACGGTGGCGGCAAGCAAGCGCTCGA
AACGGTGCAGCGGCTGTTGCCGGTGCTGTGCCAGGACCATGGCCTGACCCCGGACCAAGTGGTGGCTATCG
CCAGCAACATTGGCGGCAAGCAAGCGCTCGAAACGGTGCAGCGGCTGTTGCCGGTGCTGTGCCAGGACCAT

Figure 6C-2

GGCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTGTGCCAGGACCATGGCCTGACT
CCGGACCAAGTGGTGGCTATCGCCAGCCACGATGGCGGCAAGCAAGCGCTCGAAACGGTGCAGCGGCTGTT
GCCGGTGCTGTGCCAGGACCATGGCCTGACTCCGGACCAAGTGGTGGCTATCGCCAGCCACGATGGCGGCA
AGCAAGCGCTCGAAACGGTGCAGCGGCTGTTGCCGGTGCTGTGCCAGGACCATGGCCTGACCCCGGACCAA
GTGGTGGCTATCGCCAGCAACAAGGGCGGCAAGCAAGCGCTCGAAAGCATTGTGGCCCAGCTGAGCCGGCC
TGATCGGCGTTGGCCGCGTTGAccaacgaccacctcgtcgccttggcctgcctcggcggacgtcctgcca
tggatgcagtgaaaaagggattgccgcacgcgccggaattgatcagaagagtcaatcgccgtattggcgaac
gcacgtccatcgcgttgccggatcc

Figure 6D-1

*Caaataatgattttattttgactgatagtgacctgttcgttgcaacaaattgatgagcaatgctttttata
atgccaactttgtacaaaaaagcaggctccgaattcgccctt*caccatggattataaggatcacgatggcga
ctacaaggaccacgatattgactacaaagacgatgacgataaaatggctcctaagaaaaagcgcaaagtcgg
tatccatggcgttccctctagaATGgtggatctacgcacgctcggctacagtcagcagcagcaagagaagat
caaaccgaaggtgcgttcgacagtggcgcagcaccacgaggcactggtgggccatgggtttacacacgcgca
catcgttgcgctcagccaacacccggcagcgttagggaccgtcgctgtcacgtatcagcacataatcacggc
gttgccagaggcgacacacgaagacatcgttggcgtcggcaaacagtggtccggcgcacgcgccctggaggc
cttgctcacggatgcgggggagttgagaggtccgccgttacagttggacacaggccaacttgtgaagattgc
aaaacgtggcggcgtgaccgcaatggaggcagtgcatgcatcgcgcaatgcactgacgggtgcccCCCTGAA
CCTGACCCCGGACCAAGTGGTGGCTATCGCCAGCCACGATGGCGGCAAGCAAGCGCTCGAAACGGTGCAGC
GGCTGTTGCCGGTGCTGTGCCAGGACCATGGCCTGACCCCGGACCAAGTGGTGGCTATCGCCAGCAACAAT
GGCGGCAAGCAAGCGCTCGAAACGGTGCAGCGGCTGTTGCCGGTGCTGTGCCAGGACCATGGCCTGACTCC
GGACCAAGTGGTGGCTATCGCCAGCCACGATGGCGGCAAGCAAGCGCTCGAAACGGTGCAGCGGCTGTTGC
CGGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAGT
GGTGGCTATCGCCAGCAACAATGGCGGCAAGCAAGCGCTCGAAACGGTGCAGCGGCTGTTGCCGGTGCTGT

Figure 6D-2

```
GCCAGGACCATGGCCTGACTCCGGACCAAGTGGTGGCTATCGCCAGCCACGATGGCGGCAAGCAAGCGCTC
GAAACGGTGCAGCGGCTGTTGCCGGTGCTGTGCCAGGACCATGGCCTGACCCCGGACCAAGTGGTGGCTAT
CGCCAGCAACGGTGGCGGCAAGCAAGCGCTCGAAACGGTGCAGCGGCTGTTGCCGGTGCTGTGCCAGGACC
ATGGCCTGACCCCGGACCAAGTGGTGGCTATCGCCAGCAACAATGGCGGCAAGCAAGCGCTCGAAACGGTG
CAGCGGCTGTTGCCGGTGCTGTGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACGGTGGCGGCAAGCAAGCGCTCGAAACGGTGCAGCGGCTG
TTGCCGGTGCTGTGCCAGGACCATGGCCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGACC
AAGTGGTGGCTATCGCCAGCAACAATGGCGGCAAGCAAGCGCTCGAAACGGTGCAGCGGCTGTTGCCGGTG
CTGTGCCAGGACCATGGCCTGACTCCGGACCAAGTGGTGGCTATCGCCAGCCACGATGGCGGCAAGCAAGC
GCTCGAAACGGTGCAGCGGCTGTTGCCGGTGCTGTGCCAGGACCATGGCCTGACTCCGGACCAAGTGGTGG
CTATCGCCAGCCACGATGGCGGCAAGCAAGCGCTCGAAACGGTGCAGCGGCTGTTGCCGGTGCTGTGCCAG
GACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCCA
GCAACGGTGGCGGCAAGCAAGCGCTCGAAAGCATTGTGGCCCAGCTGAGCCGGCCTGATCCGGCGTTGGCC
GCGTTGAccaacgaccacctcgtcgccttggcctgcctcggcggacgtcctgccatggatgcagtgaaaaa
gggattgccgcacgcgccggaattgatcagaagagtcaatcgccgtattggcgaacgcacgtcccatcgcg
ttgccggatccCagctggtgaagtccgagctggaagaaaaaaagagcgagctgcgccacaagctcaagtac
gtgccccacgagtacatcgagctgatcgagatcgcccgcaacagcacccaagaccgcatcctggagatgaa
agtgatggagttcttcatgaaggtgtacggctaccgcggcaagcacctgggcggctcccgcaagcccgatg
gcgccatctacaccgtgggctcccccatcgactatggcgtcattgtcgacaccaaggcctactccggcggc
tacaacttacccatcggtcaggccgacgagatgcaacgctacgtgaaggagaaccagacccgcaataagca
cattaatcccaacgagtggtggaaggtgtaccctcctccgtgaccgagttcaaattcctgttcgtgtccg
gccacttcaagggcaattataaggcccaactgacccgcctgaaccacaagaccaactgcaacggcgccgtg
ctgtccgtggaggaactgctgatcggcggcgagatgatcaaggctggtaccctgaccctggaagaggtgcg
ccgcaagttcaacaatggtgaaatcaatttcaggtccggcggcggaGagggcagaggaagtcttctaacat
gcggtgacgtggaggagaatcccggccctaggatggactacaaagaccatgacggtgattataaagatcat
gacatcgattacaaggatgacgatgacaagatggcccccaagaagaagaggaaggtgggcattcacggggt
```

Figure 6D-3 gccggctagcATGgtggatctacgcacgctcggctacagtcagcagcagcaagagaagatcaaaccgaagg
tgcgttcgacagtggcgcagcaccacgaggcactggtgggccatgggtttacacacgcgcacatcgttgcg
ctcagccaacacccggcagcgttagggaccgtcgctgtcacgtatcagcacataatcacggcgttgccaga
ggcgacacacgaagacatcgttggcgtcggcaaacagtggtccggcgcacgcgccctggaggccttgctca
cggatgcgggggagttgagaggtccgccgttacagttggacacaggccaacttgtgaagattgcaaaacgt
ggcggcgtgaccgcaatggaggcagtgcatgcatcgcgcaatgcactgacgggtgcccCCCTGAACCTGAC
CCCGGACCAAGTGGTGGCTATCGCCAGCAACAAGGGCGGCAAGCAAGCGCTCGAAACGGTGCAGCGGCTGT
TGCCGGTGCTGTGCCAGGACCATGGCCTGACCCCGGACCAAGTGGTGGCTATCGCCAGCAACAAGGGCGGC
AAGCAAGCGCTCGAAACGGTGCAGCGGCTGTTGCCGGTGCTGTGCCAGGACCATGGCCTGACCCCGGACCA
AGTGGTGGCTATCGCCAGCAACAAGGGCGGCAAGCAAGCGCTCGAAACGGTGCAGCGGCTGTTGCCGGTGC
TGTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGGC
TATCGCCAGCAACAAGGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAACG
GTGCAGCGGCTGTTGCCGGTGCTGTGCCAGGACCATGGCCTGACCCCGGACCAAGTGGTGGCTATCGCCAG
CAACGGTGGCGGCAAGCAAGCGCTCGAAACGGTGCAGCGGCTGTTGCCGGTGCTGTGCCAGGACCATGGCC
TGACCCCGGACCAAGTGGTGGCTATCGCCAGCAACAAGGGCGGCAAGCAAGCGCTCGAAACGGTGCAGCGG
CTGTTGCCGGTGCTGTGCCAGGACCATGGCCTGACTCCGGACCAAGTGGTGGCTATCGCCAGCCACGATGG
CGGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCCG
GTGCTGTGCCAGGACCATGGCCTGACCCCGGACCAAGTGGTGGCTATCGCCAGCAACGGTGGCGGCAAGCA
AGCGCTCGAAACGGTGCAGCGGCTGTTGCCGGTGCTGTGCCAGGACCATGGCCTGACCCCGGACCAAGTGG
TGGCTATCGCCAGCAACATTGGCGGCAAGCAAGCGCTCGAAACGGTGCAGCGGCTGTTGCCGGTGCTGTGC
CAGGACCATGGCCTGACCCCGGACCAAGTGGTGGCTATCGCCAGCAACGGTGGCGGCAAGCAAGCGCTCGA
AACGGTGCAGCGGCTGTTGCCGGTGCTGTGCCAGGACCATGGCCTGACTCCGGACCAAGTGGTGGCTATCG
CCAGCCACGATGGCGGCAAGCAAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTGTGCCAGGACCATGGCCTGACC

Figure 6D-4

CCGGACCAAGTGGTGGCTATCGCCAGCAACAAGGGCGGCAAGCAAGCGCTCGAAAGCATTGTGGCCCAGCT
GAGCCGGCCTGATCCGGCGTTGGCCGCGTTGAccaacgaccacctcgtcgccttggcctgcctcggcggac
gtcctgccatggatgcagtgaaaaagggattgccgcacgcgccggaattgatcagaagagtcaatcgccgt
attggcgaacgcacgtcccatcgcgttgccAgatctcaactagtcaaaagtgaactggaggagaagaaatc
tgaacttcgtcataaattgaaatatgtgcctcatgaatatattgaattaattgaaattgccagaaattcca
ctcaggatagaattcttgaaatgaaggtaatggaattttttatgaaagtttatggatatagaggtaaacat
ttgggtggatcaaggaaaccggacggagcaatttatactgtcggatctcctattgattacggtgtgatcgt
ggatactaaagcttatagcggaggttataatctgccaattggccaagcagatgaaatggagcgatatgtcg
aagaaaatcaaacacgaaacaaacatctcaaccctaatgaatggtggaaagtctatccatcttctgtaacg
gaatttaagttttatttgtgagtggtcactttaaaggaaactacaaagctcagcttacacgattaaatca
tatcactaattgtaatggagctgttcttagtgtagaagagcttttaattggtggagaaatgattaaagccg
gcacattaaccttagaggaagtgagacggaaatttaataacggcgagataaactttTAATAG aagggcgaattcgacccagctttcttgtacaaagttggcattataaaaaataattgctcatcaatttgttgc
aacgaacaggtcactatcagtcaaaataaaatcattatttg

Figure 7

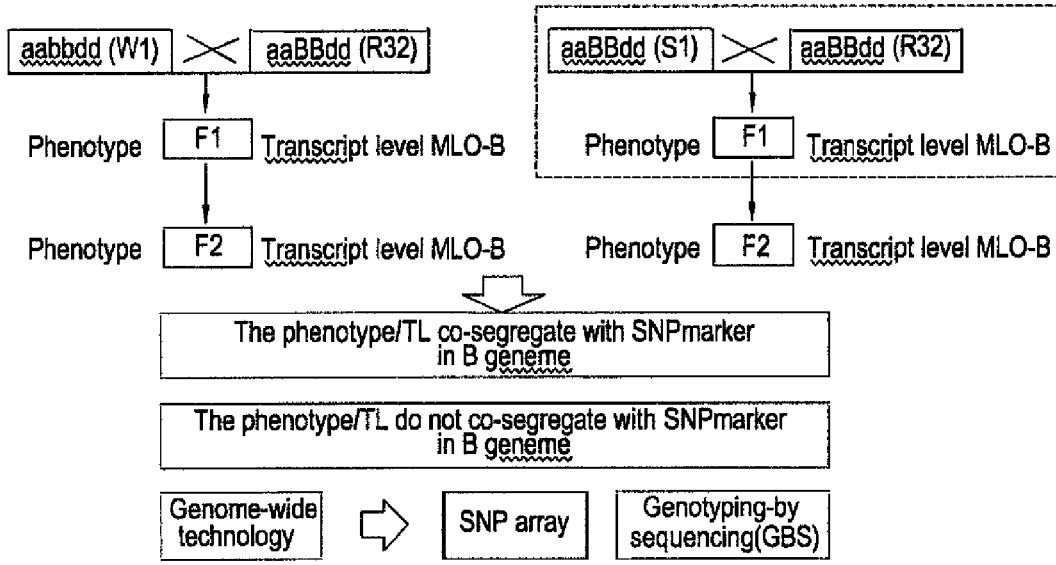

SEQUENCE LISTING

<160> NUMBER OF SEQ ID NOS: 51

<210> SEQ ID NO 1
<211> LENGTH: 1605
<212> TYPE: DNA
<213> ORGANISM: Triticum aestivum

<400> SEQUENCE: 1

```
atggcggagg acgacgggta ccccccggcg cggacgctgc cggagacgcc gtcctgggcg    60
gtggcgctgg tcttcgccgt catgatcatc gtctccgtcc tcctggagca cgcgctccac   120
aagctcggcc agtggttcca caagcggcac aagaacgcgc tggcggaggc gctggagaag   180
atgaaggcgg agctgatgct ggtgggattc atctcgctgc tgctcgccgt cacgcaggac   240
ccaatctccg ggatatgcat ctcccagaag gccgccagca tcatgcgccc ctgcaaggtg   300
gaacccggtt ccgtcaagag caagtacaag gactactact gcgccaaaga gggcaaggtg   360
gcgctcatgt ccacgggcag cctgcaccag ctccacatat tcatcttcgt gctagccgtc   420
ttccatgtca cctacagcgt catcatcatg gctctaagcc gtctcaagat gagaacatgg   480
aagaaatggg agacagagac cgcctccttg gaataccagt tcgcaaatga tcctgcgcgg   540
ttccgcttca cgcaccagac gtcgttcgtg aagcggcacc tgggcctgtc cagcaccccc   600
ggcgtcagat gggtggtggc cttcttcagg cagttcttca ggtcggtcac caaggtggac   660
tacctcacct tgagggcagg cttcatcaac gcgcacttgt cgcagaacag caagttcgac   720
ttccacaagt acatcaagag gtccatggag gacgacttca agtcgtcgt tggcatcagc   780
ctcccgctgt gggctgtggc gatcctcacc ctcttcctg atatcgacgg gatcggcaca   840
ctcacctggg tttctttcat ccctctcatc atcctcttgt gtgttggaac caagctagag   900
```

```
atgatcatca tggagatggc cctggagatc caggaccggt cgagcgtcat caagggggca    960
cccgtggtcg agcccagcaa caagttcttc tggttccacc gccccgactg ggtcctcttc   1020
ttcatacacc tgacgctgtt ccagaacgcg tttcagatgg cacatttcgt gtggacagtg   1080
gccacgcccg gcttgaagga ctgcttccat atgaacatcg gcctgagcat catgaaggtc   1140
gtgctggggc tggctctcca gttcctgtgc agctacatca ccttcccccct ctacgcgcta   1200 gtcacacaga tgggatcaaa catgaagagg tccatcttcg acgagcagac agccaaggcg   1260
ctgaccaact ggcggaacac ggccaaggag aagaagaagg tccgagacac ggacatgctg   1320
atggcgcaga tgatcggcga cgcaacaccc agccgaggcc cgtccccgat gcctagccgg   1380
ggctcatcgc cggtgcacct gcttcagaag ggcatgggac ggtctgacga tccccagagc   1440
gcaccgacct cgccaaggac catggaggag gctagggaca tgtacccggt tgtggtggcg   1500
catcctgtac acagactaaa tcctgctgac aggagaaggt cggtctcttc atcagccctc   1560
gatgccgaca tccccagcgc agattttccc ttcagccagg gatga                   1605

<210> SEQ ID NO 2
<211> LENGTH: 1605
<212> TYPE: DNA
<213> ORGANISM: Triticum aestivum

<400> SEQUENCE: 2
atggcggagg acgacgggta ccccccagcg aggacgctgc cggagacgcc gtcctgggcg     60
gtggccctcg tcttcgccgt catgatcatc gtgtccgtcc tcctggagca cgcgctccat    120
aagctcggcc agtggttcca caagcggcac aagaacgcgc tggcggaggc gctggagaag    180
atcaaggcgg agctcatgct ggtgggcttc atctcgctgc tgctcgccgt gacgcaggac    240
cccatctccg ggatatgcat ctccgagaag gccgccagca tcatgcggcc ctgcaagctg    300 cccccctggct ccgtcaagag caagtacaaa gactactact gcgccaaaca gggcaaggtg    360
tcgctcatgt ccacgggcag cttgcaccag ctgcacatat tcatcttcgt gctcgccgtc    420
ttccatgtca cctacagcgt catcatcatg gctctaagcc gtctcaagat gagaacctgg    480
aagaaatggg agacagagac cgcctccctg gaataccagt tcgcaaatga tcctgcgcgg    540
ttccgcttca cgcaccagac gtcgttcgtg aagcggcacc tgggcctctc cagcaccccc    600
ggcgtcagat gggtggtggc cttcttcagg cagttcttca ggtcggtcac caaggtggac    660 tacctcaccct tgagggcagg cttcatcaac gcgcatttgt cgcataacag caagttcgac    720
ttccacaagt acatcaagag gtccatggag gacgacttca agtcgtcgt tggcatcagc    780 ctcccgctgt ggtgtgtggc gatcctcacc ctcttccttg acattgacgg gatcggcacg    840
ctcacctgga tttctttcat ccctctcgtc atcctcttgt gtgttggaac caagctggag    900
atgatcatca tggagatggc cctggagatc caggaccggg cgagcgtcat caagggggcg    960
cccgtggttg agcccagcaa caagttcttc tggttccacc gccccgactg ggtcctcttc   1020
ttcatacacc tgacgctatt ccagaacgcg tttcagatgg cacatttcgt gtggacagtg   1080
gccacgcccg gcttgaagaa atgcttccat atgcacatcg gcctgagcat catgaaggtc   1140
gtgctggggc tggctcttca gttcctctgc agctatatca ccttcccgct ctacgcgctc   1200
gtcacacaga tgggatcaaa catgaagagg tccatcttcg acgagcagac ggccaaggcg   1260
ctgacaaact ggcggaacac ggccaaggag aagaagaagg tccgagacac ggacatgctg   1320
atggcgcaga tgatcggcga cgcgacgccc agccgagggg cgtcgcccat gcctagccgg   1380
```

| | |
|---|---|
| ggctcgtcgc cagtgcacct gcttcacaag ggcatgggac ggtccgacga tccccagagc | 1440 |
| acgccaacct cgccaagggc catggaggag gctagggaca tgtacccggt tgtggtggcg | 1500 |
| catccagtgc acagactaaa tcctgctgac aggagaaggt cggtctcgtc gtcggcactc | 1560 |
| gatgtcgaca ttcccagcgc agatttttcc ttcagccagg gatga | 1605 |

<210> SEQ ID NO 3
<211> LENGTH: 1605
<212> TYPE: DNA
<213> ORGANISM: Triticum aestivum

<400> SEQUENCE: 3

| | |
|---|---|
| atggcggagg acgacgggta ccccccggcg cggacgctgc cggagacgcc gtcctgggcg | 60 |
| gtggcgctcg tcttcgccgt catgatcatc gtgtccgtcc tcctggagca cgcgctccac | 120 |
| aagctcggcc agtggttcca caagcggcac aagaacgcgc tggcggaggc gctggagaag | 180 |
| atcaaagcgg agctgatgct ggtggggttc atctcgctgc tgctcgccgt gacgcaggac | 240 |
| ccaatctccg ggatatgcat ctccgagaag gccgccagca tcatgcggcc ctgcagcctg | 300 |
| cccctggtt ccgtcaagag caagtacaaa gactactact gcgccaaaaa gggcaaggtg | 360 |
| tcgctaatgt ccacgggcag cttgcaccag ctccacatat tcatcttcgt gctcgccgtc | 420 |
| ttccatgtca cctacagcgt catcatcatg gctctaagcc gtctcaagat gaggacatgg | 480 |
| aagaaatggg agacagagac cgcctccttg aataccagt tcgcaaatga tcctgcgcgg | 540 |
| ttccgcttca cgcaccagac gtcgttcgtg aagcgtcacc tgggcctctc cagcaccccc | 600 |
| ggcatcagat gggtggtggc cttcttcagg cagttcttca ggtcggtcac caaggtggac | 660 |
| tacctcaccc tgagggcagg cttcatcaac gcgcatttgt cgcataacag caagttcgac | 720 |
| ttccacaagt acatcaagag gtccatggag gacgacttca agtcgtcgt tggcatcagc | 780 |
| ctcccgctgt ggtgtgtggc gatcctcacc ctcttccttg atattgacgg atcggcacg | 840 |
| ctcacctgga tttctttcat ccctctcgtc atcctcttgt gtgttggaac caagctggag | 900 |
| atgatcatca tggagatggc cctggagatc caggaccggg cgagcgtcat caaggggcg | 960 |
| cccgtggttg agcccagcaa caagttcttc tggttccacc gccccgactg ggtcctcttc | 1020 |
| ttcatacacc tgacgctgtt ccagaatgcg tttcagatgg cacatttcgt ctggacagtg | 1080 |
| gccacgcccg gcttgaagaa atgcttccat atgcacatcg ggctgagcat catgaaggtc | 1140 |
| gtgctggggc tggctcttca gttcctctgc agctatatca ccttcccgct ctacgcgctc | 1200 |
| gtcacacaga tgggatcaaa catgaagagg tccatcttcg acgagcagac ggccaaggcg | 1260 |
| ctgacaaact ggcggaacac ggccaaggag aagaagaagg tccgagacac ggacatgctg | 1320 |
| atggcgcaga tgatcggcga cgcgacgccc agccgagggg cgtcgcccat gcctagccgg | 1380 |
| ggctcgtcgc cagtgcacct gcttcacaag ggcatgggac ggtccgacga tccccagagc | 1440 |
| acgccaacct cgccaagggc catggaggag gctagggaca tgtacccggt tgtggtggcg | 1500 |
| catccagtgc acagactaaa tcctgctgac aggagaaggt cggtctcttc gtcggcactc | 1560 |
| gatgccgaca tccccagcgc agatttttcc ttcagccagg gatga | 1605 |

<210> SEQ ID NO 4
<211> LENGTH: 534
<212> TYPE: PRT
<213> ORGANISM: Triticum aestivum

<400> SEQUENCE: 4

Met Ala Glu Asp Asp Gly Tyr Pro Pro Ala Arg Thr Leu Pro Glu Thr

-continued

```
1               5                   10                  15

Pro Ser Trp Ala Val Ala Leu Val Phe Ala Val Met Ile Ile Val Ser
                20                  25                  30

Val Leu Leu Glu His Ala Leu His Lys Leu Gly Gln Trp Phe His Lys
                35                  40                  45

Arg His Lys Asn Ala Leu Ala Glu Ala Leu Glu Lys Met Lys Ala Glu
            50                  55                  60

Leu Met Leu Val Gly Phe Ile Ser Leu Leu Ala Val Thr Gln Asp
65                      70                  75                  80

Pro Ile Ser Gly Ile Cys Ile Ser Gln Lys Ala Ser Ile Met Arg
                    85                  90                      95

Pro Cys Lys Val Glu Pro Gly Ser Val Lys Ser Lys Tyr Lys Asp Tyr
                100                 105                 110

Tyr Cys Ala Lys Glu Gly Lys Val Ala Leu Met Ser Thr Gly Ser Leu
                115                 120                 125

His Gln Leu His Ile Phe Ile Phe Val Leu Ala Val Phe His Val Thr
            130                 135                 140

Tyr Ser Val Ile Ile Met Ala Leu Ser Arg Leu Lys Met Arg Thr Trp
145                 150                 155                 160

Lys Lys Trp Glu Thr Glu Thr Ala Ser Leu Glu Tyr Gln Phe Ala Asn
                165                 170                 175

Asp Pro Ala Arg Phe Arg Phe Thr His Gln Thr Ser Phe Val Lys Arg
                180                 185                 190

His Leu Gly Leu Ser Ser Thr Pro Gly Val Arg Trp Val Val Ala Phe
            195                 200                 205

Phe Arg Gln Phe Phe Arg Ser Val Thr Lys Val Asp Tyr Leu Thr Leu
            210                 215                 220

Arg Ala Gly Phe Ile Asn Ala His Leu Ser Gln Asn Ser Lys Phe Asp
225                 230                 235                 240

Phe His Lys Tyr Ile Lys Arg Ser Met Glu Asp Asp Phe Lys Val Val
                245                 250                 255

Val Gly Ile Ser Leu Pro Leu Trp Ala Val Ala Ile Leu Thr Leu Phe
                260                 265                 270

Leu Asp Ile Asp Gly Ile Gly Thr Leu Thr Trp Val Ser Phe Ile Pro
            275                 280                 285

Leu Ile Ile Leu Leu Cys Val Gly Thr Lys Leu Glu Met Ile Ile Met
            290                 295                 300

Glu Met Ala Leu Glu Ile Gln Asp Arg Ser Ser Val Ile Lys Gly Ala
305                 310                 315                 320

Pro Val Val Glu Pro Ser Asn Lys Phe Phe Trp Phe His Arg Pro Asp
                    325                 330                 335

Trp Val Leu Phe Phe Ile His Leu Thr Leu Phe Gln Asn Ala Phe Gln
                340                 345                 350

Met Ala His Phe Val Trp Thr Val Ala Thr Pro Gly Leu Lys Asp Cys
            355                 360                 365

Phe His Met Asn Ile Gly Leu Ser Ile Met Lys Val Val Leu Gly Leu
            370                 375                 380

Ala Leu Gln Phe Leu Cys Ser Tyr Ile Thr Phe Pro Leu Tyr Ala Leu
385                 390                 395                 400

Val Thr Gln Met Gly Ser Asn Met Lys Arg Ser Ile Phe Asp Glu Gln
                405                 410                 415

Thr Ala Lys Ala Leu Thr Asn Trp Arg Asn Thr Ala Lys Glu Lys Lys
                420                 425                 430
```

```
Lys Val Arg Asp Thr Asp Met Leu Met Ala Gln Met Ile Gly Asp Ala
            435                 440                 445

Thr Pro Ser Arg Gly Thr Ser Pro Met Pro Ser Arg Gly Ser Ser Pro
    450                 455                 460

Val His Leu Leu Gln Lys Gly Met Gly Arg Ser Asp Asp Pro Gln Ser
465                 470                 475                 480

Ala Pro Thr Ser Pro Arg Thr Met Glu Glu Ala Arg Asp Met Tyr Pro
            485                 490                 495

Val Val Val Ala His Pro Val His Arg Leu Asn Pro Ala Asp Arg Arg
            500                 505                 510

Arg Ser Val Ser Ser Ala Leu Asp Ala Asp Ile Pro Ser Ala Asp
            515                 520                 525

Phe Ser Phe Ser Gln Gly
    530

<210> SEQ ID NO 5
<211> LENGTH: 534
<212> TYPE: PRT
<213> ORGANISM: Triticum aestivum

<400> SEQUENCE: 5

Met Ala Glu Asp Asp Gly Tyr Pro Pro Ala Arg Thr Leu Pro Glu Thr
1               5                   10                  15

Pro Ser Trp Ala Val Ala Leu Val Phe Ala Val Met Ile Ile Val Ser
            20                  25                  30

Val Leu Leu Glu His Ala Leu His Lys Leu Gly Gln Trp Phe His Lys
        35                  40                  45

Arg His Lys Asn Ala Leu Ala Glu Ala Leu Glu Lys Ile Lys Ala Glu
    50                  55                  60

Leu Met Leu Val Gly Phe Ile Ser Leu Leu Ala Val Thr Gln Asp
65                  70                  75                  80

Pro Ile Ser Gly Ile Cys Ile Ser Glu Lys Ala Ala Ser Ile Met Arg
                85                  90                  95

Pro Cys Lys Leu Pro Pro Gly Ser Val Lys Ser Lys Tyr Lys Asp Tyr
            100                 105                 110

Tyr Cys Ala Lys Gln Gly Lys Val Ser Leu Met Ser Thr Gly Ser Leu
        115                 120                 125

His Gln Leu His Ile Phe Ile Phe Val Leu Ala Val Phe His Val Thr
    130                 135                 140

Tyr Ser Val Ile Ile Met Ala Leu Ser Arg Leu Lys Met Arg Thr Trp
145                 150                 155                 160

Lys Lys Trp Glu Thr Glu Thr Ala Ser Leu Glu Tyr Gln Phe Ala Asn
                165                 170                 175

Asp Pro Ala Arg Phe Arg Phe Thr His Gln Thr Ser Phe Val Lys Arg
            180                 185                 190

His Leu Gly Leu Ser Ser Thr Pro Gly Val Arg Trp Val Val Ala Phe
        195                 200                 205

Phe Arg Gln Phe Phe Arg Ser Val Thr Lys Val Asp Tyr Leu Thr Leu
    210                 215                 220

Arg Ala Gly Phe Ile Asn Ala His Leu Ser His Asn Ser Lys Phe Asp
225                 230                 235                 240

Phe His Lys Tyr Ile Lys Arg Ser Met Glu Asp Asp Phe Lys Val Val
                245                 250                 255

Val Gly Ile Ser Leu Pro Leu Trp Cys Val Ala Ile Leu Thr Leu Phe
```

```
        260                 265                 270
Leu Asp Ile Asp Gly Ile Gly Thr Leu Thr Trp Ile Ser Phe Ile Pro
        275                 280                 285
Leu Val Ile Leu Leu Cys Val Gly Thr Lys Leu Glu Met Ile Ile Met
        290                 295                 300
Glu Met Ala Leu Glu Ile Gln Asp Arg Ala Ser Val Ile Lys Gly Ala
305                 310                 315                 320
Pro Val Val Glu Pro Ser Asn Lys Phe Phe Trp Phe His Arg Pro Asp
                325                 330                 335
Trp Val Leu Phe Phe Ile His Leu Thr Leu Phe Gln Asn Ala Phe Gln
            340                 345                 350
Met Ala His Phe Val Trp Thr Val Ala Thr Pro Gly Leu Lys Lys Cys
        355                 360                 365
Phe His Met His Ile Gly Leu Ser Ile Met Lys Val Val Leu Gly Leu
        370                 375                 380
Ala Leu Gln Phe Leu Cys Ser Tyr Ile Thr Phe Pro Leu Tyr Ala Leu
385                 390                 395                 400
Val Thr Gln Met Gly Ser Asn Met Lys Arg Ser Ile Phe Asp Glu Gln
                405                 410                 415
Thr Ala Lys Ala Leu Thr Asn Trp Arg Asn Thr Ala Lys Glu Lys Lys
            420                 425                 430
Lys Val Arg Asp Thr Asp Met Leu Met Ala Gln Met Ile Gly Asp Ala
        435                 440                 445
Thr Pro Ser Arg Gly Ala Ser Pro Met Pro Ser Arg Gly Ser Ser Pro
        450                 455                 460
Val His Leu Leu His Lys Gly Met Gly Arg Ser Asp Asp Pro Gln Ser
465                 470                 475                 480
Thr Pro Thr Ser Pro Arg Ala Met Glu Glu Ala Arg Asp Met Tyr Pro
                485                 490                 495
Val Val Val Ala His Pro Val His Arg Leu Asn Pro Ala Asp Arg Arg
            500                 505                 510
Arg Ser Val Ser Ser Ser Ala Leu Asp Val Asp Ile Pro Ser Ala Asp
        515                 520                 525
Phe Ser Phe Ser Gln Gly
        530

<210> SEQ ID NO 6
<211> LENGTH: 534
<212> TYPE: PRT
<213> ORGANISM: Triticum aestivum

<400> SEQUENCE: 6

Met Ala Glu Asp Asp Gly Tyr Pro Pro Ala Arg Thr Leu Pro Glu Thr
1               5                   10                  15
Pro Ser Trp Ala Val Ala Leu Val Phe Ala Val Met Ile Ile Val Ser
            20                  25                  30
Val Leu Leu Glu His Ala Leu His Lys Leu Gly Gln Trp Phe His Lys
        35                  40                  45
Arg His Lys Asn Ala Leu Ala Glu Ala Leu Glu Lys Ile Lys Ala Glu
    50                  55                  60
Leu Met Leu Val Gly Phe Ile Ser Leu Leu Leu Ala Val Thr Gln Asp
65              70                  75                  80
Pro Ile Ser Gly Ile Cys Ile Ser Glu Lys Ala Ala Ser Ile Met Arg
                85                  90                  95
```

-continued

```
Pro Cys Ser Leu Pro Pro Gly Ser Val Lys Ser Lys Tyr Lys Asp Tyr
                100                 105                 110

Tyr Cys Ala Lys Lys Gly Lys Val Ser Leu Met Ser Thr Gly Ser Leu
            115                 120                 125

His Gln Leu His Ile Phe Ile Phe Val Leu Ala Val Phe His Val Thr
        130                 135                 140

Tyr Ser Val Ile Ile Met Ala Leu Ser Arg Leu Lys Met Arg Thr Trp
145                 150                 155                 160

Lys Lys Trp Glu Thr Glu Thr Ala Ser Leu Glu Tyr Gln Phe Ala Asn
                165                 170                 175

Asp Pro Ala Arg Phe Arg Phe Thr His Gln Thr Ser Phe Val Lys Arg
            180                 185                 190

His Leu Gly Leu Ser Ser Thr Pro Gly Ile Arg Trp Val Val Ala Phe
        195                 200                 205

Phe Arg Gln Phe Phe Arg Ser Val Thr Lys Val Asp Tyr Leu Thr Leu
210                 215                 220

Arg Ala Gly Phe Ile Asn Ala His Leu Ser His Asn Ser Lys Phe Asp
225                 230                 235                 240

Phe His Lys Tyr Ile Lys Arg Ser Met Glu Asp Phe Lys Val Val
            245                 250                 255

Val Gly Ile Ser Leu Pro Leu Trp Cys Val Ala Ile Leu Thr Leu Phe
                260                 265                 270

Leu Asp Ile Asp Gly Ile Gly Thr Leu Thr Trp Ile Ser Phe Ile Pro
            275                 280                 285

Leu Val Ile Leu Leu Cys Val Gly Thr Lys Leu Glu Met Ile Ile Met
        290                 295                 300

Glu Met Ala Leu Glu Ile Gln Asp Arg Ala Ser Val Ile Lys Gly Ala
305                 310                 315                 320

Pro Val Val Glu Pro Ser Asn Lys Phe Phe Trp Phe His Arg Pro Asp
                325                 330                 335

Trp Val Leu Phe Phe Ile His Leu Thr Leu Phe Gln Asn Ala Phe Gln
            340                 345                 350

Met Ala His Phe Val Trp Thr Val Ala Thr Pro Gly Leu Lys Lys Cys
        355                 360                 365

Phe His Met His Ile Gly Leu Ser Ile Met Lys Val Val Leu Gly Leu
370                 375                 380

Ala Leu Gln Phe Leu Cys Ser Tyr Ile Thr Phe Pro Leu Tyr Ala Leu
385                 390                 395                 400

Val Thr Gln Met Gly Ser Asn Met Lys Arg Ser Ile Phe Asp Glu Gln
                405                 410                 415

Thr Ala Lys Ala Leu Thr Asn Trp Arg Asn Thr Ala Lys Glu Lys Lys
            420                 425                 430

Lys Val Arg Asp Thr Asp Met Leu Met Ala Gln Met Ile Gly Asp Ala
        435                 440                 445

Thr Pro Ser Arg Gly Ala Ser Pro Met Pro Ser Arg Gly Ser Ser Pro
450                 455                 460

Val His Leu Leu His Lys Gly Met Gly Arg Ser Asp Asp Pro Gln Ser
465                 470                 475                 480

Thr Pro Thr Ser Pro Arg Ala Met Glu Glu Ala Arg Asp Met Tyr Pro
                485                 490                 495

Val Val Val Ala His Pro Val His Arg Leu Asn Pro Ala Asp Arg Arg
            500                 505                 510

Arg Ser Val Ser Ser Ser Ala Leu Asp Ala Asp Ile Pro Ser Ala Asp
```

```
              515                 520                 525
Phe Ser Phe Ser Gln Gly
    530

<210> SEQ ID NO 7
<211> LENGTH: 4017
<212> TYPE: DNA
<213> ORGANISM: Artificial Sequence
<220> FEATURE:
<223> OTHER INFORMATION: UBI-attr1-attr2-Nos

<400> SEQUENCE: 7
tcgtgcccct ctctagagat aatgagcatt gcatgtctaa gttataaaaa attaccacat      60
atttttttg tcacacttgt ttgaagtgca gtttatctat ctttatacat atatttaaac     120
tttactctac gaataatata atctatagta ctacaataat atcagtgttt tagagaatca     180
tataaatgaa cagttagaca tggtctaaag gacaattgag tattttgaca acaggactct     240
acagttttat cttttagtg tgcatgtgtt ctccttttt tttgcaaata gcttcaccta     300
tataatactt catccatttt attagtacat ccatttaggg tttagggtta atggttttta     360
tagactaatt tttttagtac atctatttta ttctatttta gcctctaaat taagaaaact     420
aaaactctat tttagttttt ttatttaata atttagatat aaaatagaat aaaataaagt     480
gactaaaaat taaacaaata ccctttaaga aattaaaaaa actaaggaaa cattttctt      540
gtttcgagta gataatgcca gcctgttaaa cgccgtcgac gagtctaacg gacaccaacc     600
agcgaaccag cagcgtcgcg tcgggccaag cgaagcagac ggcacggcat ctctgtcgct     660
gcctctggac ccctctcgat cgagagttcc gctccaccgt tggacttgct ccgctgtcgg     720
catccagaaa ttgcgtggcg gagcggcaga cgtgagccgg cacggcaggc ggcctcctcc     780
tcctctcacg gcaccggcag ctacggggga ttcctttccc accgctcctt cgcttcccct     840
tcctcgcccg ccgtaataaa tagacacccc ctccacaccc tctttcccca acctcgtgtt     900
gttcggagcg cacacacaca caaccagatc tcccccaaat ccacccgtcg gcacctccgc     960
ttcaaggtac gccgctcgtc ctcccccccc cccctctct accttctcta gatcggcgtt    1020
ccggtccatg gttagggccc ggtagttcta cttctgttca tgtttgtgtt agatccgtgt    1080
ttgtgttaga tccgtgctgc tagcgttcgt acacggatgc gacctgtacg tcagacacgt    1140
tctgattgct aacttgccag tgtttctctt tggggaatcc tgggatggct ctagccgttc    1200
cgcagacggg atcgatttca tgatttttt tgtttcgttg catagggttt ggtttgccct    1260
tttcctttat ttcaatatat gccgtgcact tgttgtcgg gtcatctttt catgcttttt    1320
tttgtcttgg ttgtgatgat gtggtctggt tgggcggtcg ttctagatcg gagtagaatt    1380
aattctgttt caaactacct ggtggattta ttaattttgg atctgtatgt gtgtgccata    1440
catattcata gttacgaatt gaagatgatg gatggaaata tcgatctagg ataggtatac    1500
atgttgatgc gggttttact gatgcatata cagagatgct tttgttcgc ttggttgtga    1560
tgatgtggtg tggttgggcg tcgttcatt cgttctagat cggagtagaa tactgtttca    1620
aactacctgg tgtatttatt aatttttggaa ctgtatgtgt gtgtcataca tcttcatagt    1680
tacgagttta agatggatgg aaatatcgat ctaggatagg tatacatgtt gatgtgggtt    1740
ttactgatgc atatacatga tggcatatgc agcatctatt catatgctct aaccttgagt    1800
acctatctat tataataaac aagtatgttt tataattatt ttgatcttga tatacttgga    1860
tgatggcata tgcagcagct atatgtggat ttttttagcc ctgccttcat acgctattta    1920
```

```
tttgcttggt actgtttctt ttgtcgatgc tcaccctgtt gtttggtgtt acttctgcaa    1980
aagcttgcca agctatcaaa caagtttgta caaaaaagct gaacgagaaa cgtaaaatga    2040
tataaatatc aatatattaa attagatttt gcataaaaaa cagactacat aatactgtaa    2100
aacacaacat atccagtcac tatggcggcc gcattaggca ccccaggctt atactttat     2160
gcttccggct cgtataatgt gtggattttg agttaggatc cggcgagatt ttcaggagct    2220
aaggaagcta aaatggagaa aaaaatcact ggatatacca ccgttgatat atcccaatgg    2280
catcgtaaag aacattttga ggcatttcag tcagttgctc aatgtaccta taaccagacc    2340
gttcagctgg atattacggc cttttttaaag accgtaaaga aaataagca caagttttat    2400
ccggccttta ttcacattct tgcccgcctg atgaatgctc atccggaatt ccgtatggca    2460
atgaaagacg gtgagctggt gatatgggat agtgttcacc cttgttacac cgttttccat    2520
gagcaaactg aaacgttttc atcgctctgg agtgaatacc acgacgattt ccggcagttt    2580
ctacacatat attcgcaaga tgtggcgtgt tacggtgaaa acctggccta tttccctaaa    2640
gggtttattg agaatatgtt tttcgtctca gccaatccct gggtgagttt caccagtttt    2700
gatttaaacg tggccaatat ggacaacttc ttcgcccccg ttttcaccat gggcaaatat    2760
tatacgcaag cgacaaggt gctgatgccg ctggcgattc aggttcatca tgccgtctgt     2820
gatggcttcc atgtcggcag aatgcttaat gaattacaac agtactgcga tgagtggcag    2880
ggcggggcgt aatctagagg atccggctta ctaaaagcca gataacagta tgcgtatttg    2940
cgcgctgatt tttgcggtat aagaatatat actgatatgt atacccgaag tatgtcaaaa    3000
agaggtgtgc tatgaagcag cgtattacag tgacagttga cagcgacagc tatcagttgc    3060
tcaaggcata tatgatgtca atatctccgg tctggtaagc acaaccatgc agaatgaagc    3120
ccgtcgtctg cgtgccgaac gctggaaagc ggaaaatcag gaagggatgg ctgaggtcgc    3180
ccggtttatt gaaatgaacg gctcttttgc tgacgagaac agggactggt gaaatgcagt    3240
ttaaggttta cacctataaa agagagagcc gttatcgtct gtttgtggat gtacagagtg    3300
atattattga cacgcccggg cgacggatgg tgatcccccct ggccagtgca cgtctgctgt   3360
cagataaagt ctcccgtgaa ctttacccgg tggtgcatat cggggatgaa agctggcgca    3420
tgatgaccac cgatatggcc agtgtgccgg tctccgttat cggggaagaa gtggctgatc    3480
tcagccaccg cgaaaatgac atcaaaaacg ccattaacct gatgttctgg ggaatataaa    3540
tgtcaggctc ccttatacac agccagtctg caggtcgacc atagtgactg gatatgttgt    3600
gttttacagt attatgtagt ctgttttttta tgcaaaatct aatttaatat attgatatttt    3660
atatcatttt acgtttctcg ttcagctttc ttgtacaaag tggttcgata attccttaat    3720
taactagttc tagagcggcc gcccaccgcg gtggagctcg aatttccccg atcgttcaaa    3780
catttggcaa taaagtttct taagattgaa tcctgttgcc ggtcttgcga tgattatcat    3840
ataatttctg ttgaattacg ttaagcatgt aataattaac atgtaatgca tgacgttatt    3900
tatgagatgg gttttttatga ttagagtccc gcaattatac atttaatacg cgatagaaaa    3960
caaaatatag cgcgcaaact aggataaatt atcgcgcgcg gtgtcatcta tgttact       4017
```

<210> SEQ ID NO 8
<211> LENGTH: 2202
<212> TYPE: DNA
<213> ORGANISM: Artificial Sequence
<220> FEATURE:
<223> OTHER INFORMATION: TAL-L vector

<400> SEQUENCE: 8

-continued

```
tctagaatgg tggatctacg cacgctcggc tacagtcagc agcagcaaga gaagatcaaa    60
ccgaaggtgc gttcgacagt ggcgcagcac cacgaggcac tggtgggcca tgggtttaca   120
cacgcgcaca tcgttgcgct cagccaacac ccggcagcgt tagggaccgt cgctgtcacg   180
tatcagcaca taatcacggc gttgccagag gcgacacacg aagacatcgt tggcgtcggc   240
aaacagtggt ccggcgcacg cgccctggag gccttgctca cggatgcggg ggagttgaga   300
ggtccgccgt tacagttgga cacaggccaa cttgtgaaga ttgcaaaacg tggcggcgtg   360
accgcaatgg aggcagtgca tgcatcgcgc aatgcactga cgggtgcccc cctgaacctg   420
accccggacc aagtggtggc tatcgccagc acgatggcg gcaagcaagc gctcgaaacg    480
gtgcagcggc tgttgccggt gctgtgccag gaccatggcc tgaccccgga ccaagtggtg   540
gctatcgcca gcaacaatgg cggcaagcaa gcgctcgaaa cggtgcagcg gctgttgccg   600
gtgctgtgcc aggaccatgg cctgactccg gaccaagtgg tggctatcgc cagccacgat   660
ggcggcaagc aagcgctcga acggtgcag cggctgttgc cggtgctgtg ccaggaccat    720
ggcctgaccc cggaccaagt ggtggctatc gccagcaacg gtggcggcaa gcaagcgctc   780
gaaacggtgc agcggctgtt gccggtgctg tgccaggacc atggcctgac cccggaccaa   840
gtggtggcta tcgccagcaa caatggcggc aagcaagcgc tcgaaacggt gcagcggctg   900
ttgccggtgc tgtgccagga ccatggcctg actccggacc aagtggtggc tatcgccagc   960
cacgatggcg gcaagcaagc gctcgaaacg gtgcagcggc tgttgccggt gctgtgccag  1020
gaccatggcc tgaccccgga ccaagtggtg gctatcgcca gcaacggtgg cggcaagcaa  1080
gcgctcgaaa cggtgcagcg gctgttgccg gtgctgtgcc aggaccatgg cctgaccccg  1140
gaccaagtgg tggctatcgc cagcaacaat ggcggcaagc aagcgctcga acggtgcag   1200
cggctgttgc cggtgctgtg ccaggaccat ggcctgactc cggaccaagt ggtggctatc  1260
gccagccacg atggcggcaa gcaagcgctc gaaacggtgc agcggctgtt gccggtgctg  1320
tgccaggacc atggcctgac cccggaccaa gtggtggcta tcgccagcaa cggtggcggc  1380
aagcaagcgc tcgaaacggt gcagcggctg ttgccggtgc tgtgccagga ccatggcctg  1440
accccggacc aagtggtggc tatcgccagc acgatggcg gcaagcaagc gctcgaaacg   1500
gtgcagcggc tgttgccggt gctgtgccag gaccatggcc tgaccccgga ccaagtggtg  1560
gctatcgcca gcaacaatgg cggcaagcaa gcgctcgaaa cggtgcagcg gctgttgccg  1620
gtgctgtgcc aggaccatgg cctgactccg gaccaagtgg tggctatcgc cagccacgat  1680
ggcggcaagc aagcgctcga acggtgcag cggctgttgc cggtgctgtg ccaggaccat   1740
ggcctgactc cggaccaagt ggtggctatc gccagccacg atggcggcaa gcaagcgctc  1800
gaaacggtgc agcggctgtt gccggtgctg tgccaggacc atggcctgac cccggaccaa  1860
gtggtggcta tcgccagcaa caatggcggc aagcaagcgc tcgaaacggt gcagcggctg  1920
ttgccggtgc tgtgccagga ccatggcctg accccggacc aagtggtggc tatcgccagc  1980
aacggtggcg gcaagcaagc gctcgaaagc attgtggccc agctgagccg gcctgatccg  2040
gcgttggccg cgttgaccaa cgaccacctc gtcgccttgg cctgcctcgg cggacgtcct  2100
gccatggatc agtgaaaaa gggattgccg cacgcgccgg aattgatcag aagagtcaat   2160
cgccgtattg gcgaacgcac gtcccatcgc gttgccggat cc                     2202
```

<210> SEQ ID NO 9
<211> LENGTH: 2304
<212> TYPE: DNA

<213> ORGANISM: Artificial Sequence
<220> FEATURE:
<223> OTHER INFORMATION: TAL-R

<400> SEQUENCE: 9

```
tctagaatgg tggatctacg cacgctcggc tacagtcagc agcagcaaga gaagatcaaa      60
ccgaaggtgc gttcgacagt ggcgcagcac cacgaggcac tggtgggcca tgggtttaca     120
cacgcgcaca tcgttgcgct cagccaacac ccggcagcgt tagggaccgt cgctgtcacg     180
tatcagcaca taatcacggc gttgccagag gcgacacacg aagacatcgt tggcgtcggc     240
aaacagtggt ccggcgcacg cgccctggag gccttgctca cggatgcggg ggagttgaga     300
ggtccgccgt tacagttgga cacaggccaa cttgtgaaga ttgcaaaacg tggcggcgtg     360
accgcaatgg aggcagtgca tgcatcgcgc aatgcactga cggtgccccc cctgaacctg     420
accccggacc aagtggtggc tatcgccagc aacaagggcg gcaagcaagc gctcgaaacg     480
gtgcagcggc tgttgccggt gctgtgccag gaccatggcc tgaccccgga ccaagtggtg     540
gctatcgcca gcaacaaggg cggcaagcaa gcgctcgaaa cggtgcagcg gctgttgccg     600
gtgctgtgcc aggaccatgg cctgaccccg gaccaagtgg tggctatcgc cagcaacaag     660
ggcggcaagc aagcgctcga acggtgcag cggctgttgc cggtgctgtg ccaggaccat     720
ggcctgaccc cggaccaagt ggtggctatc gccagcaaca ttggcggcaa gcaagcgctc     780
gaaacggtgc agcggctgtt gccggtgctg tgccaggacc atggcctgac cccggaccaa     840
gtggtggcta tcgccagcaa caagggcggc aagcaagcgc tcgaaacggt gcagcggctg     900
ttgccggtgc tgtgccagga ccatggcctg accccggacc aagtggtggc tatcgccagc     960
aacattggcg gcaagcaagc gctcgaaacg gtgcagcggc tgttgccggt gctgtgccag    1020
gaccatggcc tgaccccgga ccaagtggtg gctatcgcca gcaacggtgg cggcaagcaa    1080
gcgctcgaaa cggtgcagcg gctgttgccg gtgctgtgcc aggaccatgg cctgaccccg    1140
gaccaagtgg tggctatcgc cagcaacaag gcggcaagc aagcgctcga acggtgcag    1200
cggctgttgc cggtgctgtg ccaggaccat ggcctgactc cggaccaagt ggtggctatc    1260
gccagccacg atggcggcaa gcaagcgctc gaaacggtgc agcggctgtt gccggtgctg    1320
tgccaggacc atggcctgac cccggaccaa gtggtggcta tcgccagcaa cattggcggc    1380
aagcaagcgc tcgaaacggt gcagcggctg ttgccggtgc tgtgccagga ccatggcctg    1440
accccggacc aagtggtggc tatcgccagc aacggtggcg gcaagcaagc gctcgaaacg    1500
gtgcagcggc tgttgccggt gctgtgccag gaccatggcc tgaccccgga ccaagtggtg    1560
gctatcgcca gcaacattgg cggcaagcaa gcgctcgaaa cggtgcagcg gctgttgccg    1620
gtgctgtgcc aggaccatgg cctgaccccg gaccaagtgg tggctatcgc cagcaacggt    1680
ggcggcaagc aagcgctcga acggtgcag cggctgttgc cggtgctgtg ccaggaccat    1740
ggcctgactc cggaccaagt ggtggctatc gccagccacg atggcggcaa gcaagcgctc    1800
gaaacggtgc agcggctgtt gccggtgctg tgccaggacc atggcctgac tccggaccaa    1860
gtggtggcta tcgccagcca cgatggcggc aagcaagcgc tcgaaacggt gcagcggctg    1920
ttgccggtgc tgtgccagga ccatggcctg actccggacc aagtggtggc tatcgccagc    1980
cacgatggcg gcaagcaagc gctcgaaacg gtgcagcggc tgttgccggt gctgtgccag    2040
gaccatggcc tgaccccgga ccaagtggtg gctatcgcca gcaacaaggg cggcaagcaa    2100
gcgctcgaaa gcattgtggc ccagctgagc cggcctgatc cggcgttggc cgcgttgacc    2160
aacgaccacc tcgtcgcctt ggcctgcctc ggcggacgtc ctgccatgga tgcagtgaaa    2220
```

-continued

```
aagggattgc cgcacgcgcc ggaattgatc agaagagtca atcgccgtat tggcgaacgc    2280
acgtcccatc gcgttgccgg atcc                                           2304

<210> SEQ ID NO 10
<211> LENGTH: 6219
<212> TYPE: DNA
<213> ORGANISM: Artificial Sequence
<220> FEATURE:
<223> OTHER INFORMATION: TAL-L and TAL-R

<400> SEQUENCE: 10
caaataatga ttttattttg actgatagtg acctgttcgt tgcaacaaat tgatgagcaa     60 tgcttttta taatgccaac tttgtacaaa aaagcaggct ccgaattcgc ccttcaccat    120
ggattataag gatcacgatg gcgactacaa ggaccacgat attgactaca agacgatga    180 cgataaaatg gctcctaaga aaaagcgcaa agtcggtatc catggcgttc cctctagaat    240
ggtggatcta cgcacgctcg gctacagtca gcagcagcaa gagaagatca aaccgaaggt    300
gcgttcgaca gtggcgcagc accacgaggc actggtgggc catgggttta cacgcgcgca    360
catcgttgcg ctcagccaac acccggcagc gttagggacc gtcgctgtca cgtatcagca    420
cataatcacg gcgttgccag aggcgacaca cgaagacatc gttggcgtcg gcaaacagtg    480
gtccggcgca cgcgccctgg aggccttgct cacggatgcg ggggagttga gaggtccgcc    540
gttacagttg gacacaggcc aacttgtgaa gattgcaaaa cgtggcggcg tgaccgcaat    600
ggaggcagtg catgcatcgc gcaatgcact gacgggtgcc cccctgaacc tgaccccgga    660
ccaagtggtg gctatcgcca gccacgatgg cggcaagcaa gcgctcgaaa cggtgcagcg    720
gctgttgccg gtgctgtgcc aggaccatgg cctgaccccg gaccaagtgg tggctatcgc    780
cagcaacaat ggcggcaagc aagcgctcga aacggtgcag cggctgttgc cggtgctgtg    840
ccaggaccat ggcctgactc cggaccaagt ggtggctatc gccagccacg atggcggcaa    900
gcaagcgctc gaaacggtgc agcggctgtt gccggtgctg tgccaggacc atggcctgac    960
cccggaccaa gtggtggcta tcgccagcaa cggtggcggc aagcaagcgc tcgaaacggt   1020
gcagcggctg ttgccggtgc tgtgccagga ccatggcctg accccggacc aagtggtggc   1080
tatcgccagc aacaatggcg gcaagcaagc gctcgaaacg gtgcagcggc tgttgccggt   1140
gctgtgccag gaccatggcc tgactccgga ccaagtggtg gctatcgcca gccacgatgg   1200
cggcaagcaa gcgctcgaaa cggtgcagcg gctgttgccg gtgctgtgcc aggaccatgg   1260
cctgaccccg gaccaagtgg tggctatcgc cagcaacggt ggcggcaagc aagcgctcga   1320
aacggtgcag cggctgttgc cggtgctgtg ccaggaccat ggcctgaccc cggaccaagt   1380
ggtggctatc gccagcaaca atggcggcaa gcaagcgctc gaaacggtgc agcggctgtt   1440
gccggtgctg tgccaggacc atggcctgac tccggaccaa gtggtggcta tcgccagcca   1500
cgatggcggc aagcaagcgc tcgaaacggt gcagcggctg ttgccggtgc tgtgccagga   1560
ccatggcctg accccggacc aagtggtggc tatcgccagc aacggtggcg gcaagcaagc   1620
gctcgaaacg gtgcagcggc tgttgccggt gctgtgccag gaccatggcc tgaccccgga   1680
ccaagtggtg gctatcgcca gccacgatgg cggcaagcaa gcgctcgaaa cggtgcagcg   1740
gctgttgccg gtgctgtgcc aggaccatgg cctgaccccg gaccaagtgg tggctatcgc   1800
cagcaacaat ggcggcaagc aagcgctcga aacggtgcag cggctgttgc cggtgctgtg   1860
ccaggaccat ggcctgactc cggaccaagt ggtggctatc gccagccacg atggcggcaa   1920
```

```
gcaagcgctc gaaacggtgc agcggctgtt gccggtgctg tgccaggacc atggcctgac    1980
tccggaccaa gtggtggcta tcgccagcca cgatggcggc aagcaagcgc tcgaaacggt    2040
gcagcggctg ttgccggtgc tgtgccagga ccatggcctg accccggacc aagtggtggc    2100
tatcgccagc aacaatggcg gcaagcaagc gctcgaaacg gtgcagcggc tgttgccggt    2160
gctgtgccag gaccatggcc tgaccccgga ccaagtggtg gctatcgcca gcaacggtgg    2220
cggcaagcaa gcgctcgaaa gcattgtggc cagctgagc cggcctgatc cggcgttggc     2280
cgcgttgacc aacgaccacc tcgtcgcctt ggcctgcctc ggcggacgtc ctgccatgga    2340
tgcagtgaaa aagggattgc cgcacgcgcc ggaattgatc agaagagtca atcgccgtat    2400
tggcgaacgc acgtcccatc gcgttgccgg atcccagctg gtgaagtccg agctggaaga    2460
aaaaaagagc gagctgcgcc acaagctcaa gtacgtgccc cacgagtaca tcgagctgat    2520
cgagatcgcc cgcaacagca cccaagaccg catcctggag atgaaagtga tggagttctt    2580
catgaaggtg tacggctacc gcggcaagca cctgggcggc tcccgcaagc ccgatggcgc    2640
catctacacc gtgggctccc ccatcgacta tggcgtcatt gtcgacacca aggcctactc    2700
cggcggctac aacttaccca tcggtcaggc cgacgagatg caacgctacg tgaaggagaa    2760
ccagacccgc aataagcaca ttaatcccaa cgagtggtgg aaggtgtacc cctcctccgt    2820
gaccgagttc aaattcctgt tcgtgtccgg ccacttcaag ggcaattata aggcccaact    2880
gacccgcctg aaccacaaga ccaactgcaa cggcgccgtg ctgtccgtgg aggaactgct    2940
gatcggcggc gagatgatca aggctggtac cctgaccctg aagaggtgc gccgcaagtt     3000 caacaatggt gaaatcaatt tcaggtccgg cggcggagag ggcagaggaa gtcttctaac    3060
atgcggtgac gtggaggaga atcccggccc taggatggac tacaaagacc atgacggtga    3120
ttataaagat catgacatcg attacaagga tgacgatgac aagatggccc ccaagaagaa    3180
gaggaaggtg ggcattcacg gggtgccggc tagcatggtg atctacgca cgctcggcta     3240 cagtcagcag cagcaagaga agatcaaacc gaaggtgcgt tcgacagtgg cgcagcacca    3300
cgaggcactg gtgggccatg gtttacaca cgcgcacatc gttgcgctca gccaacaccc     3360
ggcagcgtta gggaccgtcg ctgtcacgta tcagcacata atcacggcgt tgccagaggc    3420
gacacacgaa gacatcgttg gcgtcggcaa acagtggtcc ggcgcacgcg ccctggaggc    3480
cttgctcacg gatgcggggg agttgagagg tccgccgtta cagttggaca caggccaact    3540
tgtgaagatt gcaaaacgtg gcggcgtgac cgcaatggag gcagtgcatg catcgcgcaa    3600
tgcactgacg ggtgcccccc tgaacctgac cccggaccaa gtggtggcta tcgccagcaa    3660
caagggcggc aagcaagcgc tcgaaacggt gcagcggctg ttgccggtgc tgtgccagga    3720
ccatggcctg accccggacc aagtggtggc tatcgccagc aacaagggcg gcaagcaagc    3780
gctcgaaacg gtgcagcggc tgttgccggt gctgtgccag gaccatggcc tgaccccgga    3840
ccaagtggtg gctatcgcca gcaacaaggg cggcaagcaa gcgctcgaaa cggtgcagcg    3900
gctgttgccg gtgctgtgcc aggaccatgg cctgaccccg accaagtgg tggctatcgc     3960 cagcaacatt ggcggcaagc aagcgctcga acggtgcag cggctgttgc cggtgctgtg      4020
ccaggaccat ggcctgaccc cggaccaagt ggtggctatc gccagcaaca agggcggcaa    4080
gcaagcgctc gaaacggtgc agcggctgtt gccggtgctg tgccaggacc atggcctgac    4140
cccggaccaa gtggtggcta tcgccagcaa cattggcggc aagcaagcgc tcgaaacggt    4200
gcagcggctg ttgccggtgc tgtgccagga ccatggcctg accccggacc aagtggtggc    4260
tatcgccagc aacggtggcg gcaagcaagc gctcgaaacg gtgcagcggc tgttgccggt    4320
```
gctgtgccag gaccatggcc tgaccccgga ccaagtggtg gctatcgcca gcaacaaggg    4380
cggcaagcaa gcgctcgaaa cggtgcagcg gctgttgccg gtgctgtgcc aggaccatgg    4440
cctgactccg gaccaagtgg tggctatcgc cagccacgat ggcggcaagc aagcgctcga    4500
aacggtgcag cggctgttgc cggtgctgtg ccaggaccat ggcctgaccc cggaccaagt    4560
ggtggctatc gccagcaaca ttggcggcaa gcaagcgctc gaaacggtgc agcggctgtt    4620
gccggtgctg tgccaggacc atggcctgac cccggaccaa gtggtggcta tcgccagcaa    4680
cggtggcggc aagcaagcgc tcgaaacggt gcagcggctg ttgccggtgc tgtgccagga    4740
ccatggcctg accccggacc aagtggtggc tatcgccagc aacattggcg gcaagcaagc    4800
gctcgaaacg gtgcagcggc tgttgccggt gctgtgccag gaccatggcc tgaccccgga    4860
ccaagtggtg gctatcgcca gcaacggtgg cggcaagcaa gcgctcgaaa cggtgcagcg    4920
gctgttgccg gtgctgtgcc aggaccatgg cctgactccg gaccaagtgg tggctatcgc    4980
cagccacgat ggcggcaagc aagcgctcga aacggtgcag cggctgttgc cggtgctgtg    5040
ccaggaccat ggcctgactc cggaccaagt ggtggctatc gccagccacg atggcggcaa    5100
gcaagcgctc gaaacggtgc agcggctgtt gccggtgctg tgccaggacc atggcctgac    5160
tccggaccaa gtggtggcta tcgccagcca cgatggcggc aagcaagcgc tcgaaacggt    5220
gcagcggctg ttgccggtgc tgtgccagga ccatggcctg accccggacc aagtggtggc    5280
tatcgccagc aacaagggcg gcaagcaagc gctcgaaagc attgtggccc agctgagccg    5340
gcctgatccg gcgttggccg cgttgaccaa cgaccacctc gtcgccttgg cctgcctcgg    5400
cggacgtcct gccatggatg cagtgaaaaa gggattgccg cacgcgccgg aattgatcag    5460
aagagtcaat cgccgtattg gcgaacgcac gtcccatcgc gttgccagat ctcaactagt    5520
caaaagtgaa ctggaggaga gaaatctgaa cttcgtcat aaattgaaat atgtgcctca    5580
tgaatatatt gaattaattg aaattgccag aaattccact caggatagaa ttcttgaaat    5640
gaaggtaatg gaatttttta tgaaagttta tggatataga ggtaaacatt tgggtggatc    5700
aaggaaaccg gacggagcaa tttatactgt cggatctcct attgattacg gtgtgatcgt    5760
ggatactaaa gcttatagcg gaggttataa tctgccaatt ggccaagcag atgaaatgga    5820
gcgatatgtc gaagaaaatc aaacacgaaa caaacatctc aaccctaatg aatggtggaa    5880
agtctatcca tcttctgtaa cggaatttaa gttttatttt gtgagtggtc actttaaagg    5940
aaactacaaa gctcagctta cacgattaaa tcatatcact aattgtaatg gagctgttct    6000
tagtgtagaa gagcttttaa ttggtggaga atgattaaa gccggcacat taaccttaga    6060
ggaagtgaga cggaaattta ataacggcga gataaacttt taatagaagg gcgaattcga    6120
cccagctttc ttgtacaaag ttggcattat aaaaaataat tgctcatcaa tttgttgcaa    6180
cgaacaggtc actatcagtc aaaataaaat cattatttg                           6219

<210> SEQ ID NO 11
<211> LENGTH: 5868
<212> TYPE: DNA
<213> ORGANISM: Artificial Sequence
<220> FEATURE:
<223> OTHER INFORMATION: TAL-L and TAL-R in pYP010

<400> SEQUENCE: 11
atggtggatc tacgcacgct cggctacagt cagcagcagc aagagaagat caaaccgaag      60
gtgcgttcga cagtggcgca gcaccacgag gcactggtgg gccatgggtt tacacacgcg     120

```
cacatcgttg cgctcagcca acacccggca gcgttaggga ccgtcgctgt cacgtatcag      180
cacataatca cggcgttgcc agaggcgaca cacgaagaca tcgttggcgt cggcaaacag      240
tggtccggcg cacgcgccct ggaggccttg ctcacggatg cgggggagtt gagaggtccg      300
ccgttacagt tggacacagg ccaacttgtg aagattgcaa acgtggcgg cgtgaccgca       360 atggaggcag tgcatgcatc gcgcaatgca ctgacgggtg ccccctgaa cctgaccccg       420 gaccaagtgg tggctatcgc cagccacgat ggcggcaagc aagcgctcga aacggtgcag      480
cggctgttgc cggtgctgtg ccaggaccat ggcctgaccc cggaccaagt ggtggctatc      540
gccagcaaca atggcggcaa gcaagcgctc gaaacggtgc agcggctgtt gccggtgctg      600
tgccaggacc atggcctgac tccggaccaa gtggtggcta tcgccagcca cgatggcggc      660
aagcaagcgc tcgaaacggt gcagcggctg ttgccggtgc tgtgccagga ccatggcctg      720 acccccggacc aagtggtggc tatcgccagc aacggtggcg gcaagcaagc gctcgaaacg    780
gtgcagcggc tgttgccggt gctgtgccag gaccatggcc tgaccccgga ccaagtggtg     840
gctatcgcca gcaacaatgg cggcaagcaa gcgctcgaaa cggtgcagcg gctgttgccg     900
gtgctgtgcc aggaccatgg cctgactccg gaccaagtgg tggctatcgc cagccacgat     960
ggcggcaagc aagcgctcga aacggtgcag cggctgttgc cggtgctgtg ccaggaccat     1020
ggcctgaccc cggaccaagt ggtggctatc gccagcaacg gtggcggcaa gcaagcgctc     1080
gaaacggtgc agcggctgtt gccggtgctg tgccaggacc atggcctgac cccggaccaa     1140
gtggtggcta tcgccagcaa caatggcggc aagcaagcgc tcgaaacggt gcagcggctg     1200
ttgccggtgc tgtgccagga ccatggcctg actccggacc aagtggtggc tatcgccagc     1260
cacgatggcg gcaagcaagc gctcgaaacg gtgcagcggc tgttgccggt gctgtgccag     1320
gaccatggcc tgaccccgga ccaagtggtg gctatcgcca gcaacggtgg cggcaagcaa     1380
gcgctcgaaa cggtgcagcg gctgttgccg gtgctgtgcc aggaccatgg cctgaccccg     1440
gaccaagtgg tggctatcgc cagccacgat ggcggcaagc aagcgctcga aacggtgcag     1500
cggctgttgc cggtgctgtg ccaggaccat ggcctgaccc cggaccaagt ggtggctatc     1560
gccagcaaca atggcggcaa gcaagcgctc gaaacggtgc agcggctgtt gccggtgctg     1620
tgccaggacc atggcctgac tccggaccaa gtggtggcta tcgccagcca cgatggcggc     1680
aagcaagcgc tcgaaacggt gcagcggctg ttgccggtgc tgtgccagga ccatggcctg     1740
actccggacc aagtggtggc tatcgccagc cacgatggcg gcaagcaagc gctcgaaacg     1800
gtgcagcggc tgttgccggt gctgtgccag gaccatggcc tgaccccgga ccaagtggtg     1860
gctatcgcca gcaacaatgg cggcaagcaa gcgctcgaaa cggtgcagcg gctgttgccg     1920
gtgctgtgcc aggaccatgg cctgaccccg gaccaagtgg tggctatcgc cagcaacggt     1980
ggcggcaagc aagcgctcga aagcattgtg gcccagctga gccggcctga tccggcgttg     2040
gccgcgttga ccaacgacca cctcgtcgcc ttggcctgcc tcggcggacg tcctgccatg     2100
gatgcagtga aaaagggatt gccgcacgcg ccggaattga tcagaagagt caatcgccgt     2160
attggcgaac gcacgtccca tcgcgttgcc ggatcccagc tggtgaagtc cgagctggaa     2220
gaaaaaaaga gcgagctgcg ccacaagctc aagtacgtgc cccacgagta catcgagctg     2280
atcgagatcg cccgcaacag cacccaagac cgcatcctgg agatgaaagt gatggagttc     2340
ttcatgaagg tgtacggcta ccgcggcaag cacctgggcg gctcccgcaa gcccgatggc     2400
gccatctaca ccgtgggctc ccccatcgac tatggcgtca ttgtcgacac caaggcctac     2460
tccggcggct acaacttacc catcggtcag gccgacgaga tgcaacgcta cgtgaaggag     2520
```

```
aaccagaccc gcaataagca cattaatccc aacgagtggt ggaaggtgta cccctcctcc    2580
gtgaccgagt tcaaattcct gttcgtgtcc ggccacttca agggcaatta taaggcccaa    2640
ctgacccgcc tgaaccacaa gaccaactgc aacggcgccg tgctgtccgt ggaggaactg    2700
ctgatcggcg gcgagatgat caaggctggt accctgaccc tggaagaggt gcgccgcaag    2760
ttcaacaatg gtgaaatcaa tttcaggtcc ggcggcggag agggcagagg aagtcttcta    2820
acatgcggtg acgtggagga gaatcccggc cctaggatgg actacaaaga ccatgacggt    2880
gattataaag atcatgacat cgattacaag gatgacgatg acaagatggc ccccaagaag    2940
aagaggaagg tgggcattca cggggtgccg gctagcatgg tggatctacg cacgctcggc    3000
tacagtcagc agcagcaaga gaagatcaaa ccgaaggtgc gttcgacagt ggcgcagcac    3060
cacgaggcac tggtgggcca tgggtttaca cacgcgcaca tcgttgcgct cagccaacac    3120
ccggcagcgt tagggaccgt cgctgtcacg tatcagcaca taatcacggc gttgccagag    3180
gcgacacacg aagacatcgt tggcgtcggc aaacagtggt ccggcgcacg cgccctggag    3240
gccttgctca cggatgcggg ggagttgaga ggtccgccgt tacagttgga cacaggccaa    3300
cttgtgaaga ttgcaaaacg tggcggcgtg accgcaatgg aggcagtgca tgcatcgcgc    3360
aatgcactga cgggtgcccc cctgaacctg accccggacc aagtggtggc tatcgccagc    3420
aacaagggcg gcaagcaagc gctcgaaacg gtgcagcggc tgttgccggt gctgtgccag    3480
gaccatggcc tgaccccgga ccaagtggtg gctatcgcca gcaacaaggg cggcaagcaa    3540
gcgctcgaaa cggtgcagcg gctgttgccg gtgctgtgcc aggaccatgg cctgaccccg    3600
gaccaagtgg tggctatcgc cagcaacaag ggcggcaagc aagcgctcga acggtgcag    3660 cggctgttgc cggtgctgtg ccaggaccat ggcctgaccc ggaccaagt ggtggctatc    3720 gccagcaaca ttggcggcaa gcaagcgctc gaaacggtgc agcggctgtt gccggtgctg    3780
tgccaggacc atggcctgac cccgaccaa gtggtggcta tcgccagcaa caagggcggc    3840
aagcaagcgc tcgaaacggt gcagcggctg ttgccggtgt tgtgccagga ccatggcctg    3900
accccggacc aagtggtggc tatcgccagc aacattggcg gcaagcaagc gctcgaaacg    3960
gtgcagcggc tgttgccggt gctgtgccag gaccatggcc tgaccccgga ccaagtggtg    4020
gctatcgcca gcaacggtgg cggcaagcaa gcgctcgaaa cggtgcagcg gctgttgccg    4080
gtgctgtgcc aggaccatgg cctgaccccg gaccaagtgg tggctatcgc cagcaacaag    4140
ggcggcaagc aagcgctcga acggtgcag cggctgttgc cggtgctgtg ccaggaccat    4200
ggcctgactc cggaccaagt ggtggctatc gccagccacg atggcggcaa gcaagcgctc    4260
gaaacggtgc agcggctgtt gccggtgctg tgccaggacc atggcctgac cccggaccaa    4320
gtggtggcta tcgccagcaa cattggcggc aagcaagcgc tcgaaacggt gcagcggctg    4380
ttgccggtgc tgtgccagga ccatggcctg accccggacc aagtggtggc tatcgccagc    4440
aacggtggcg gcaagcaagc gctcgaaacg gtgcagcggc tgttgccggt gctgtgccag    4500
gaccatggcc tgaccccgga ccaagtggtg gctatcgcca gcaacattgg cggcaagcaa    4560
gcgctcgaaa cggtgcagcg gctgttgccg gtgctgtgcc aggaccatgg cctgaccccg    4620
gaccaagtgg tggctatcgc cagcaacggt ggcggcaagc aagcgctcga acggtgcag    4680 cggctgttgc cggtgctgtg ccaggaccat ggcctgactc cggaccaagt ggtggctatc    4740
gccagccacg atggcggcaa gcaagcgctc gaaacggtgc agcggctgtt gccggtgctg    4800
tgccaggacc atggcctgac tccggaccaa gtggtggcta tcgccagcca cgatggcggc    4860
```

-continued

```
aagcaagcgc tcgaaacggt gcagcggctg ttgccggtgc tgtgccagga ccatggcctg    4920
actccggacc aagtggtggc tatcgccagc cacgatggcg gcaagcaagc gctcgaaacg    4980
gtgcagcggc tgttgccggt gctgtgccag gaccatggcc tgaccccgga ccaagtggtg    5040
gctatcgcca gcaacaaggg cggcaagcaa gcgctcgaaa gcattgtggc ccagctgagc    5100
cggcctgatc cggcgttggc cgcgttgacc aacgaccacc tcgtcgcctt ggcctgcctc    5160
ggcggacgtc ctgccatgga tgcagtgaaa aagggattgc cgcacgcgcc ggaattgatc    5220
agaagagtca atcgccgtat tggcgaacgc acgtcccatc gcgttgccag atctcaacta    5280
gtcaaaagtg aactggagga gaagaaatct gaacttcgtc ataaattgaa atatgtgcct    5340
catgaatata ttgaattaat tgaaattgcc agaaattcca ctcaggatag aattcttgaa    5400
atgaaggtaa tggaattttt tatgaaagtt tatggatata gaggtaaaca tttgggtgga    5460
tcaaggaaac cggacggagc aatttatact gtcggatctc ctattgatta cggtgtgatc    5520
gtggatacta aagcttatag cggaggttat aatctgccaa ttggccaagc agatgaaatg    5580
gagcgatatg tcgaagaaaa tcaaacacga acaaacatc tcaaccctaa tgaatggtgg    5640
aaagtctatc catcttctgt aacggaattt aagtttttat ttgtgagtgg tcactttaaa    5700
ggaaactaca agctcagct tacacgatta atcatatca ctaattgtaa tggagctgtt    5760
cttagtgtag aagagctttt aattggtgga gaaatgatta agccggcac attaacctta    5820 gaggaagtga gacggaaatt taataacggc gagataaact tttaatag                5868
```

<210> SEQ ID NO 12
<211> LENGTH: 1954
<212> TYPE: PRT
<213> ORGANISM: Artificial Sequence
<220> FEATURE:
<223> OTHER INFORMATION: TALENs

<400> SEQUENCE: 12

```
Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
                20                  25                  30

Val Gly His Gly Phe Thr His Ala His Ile Val Ala Leu Ser Gln His
            35                  40                  45

Pro Ala Ala Leu Gly Thr Val Ala Val Thr Tyr Gln His Ile Ile Thr
        50                  55                  60

Ala Leu Pro Glu Ala Thr His Glu Asp Ile Val Gly Val Gly Lys Gln
65                  70                  75                  80

Trp Ser Gly Ala Arg Ala Leu Glu Ala Leu Leu Thr Asp Ala Gly Glu
                85                  90                  95

Leu Arg Gly Pro Pro Leu Gln Leu Asp Thr Gly Gln Leu Val Lys Ile
                100                 105                 110

Ala Lys Arg Gly Gly Val Thr Ala Met Glu Ala Val His Ala Ser Arg
            115                 120                 125

Asn Ala Leu Thr Gly Ala Pro Leu Asn Leu Thr Pro Asp Gln Val Val
        130                 135                 140

Ala Ile Ala Ser His Asp Gly Gly Lys Gln Ala Leu Glu Thr Val Gln
145                 150                 155                 160

Arg Leu Leu Pro Val Leu Cys Gln Asp His Gly Leu Thr Pro Asp Gln
                165                 170                 175

Val Val Ala Ile Ala Ser Asn Asn Gly Gly Lys Gln Ala Leu Glu Thr
                180                 185                 190
```

```
Val Gln Arg Leu Leu Pro Val Leu Cys Gln Asp His Gly Leu Thr Pro
        195                 200                 205

Asp Gln Val Val Ala Ile Ala Ser His Asp Gly Gly Lys Gln Ala Leu
        210                 215                 220

Glu Thr Val Gln Arg Leu Leu Pro Val Leu Cys Gln Asp His Gly Leu
225                 230                 235                 240

Thr Pro Asp Gln Val Val Ala Ile Ala Ser Asn Gly Gly Lys Gln
                245                 250                 255

Ala Leu Glu Thr Val Gln Arg Leu Leu Pro Val Leu Cys Gln Asp His
            260                 265                 270

Gly Leu Thr Pro Asp Gln Val Val Ala Ile Ala Ser Asn Asn Gly Gly
            275                 280                 285

Lys Gln Ala Leu Glu Thr Val Gln Arg Leu Leu Pro Val Leu Cys Gln
        290                 295                 300

Asp His Gly Leu Thr Pro Asp Gln Val Val Ala Ile Ala Ser His Asp
305                 310                 315                 320

Gly Gly Lys Gln Ala Leu Glu Thr Val Gln Arg Leu Leu Pro Val Leu
                325                 330                 335

Cys Gln Asp His Gly Leu Thr Pro Asp Gln Val Val Ala Ile Ala Ser
            340                 345                 350

Asn Gly Gly Lys Gln Ala Leu Glu Thr Val Gln Arg Leu Leu Pro
            355                 360                 365

Val Leu Cys Gln Asp His Gly Leu Thr Pro Asp Gln Val Val Ala Ile
        370                 375                 380

Ala Ser Asn Asn Gly Gly Lys Gln Ala Leu Glu Thr Val Gln Arg Leu
385                 390                 395                 400

Leu Pro Val Leu Cys Gln Asp His Gly Leu Thr Pro Asp Gln Val Val
                405                 410                 415

Ala Ile Ala Ser His Asp Gly Gly Lys Gln Ala Leu Glu Thr Val Gln
            420                 425                 430

Arg Leu Leu Pro Val Leu Cys Gln Asp His Gly Leu Thr Pro Asp Gln
            435                 440                 445

Val Val Ala Ile Ala Ser Asn Gly Gly Gly Lys Gln Ala Leu Glu Thr
        450                 455                 460

Val Gln Arg Leu Leu Pro Val Leu Cys Gln Asp His Gly Leu Thr Pro
465                 470                 475                 480

Asp Gln Val Val Ala Ile Ala Ser His Asp Gly Gly Lys Gln Ala Leu
                485                 490                 495

Glu Thr Val Gln Arg Leu Leu Pro Val Leu Cys Gln Asp His Gly Leu
            500                 505                 510

Thr Pro Asp Gln Val Val Ala Ile Ala Ser Asn Asn Gly Gly Lys Gln
            515                 520                 525

Ala Leu Glu Thr Val Gln Arg Leu Leu Pro Val Leu Cys Gln Asp His
        530                 535                 540

Gly Leu Thr Pro Asp Gln Val Val Ala Ile Ala Ser His Asp Gly Gly
545                 550                 555                 560

Lys Gln Ala Leu Glu Thr Val Gln Arg Leu Leu Pro Val Leu Cys Gln
                565                 570                 575

Asp His Gly Leu Thr Pro Asp Gln Val Val Ala Ile Ala Ser His Asp
            580                 585                 590

Gly Gly Lys Gln Ala Leu Glu Thr Val Gln Arg Leu Leu Pro Val Leu
            595                 600                 605
```

-continued

Cys Gln Asp His Gly Leu Thr Pro Asp Gln Val Val Ala Ile Ala Ser
610             615                 620

Asn Asn Gly Gly Lys Gln Ala Leu Glu Thr Val Gln Arg Leu Leu Pro
625             630                 635                 640

Val Leu Cys Gln Asp His Gly Leu Thr Pro Asp Gln Val Val Ala Ile
                645                 650                 655

Ala Ser Asn Gly Gly Lys Gln Ala Leu Glu Ser Ile Val Ala Gln
            660             665                 670

Leu Ser Arg Pro Asp Pro Ala Leu Ala Ala Leu Thr Asn Asp His Leu
        675                 680                 685

Val Ala Leu Ala Cys Leu Gly Gly Arg Pro Ala Met Asp Ala Val Lys
690                 695                 700

Lys Gly Leu Pro His Ala Pro Glu Leu Ile Arg Arg Val Asn Arg Arg
705             710                 715                 720

Ile Gly Glu Arg Thr Ser His Arg Val Ala Gly Ser Gln Leu Val Lys
                725                 730                 735

Ser Glu Leu Glu Glu Lys Ser Glu Leu Arg His Lys Leu Lys Tyr
            740                 745                 750

Val Pro His Glu Tyr Ile Glu Leu Ile Glu Ile Ala Arg Asn Ser Thr
        755                 760                 765

Gln Asp Arg Ile Leu Glu Met Lys Val Met Glu Phe Phe Met Lys Val
770                 775                 780

Tyr Gly Tyr Arg Gly Lys His Leu Gly Gly Ser Arg Lys Pro Asp Gly
785             790                 795                 800

Ala Ile Tyr Thr Val Gly Ser Pro Ile Asp Tyr Gly Val Ile Val Asp
                805                 810                 815

Thr Lys Ala Tyr Ser Gly Gly Tyr Asn Leu Pro Ile Gly Gln Ala Asp
        820                 825                 830

Glu Met Gln Arg Tyr Val Lys Glu Asn Gln Thr Arg Asn Lys His Ile
    835                 840                 845

Asn Pro Asn Glu Trp Trp Lys Val Tyr Pro Ser Ser Val Thr Glu Phe
850                 855                 860

Lys Phe Leu Phe Val Ser Gly His Phe Lys Gly Asn Tyr Lys Ala Gln
865                 870                 875                 880

Leu Thr Arg Leu Asn His Lys Thr Asn Cys Asn Gly Ala Val Leu Ser
                885                 890                 895

Val Glu Glu Leu Leu Ile Gly Gly Glu Met Ile Lys Ala Gly Thr Leu
            900                 905                 910

Thr Leu Glu Glu Val Arg Arg Lys Phe Asn Asn Gly Glu Ile Asn Phe
        915                 920                 925

Arg Ser Gly Gly Glu Gly Arg Gly Ser Leu Leu Thr Cys Gly Asp
930                 935                 940

Val Glu Glu Asn Pro Gly Pro Arg Met Asp Tyr Lys Asp His Asp Gly
945             950                 955                 960

Asp Tyr Lys Asp His Asp Ile Asp Tyr Lys Asp Asp Asp Lys Met
                965                 970                 975

Ala Pro Lys Lys Lys Arg Lys Val Gly Ile His Gly Val Pro Ala Ser
            980                 985                 990

Met Val Asp Leu Arg Thr Leu Gly Tyr Ser Gln Gln Gln Gln Glu Lys
        995                 1000                1005

Ile Lys Pro Lys Val Arg Ser Thr Val Ala Gln His His Glu Ala Leu
    1010                1015                1020

Val Gly His Gly Phe Thr His Ala His Ile Val Ala Leu Ser Gln His

-continued

```
           1025                1030                1035                1040
      Pro Ala Ala Leu Gly Thr Val Ala Val Thr Tyr Gln His Ile Ile Thr
                   1045                1050                1055
      Ala Leu Pro Glu Ala Thr His Glu Asp Ile Val Gly Val Gly Lys Gln
                   1060                1065                1070
      Trp Ser Gly Ala Arg Ala Leu Glu Ala Leu Leu Thr Asp Ala Gly Glu
                   1075                1080                1085
      Leu Arg Gly Pro Pro Leu Gln Leu Asp Thr Gly Gln Leu Val Lys Ile
                   1090                1095                1100
      Ala Lys Arg Gly Gly Val Thr Ala Met Glu Ala Val His Ala Ser Arg
           1105                1110                1115                1120
      Asn Ala Leu Thr Gly Ala Pro Leu Asn Leu Thr Pro Asp Gln Val Val
                   1125                1130                1135
      Ala Ile Ala Ser Asn Lys Gly Gly Lys Gln Ala Leu Glu Thr Val Gln
                   1140                1145                1150
      Arg Leu Leu Pro Val Leu Cys Gln Asp His Gly Leu Thr Pro Asp Gln
                   1155                1160                1165
      Val Val Ala Ile Ala Ser Asn Lys Gly Gly Lys Gln Ala Leu Glu Thr
           1170                1175                1180
      Val Gln Arg Leu Leu Pro Val Leu Cys Gln Asp His Gly Leu Thr Pro
      1185                1190                1195                1200
      Asp Gln Val Val Ala Ile Ala Ser Asn Lys Gly Gly Lys Gln Ala Leu
                   1205                1210                1215
      Glu Thr Val Gln Arg Leu Leu Pro Val Leu Cys Gln Asp His Gly Leu
                   1220                1225                1230
      Thr Pro Asp Gln Val Val Ala Ile Ala Ser Asn Ile Gly Gly Lys Gln
                   1235                1240                1245
      Ala Leu Glu Thr Val Gln Arg Leu Leu Pro Val Leu Cys Gln Asp His
                   1250                1255                1260
      Gly Leu Thr Pro Asp Gln Val Val Ala Ile Ala Ser Asn Lys Gly Gly
      1265                1270                1275                1280
      Lys Gln Ala Leu Glu Thr Val Gln Arg Leu Leu Pro Val Leu Cys Gln
                   1285                1290                1295
      Asp His Gly Leu Thr Pro Asp Gln Val Val Ala Ile Ala Ser Asn Ile
                   1300                1305                1310
      Gly Gly Lys Gln Ala Leu Glu Thr Val Gln Arg Leu Leu Pro Val Leu
                   1315                1320                1325
      Cys Gln Asp His Gly Leu Thr Pro Asp Gln Val Val Ala Ile Ala Ser
                   1330                1335                1340
      Asn Gly Gly Gly Lys Gln Ala Leu Glu Thr Val Gln Arg Leu Leu Pro
      1345                1350                1355                1360
      Val Leu Cys Gln Asp His Gly Leu Thr Pro Asp Gln Val Val Ala Ile
                   1365                1370                1375
      Ala Ser Asn Lys Gly Gly Lys Gln Ala Leu Glu Thr Val Gln Arg Leu
                   1380                1385                1390
      Leu Pro Val Leu Cys Gln Asp His Gly Leu Thr Pro Asp Gln Val Val
                   1395                1400                1405
      Ala Ile Ala Ser His Asp Gly Gly Lys Gln Ala Leu Glu Thr Val Gln
                   1410                1415                1420
      Arg Leu Leu Pro Val Leu Cys Gln Asp His Gly Leu Thr Pro Asp Gln
      1425                1430                1435                1440
      Val Val Ala Ile Ala Ser Asn Ile Gly Gly Lys Gln Ala Leu Glu Thr
                   1445                1450                1455
```

```
Val Gln Arg Leu Leu Pro Val Leu Cys Gln Asp His Gly Leu Thr Pro
            1460                1465                1470

Asp Gln Val Val Ala Ile Ala Ser Asn Gly Gly Lys Gln Ala Leu
    1475                1480                1485

Glu Thr Val Gln Arg Leu Leu Pro Val Leu Cys Gln Asp His Gly Leu
            1490                1495                1500

Thr Pro Asp Gln Val Val Ala Ile Ala Ser Asn Ile Gly Gly Lys Gln
1505                1510                1515                1520

Ala Leu Glu Thr Val Gln Arg Leu Leu Pro Val Leu Cys Gln Asp His
            1525                1530                1535

Gly Leu Thr Pro Asp Gln Val Val Ala Ile Ala Ser Asn Gly Gly Gly
            1540                1545                1550

Lys Gln Ala Leu Glu Thr Val Gln Arg Leu Leu Pro Val Leu Cys Gln
            1555                1560                1565

Asp His Gly Leu Thr Pro Asp Gln Val Val Ala Ile Ala Ser His Asp
            1570                1575                1580

Gly Gly Lys Gln Ala Leu Glu Thr Val Gln Arg Leu Leu Pro Val Leu
1585                1590                1595                1600

Cys Gln Asp His Gly Leu Thr Pro Asp Gln Val Val Ala Ile Ala Ser
            1605                1610                1615

His Asp Gly Gly Lys Gln Ala Leu Glu Thr Val Gln Arg Leu Leu Pro
            1620                1625                1630

Val Leu Cys Gln Asp His Gly Leu Thr Pro Asp Gln Val Val Ala Ile
            1635                1640                1645

Ala Ser His Asp Gly Gly Lys Gln Ala Leu Glu Thr Val Gln Arg Leu
            1650                1655                1660

Leu Pro Val Leu Cys Gln Asp His Gly Leu Thr Pro Asp Gln Val Val
1665                1670                1675                1680

Ala Ile Ala Ser Asn Lys Gly Gly Lys Gln Ala Leu Glu Ser Ile Val
            1685                1690                1695

Ala Gln Leu Ser Arg Pro Asp Pro Ala Leu Ala Ala Leu Thr Asn Asp
            1700                1705                1710

His Leu Val Ala Leu Ala Cys Leu Gly Gly Arg Pro Ala Met Asp Ala
            1715                1720                1725

Val Lys Lys Gly Leu Pro His Ala Pro Glu Leu Ile Arg Arg Val Asn
            1730                1735                1740

Arg Arg Ile Gly Glu Arg Thr Ser His Arg Val Ala Arg Ser Gln Leu
1745                1750                1755                1760

Val Lys Ser Glu Leu Glu Glu Lys Lys Ser Glu Leu Arg His Lys Leu
            1765                1770                1775

Lys Tyr Val Pro His Glu Tyr Ile Glu Leu Ile Glu Ile Ala Arg Asn
            1780                1785                1790

Ser Thr Gln Asp Arg Ile Leu Glu Met Lys Val Met Glu Phe Phe Met
            1795                1800                1805

Lys Val Tyr Gly Tyr Arg Gly Lys His Leu Gly Gly Ser Arg Lys Pro
            1810                1815                1820

Asp Gly Ala Ile Tyr Thr Val Gly Ser Pro Ile Asp Tyr Gly Val Ile
1825                1830                1835                1840

Val Asp Thr Lys Ala Tyr Ser Gly Gly Tyr Asn Leu Pro Ile Gly Gln
            1845                1850                1855

Ala Asp Glu Met Glu Arg Tyr Val Glu Glu Asn Gln Thr Arg Asn Lys
            1860                1865                1870
```

His Leu Asn Pro Asn Glu Trp Trp Lys Val Tyr Pro Ser Ser Val Thr
            1875                1880                1885

Glu Phe Lys Phe Leu Phe Val Ser Gly His Lys Gly Asn Tyr Lys
    1890                1895                1900

Ala Gln Leu Thr Arg Leu Asn His Ile Thr Asn Cys Asn Gly Ala Val
1905                1910                1915                1920

Leu Ser Val Glu Glu Leu Leu Ile Gly Gly Glu Met Ile Lys Ala Gly
            1925                1930                1935

Thr Leu Thr Leu Glu Glu Val Arg Arg Lys Phe Asn Asn Gly Glu Ile
            1940                1945                1950

Asn Phe

<210> SEQ ID NO 13
<211> LENGTH: 53
<212> TYPE: DNA
<213> ORGANISM: Artificial Sequence
<220> FEATURE:
<223> OTHER INFORMATION: target sequence in TaMLO

<400> SEQUENCE: 13
tcgctgctgc tcgccgtgac gcaggacccc atctccggga tatgcatctc cga      53

<210> SEQ ID NO 14
<211> LENGTH: 53
<212> TYPE: DNA
<213> ORGANISM: Artificial Sequence
<220> FEATURE:
<223> OTHER INFORMATION: binding site

<400> SEQUENCE: 14
tcgctgctgc tcgccgtcac gcaggaccca atctccggga tatgcatctc cca      53

<210> SEQ ID NO 15
<211> LENGTH: 53
<212> TYPE: DNA
<213> ORGANISM: Artificial Sequence
<220> FEATURE:
<223> OTHER INFORMATION: Binding site

<400> SEQUENCE: 15
tcgctgctgc tcgccgtgac gcaggacccc atctccggga tatgcatctc cga      53

<210> SEQ ID NO 16
<211> LENGTH: 53
<212> TYPE: DNA
<213> ORGANISM: Artificial Sequence
<220> FEATURE:
<223> OTHER INFORMATION: Binding site

<400> SEQUENCE: 16
tcgctgctgc tcgccgtgac gcaggaccca atctccggga tatgcatctc cga      53

<210> SEQ ID NO 17
<211> LENGTH: 23
<212> TYPE: DNA
<213> ORGANISM: Artificial Sequence
<220> FEATURE:
<223> OTHER INFORMATION: target sequence in TaMLO-A1

<400> SEQUENCE: 17
ccgtcacgca ggacccaatc tcc      23

<210> SEQ ID NO 18

```
<211> LENGTH: 32
<212> TYPE: DNA
<213> ORGANISM: Artificial Sequence
<220> FEATURE:
<223> OTHER INFORMATION: primer

<400> SEQUENCE: 18
tggcgctggt cttcgccgtc atgatcatcg tc                                    32

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
tacgatgagc gccaccttgc ccgggaa                                          27

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
ataagctcgg ccatgtaagt tccttcccgg                                       30

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
ccggccggaa tttgtttgtg tttttgtt                                         28

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
tggcttcctc tgctcccttg gtgcacct                                         28

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
tggagctggt gcaagctgcc cgtggacatt                                       30

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
```
gtcttcgccg tcatgatcat cgtctcc                                              27

<210> SEQ ID NO 25
<211> LENGTH: 28
<212> TYPE: DNA
<213> ORGANISM: Artificial Sequence
<220> FEATURE:
<223> OTHER INFORMATION: Primer

<400> SEQUENCE: 25
tggtattcca aggaggcggt ctctgtct                                             28

<210> SEQ ID NO 26
<211> LENGTH: 23
<212> TYPE: DNA
<213> ORGANISM: Artificial Sequence
<220> FEATURE:
<223> OTHER INFORMATION: Binding site

<400> SEQUENCE: 26
cttggagatt gggtcctgcg tga                                                  23

<210> SEQ ID NO 27
<211> LENGTH: 23
<212> TYPE: DNA
<213> ORGANISM: Artificial Sequence
<220> FEATURE:
<223> OTHER INFORMATION: Binding site

<400> SEQUENCE: 27
aaactcacgc aggacccaat ctc                                                  23

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
gtcttcgccg tcatgatcat cgtctcc                                              27

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ggtgctcagg tagtggttgt c                                                    21

<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30
ctttgtcgtg aatataaacc agacacgag                                            29

<210> SEQ ID NO 31
<211> LENGTH: 28
<212> TYPE: DNA

```
<213> ORGANISM: Artificial Sequence
<220> FEATURE:
<223> OTHER INFORMATION: Primer

<400> SEQUENCE: 31
tggtattcca aggaggcggt ctctgtct                                              28

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
cagttagaca tggtctaaag gacaattgag                                            30

<210> SEQ ID NO 33
<211> LENGTH: 27
<212> TYPE: DNA
<213> ORGANISM: Artificial Sequence
<220> FEATURE:
<223> OTHER INFORMATION: Primer

<400> SEQUENCE: 33
ccaaccacac cacatcatca caaccaa                                               27

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
tgatgatgat gatgatggaa cttgttctcg                                            30

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
aaggaggcgg tctctgtctc ccatttcttc                                            30

<210> SEQ ID NO 36
<211> LENGTH: 26
<212> TYPE: DNA
<213> ORGANISM: Artificial Sequence
<220> FEATURE:
<223> OTHER INFORMATION: Primer

<400> SEQUENCE: 36
ttcatctcgc tgctgctcca tctccg                                                26

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
agccatgatg atgacgctgt aggtgacatg                                            30
```

<210> SEQ ID NO 38
<211> LENGTH: 2809
<212> TYPE: DNA
<213> ORGANISM: Artificial Sequence
<220> FEATURE:
<223> OTHER INFORMATION: Tamlo-A

<400> SEQUENCE: 38

| | | | | | |
|---|---|---|---|---|---|
| atggcggagg | acgacgggta | ccccccggcg | cggacgctgc | cggagacgcc | gtcctgggcg | 60 |
| gtggcgctgg | tcttcgccgt | catgatcatc | gtctccgtcc | tcctggagca | cgcgctccac | 120 |
| aagctcggcc | atgtaagtcc | cctcactccc | gcaacaagaa | caagaacaag | aacaagaaca | 180 |
| accagaacca | gaatcagctc | atggcttcct | ttcctccctt | ggtgcgtgta | agcagtggtt | 240 |
| ccacaagcgg | cacaagaacg | cgctggcgga | ggcgctggag | aagatgaagg | cggagctgat | 300 |
| gctggtggga | ttcatctcgc | tgctgctcgc | cgtcacgcga | aggtgaccgc | ggtgatgatg | 360 |
| atgatgatgg | aacttgttct | cgcccgtggt | gacccaatct | ccgggatatg | catctcccag | 420 |
| aaggccgcca | gcatcatgcg | ccctgcaag | gtggaacccg | gttccgtcaa | gagcaagtac | 480 |
| aaggactact | actgcgccaa | agaggtaact | aacacaaaca | gtttcttctt | cttcttgttg | 540 |
| ttttccttcc | tgattggctt | ggcctgattg | gtgtggtgtc | tgtttctcct | gcagggcaag | 600 |
| gtggcgctca | tgtccacggg | cagcctgcac | cagctccaca | tattcatctt | cgtgctagcc | 660 |
| gtcttccatg | tcacctacag | cgtcatcatc | atggctctaa | gccgtctcaa | ggtgagcctt | 720 |
| tcttctttc | tttcccgtgc | ttccagatcc | tgcgcggttc | ccgggcaagg | tggcgctcat | 780 |
| cgtacgtctg | tctcagttaa | actgctacca | atccttaacc | tgctccggca | taatattctt | 840 |
| attcctcccc | ccggcagatg | agaacatgga | agaaatggga | gacagagacc | gcctccttgg | 900 |
| aataccagtt | cgcaaatggt | cagacaattt | tccaaatgaa | acctcttctg | ttttgatgcg | 960 |
| tttacagagg | caggcatgat | cagagcgagt | gaactgatga | tatgttcttc | tctttcccgt | 1020 |
| gcttccagat | cctgcgcggt | tccgcttcac | gcaccagacg | tcgttcgtga | agcggcacct | 1080 |
| gggcctgtcc | agcaccccg | gcgtcagatg | ggtggtggcc | ttcttcaggc | agttcttcag | 1140 |
| gtcggtcacc | aaggtggact | acctcaccttt | gagggcaggc | ttcatcaacg | tacgtaatac | 1200 |
| cccaaaagcc | ccctctcctt | ctagctccgt | cggccattgc | cgcgacgctt | ctgaaataag | 1260 |
| tactgttcca | acaccaatga | tcacatgctc | tctctttcca | tgattctgcg | caggcgcact | 1320 |
| tgtcgcagaa | cagcaagttc | gacttccaca | agtacatcaa | gaggtccatg | gaggacgact | 1380 |
| tcaaagtcgt | cgttggcatc | aggtaggttg | cattccatgg | atatgattat | acaattgtcg | 1440 |
| tcaggctcca | tatgatattg | cttagcttcc | atatgataca | atactatcag | tttgctgcgt | 1500 |
| catggtcttt | gccctgctg | gtccttgttg | catgatcttg | acacatttgg | cctcttttcg | 1560 |
| cagcctcccg | ctgtgggctg | tggcgatcct | caccctcttc | cttgatatcg | acggtatgga | 1620 |
| ccttgtcttt | gccccttct | ctgttgcctt | gctgctaaaa | cacttgtaat | ttatttgtct | 1680 |
| cgtaaccacc | gttcattttc | taacctttcc | cccctttctt | tctgctcata | gggatcggca | 1740 |
| cactcacctg | gtttctttc | atccctctca | tcgtaagtgc | gaatttctcc | gccgaaagca | 1800 |
| acagccaaac | cccatttgat | tgcaatgcga | atcacacct | aataataatt | caaattgtca | 1860 |
| ttgtccatct | gtctttccca | gatcctcttg | tgtgttggaa | ccaagctaga | gatgatcatc | 1920 |
| atggagatgg | ccctggagat | ccaggaccgg | tcgagcgtca | tcaaggggc | acccgtggtc | 1980 |
| gagcccagca | acaagttctt | ctggttccac | cgccccgact | gggtcctctt | cttcatacac | 2040 |

```
ctgacgctgt tccagaacgc gtttcagatg gcacatttcg tgtggacagt ggtacgccgc   2100
ggatgaactt gtcagttaat aatatgggtg tcaaggcacc aagtgctgct gctgatgaac   2160
tgcactgaca gagatttacc tgtgtcgcag gccacgcccg gcttgaagga ctgcttccat   2220
atgaacatcg ggctgagcat catgaaggtc gtgctggggc tggctctcca gttcctgtgc   2280
agctacatca ccttcccccct ctacgcgcta gtcacacagg taataaaacc gttgatgaag   2340
atctctgaac aattgctctg ggagaggaga aacagcagcc ttaatcatct gtgtgcgctg   2400
gctttgtacg cagatgggat caaacatgaa gaggtccatc ttcgacgagc agacagccaa   2460
ggcgctgacc aactggcgga acacggccaa ggagaagaag aaggtccgag acacggacat   2520
gctgatggcg cagatgatcg gcgacgcaac acccagccga ggcacgtccc cgatgcctag   2580
ccggggctca tcgccggtgc acctgcttca gaagggcatg ggacggtctg acgatcccca   2640
gagcgcaccg acctcgccaa ggaccatgga ggaggctagg gacatgtacc cggttgtggt   2700
ggcgcatcct gtacacagac taaatcctgc tgacaggaga aggtcggtct cttcatcagc   2760
cctcgatgcc gacatcccca gcgcagattt ttccttcagc cagggatga               2809

<210> SEQ ID NO 39
<211> LENGTH: 2675
<212> TYPE: DNA
<213> ORGANISM: Artificial Sequence
<220> FEATURE:
<223> OTHER INFORMATION: Tamlo-D1

<400> SEQUENCE: 39
atggcggagg acgacgggta cccccccggcg cggacgctgc cggagacgcc gtcctgggcg     60
gtggcgctcg tcttcgccgt catgatcatc gtgtccgtcc tcctggagca cgcgctccac    120
aagctcggcc atgtaagttc cctcactcct gcaacaagaa aaaaaaaagc ctcaaccaga    180
atcagcagct cagctcatgg cttcctctgc tcccttggtg cacctgcagt ggttccacaa    240
gcggcacaag aacgcgctgg cggaggcgct ggagaagatc aaagcggagc tgatgctggt    300
ggggttcatc tcgctgctgc tccatctccg agaaggccgc cagcatcatg cggccctgca    360
gcctgccccc tggttccgtc aagagcaagt acaaagacta ctactgcgcc aaaaaggtga    420
gcctgctaca agctactccc ggagacggcc gggaaaaaca caaacagatt ccggcggccg    480
gccggagttt cttcttgttt ccttcctgat tggcttggcc taattggtgt gtgtttttct    540
ggcagggcaa ggtgtcgcta atgtccacgg gcagcttgca ccagctccac atattcatct    600
tcgtgctcgc cgtcttccat gtcacctaca gcgtcatcat catggctcta agccgtctca    660
aagtgagtct gtcaggccta cctgttcatg cttcggtaaa gcaataaaac tacttgctac    720
caatccctaa tctgctccct caggcataat attgttcctt ctttcctgct gcagatgagg    780
acatggaaga aatgggagac agagaccgcc tccttggaat accagttcgc aaatggtcag    840
acaatttccg aaatgaaacc tgactgatgc atttacaaac gcacgcaggc aggcatgatc    900
agagtgagtg aactgatgat atgttttctc tctctttccc gtgcctccag atcctgcgcg    960
gttccgcttc acgcaccaga cgtcgttcgt gaagcgtcac ctgggcctct ccagcacccc   1020
cggcatcaga tgggtggtgg ccttcttcag gcagttcttc aggtcggtca ccaaggtgga   1080
ctacctcacc ctgagggcag gcttcatcaa cgtacgtacc aaaacaaatc ctctccctct   1140
agcttcgcca ttgctgcgac gcttctgaaa tatgtaccgt tccgacacca gcgatctcat   1200
gtcttctctt tccacgattc tgcgcaggcg catttgtcgc ataacagcaa gttcgacttc   1260
cacaagtaca tcaagaggtc catggaggac gacttcaaag tcgtcgttgg catcaggtag   1320
```

-continued

```
gttacattcc atggatagga ttataaaatt gccgtcaggc tccatatgat attgcttagg    1380
ttccacatga tacaatacta tcagtttgct gcgtcatggt ctttgcccct gctggtcttc    1440
cttgcgtgat cttgacacat ttggcctctt ttcgcagcct cccgctgtgg tgtgtggcga    1500
tcctcaccct cttccttgat attgacggta tggaccttgc taaaacactt gtaatttgtc    1560
tcgtaaccac cgttcatttt ctaaccttcc tttccccttc tttctgctgg cagggatcgg    1620
cacgctcacc tggatttctt tcatccctct cgtcgtaagt gcgaatttct ccgccgaaag    1680
caacagccag ccccatttga ttgcaatgcg aaaccacacc ttaattgaaa atgtcattgt    1740
ctgtcttgtc tttctcagat cctcttgtgt gttggaacca agctggagat gatcatcatg    1800
gagatggccc tggagatcca ggaccgggcg agcgtcatca aggggcgcc  cgtggttgag    1860 cccagcaaca agttcttctg gttccaccgc cccgactggg tcctcttctt catacacctg    1920
acgctgttcc agaatgcgtt tcagatggca catttcgtct ggacagtggt atgtaccagt    1980
aattggcagt tcagttaggg atgcaaggca ccaagtagtg ctgatgaact gcactgacgg    2040
agatttactt gttcgtaggc cacgcccggc ttgaagaaat gcttccatat gcacatcggg    2100
ctgagcatca tgaaggtcgt gctggggctg gctcttcagt tcctctgcag ctatatcacc    2160
ttcccgctct acgcgctcgt cacacaggta ataaagccgt tgatgaagat gtctgaacaa    2220
ttgctctggg agaggagaaa cagcagcctt aatcatgtaa tcggtgtgat gggttgcaga    2280
tgggatcaaa catgaagagg tccatcttcg acgagcagac ggccaaggcg ctgacaaact    2340
ggcggaacac ggccaaggag aagaagaagg tccgagacac ggacatgctg atggcgcaga    2400
tgatcggcga cgcgacgccc agccgagggg cgtcgcccat gcctagccgg ggctcgtcgc    2460
cagtgcacct gcttcacaag ggcatgggac ggtccgacga tccccagagc acgccaacct    2520
cgccaagggc catggaggag gctagggaca tgtacccggt tgtggtggcg catccagtgc    2580
acagactaaa tcctgctgac aggagaaggt cggtctcttc gtcggcactc gatgccgaca    2640
tccccagcgc agattttcc ttcagccagg gatga                               2675
```

<210> SEQ ID NO 40
<211> LENGTH: 3003
<212> TYPE: DNA
<213> ORGANISM: Artificial Sequence
<220> FEATURE:
<223> OTHER INFORMATION: Tamlo-R32-A upstream sequence

<400> SEQUENCE: 40

```
gtgcgccact gctatatagc agtggcgcac caccatcatg gtgcgccact aatagggata     60
ttggctatag ccattttct  agtagtgtaa gcacaagaaa taaaaaaaat atggaaaacc    120
ctcacatctc atcttaaatt ctcagagtta gtaatacgaa attcaacgca aatcagggag    180
taggacaacg agacgaaagt gattcccccg tagctctttt atttcgcgag ggctctgatc    240
atgtatagct agccatgcat agacaacatg acaggcatgt tttgggtgcc cacagcacac    300
acaagttgtg aaacagtacg tgcatgactg ggcacagagc aggttagagc aaacctccac    360
atcaccataa attccgagta gccactagat tcagcatgcc tgtttagggt tctgtacagt    420
acgtacctgg ctactactgc ttgccaattg aaaaatgatt tagagcaaat tccagaatgc    480
catgacacat ctgcttttat gtcaaaccca ctgttcataa caatatttgt gcggtggtgt    540
gcatgagata agatccggat gagggtggcg cccataaaaa atgggccatt catgaaccag    600
cagcgtcaac acgaacgagc gacgaagccg cgggctacga gcgtcaccac acaatatgtt    660
```

```
aatggatcgg gccggccatc ccatcggcca tcagggtgtg ctgccaagca gatctccatg      720
catgatgcat cacgggtgca cctagtagcc acatagatct ccagactcca ggcatgatgc      780 atcacggggtg catctgtata ttcaaaccta ccattaactt tgcccgatca gaggaaccgg     840
tccggatccg atcgttaatt cggcgaccag tgacttgatc gcgtctgttt aagcactagc      900
agctcactga tcgcatggat cgaccgctgg taagaatagt acaccctgtg catatacaag      960
tccgcgaaaa agtagcagcc acgaatgcag tcaacgtttt tatttgacct gactcgctcg     1020
atcaggcccg tactccactg gttgaaacgc ccacttcgcc ggagccgcct ggtcagactt     1080
ttccacgcac gaccgaccat tgagcagtca aagttcggat gccacgccgt cgctcgcatg     1140
cggacgtacg tgtgcaagtc gtcgcaactt gcgtgctaca gaaattcaaa acaaaacaaa     1200
aaaacttgcg tggcacagta cgagactaca agcgagtaga agcgcaccac gtatgcccgt     1260
gtatctgcag taacggaacc gtgcacgttt tggctaaacg tgcgcatgca gcagggtgca     1320
cgtccacgtc ctgcaggttt aagtatataa tgtagcttac agtaattaac catgcatgct     1380
tcgaaatgaa gcactgcctg ccgggcgccg gcgacctgat ccaccaccac ccgacgcgcg     1440
gctcgccggc gggaacagcc agtcgcgcgc gtggacctct cgcctctacc aacgtgtggc     1500
tacgtgtaac cgtgctccgt aaaaccgtgt tggttttacc tttaccttc tctcgcccgc      1560 acacacgtcg ccgccaagac atgcgtcgcg tcattttctc caaataactt tggcgcgaac     1620
gggtctccga tcgagcagca ccaaatcaat caacccaacg aaagtgatcc gacgtcacaa     1680
aattcgatcc cccgagaaac tggcagcact tttgccgttt tcttgccggt cccaacgaac     1740
tctccgtccc tcctaattta atgtcaaaaa aatataaaaa aatctccgcc tgcgttgatg     1800
atcccaataa ccagcaagct gtcctacggg atcattcagg agcttttaga gctgctactt     1860
gtcatctctt tgatggaatc gccgattcgg aggttgctga aatttatgcc tgcaaacgag     1920
ctttataggt ggcggccgaa ctcaacacat ccaagctgtt gttggagacg gactgtgcta     1980
atctagcaaa gatgttgtgt gcgcaagaga aaactctctc tgcatttgga cctctggtga     2040
aggagatcaa ggagaggatg aaaatgttcc aagaagtgaa aatgtcttgc gtaaggcgta     2100
gtgctaatgc tgccgcggat aagttagcta aagttgggtt aagtgataga ctgtgtaagg     2160
tttggtttgc cgttccccca gattgtattc tgggcattgt gtcggacgag attcctaatt     2220
tcatttaatt agtcaataaa gcggcagtag ttgatcctca aaaaaaataa ccagcaagct     2280
agccggacgc gtcggttttt gtcctgccta agctaggagt atctccaagt aacctacgcg     2340
ggacaaaact atggccagat agacactagt caaacgatcg caacaagaaa aaaactagtc     2400
aagaaaaata ctacagatta cctaaagaaa aaaatagaa aaccaaaaca aaaatactgg      2460
taaagtgacc gtccccgtca aaaaatactt gccgaccgac cgggtgtccc ccgtcgcccc    2520
ggcccggtgc cggccgagca cccgcccag agcgccatca ctggatcaac caccccgtcc     2580
aaccgcgcgc tacgaaacat cggtcgtttc tcacggtgca atctcagccg gaaaccggcg    2640
ctcgcgcgca tcagctgtag cctgtaggtc tcgggctccg cagcgccgct gccgagccac    2700
ccggccggcg cgcacgcacg cacgcgcttt gacccggccg ccgataaaag gccccgcgcg    2760
gcagctccct cctacccggt tgccacaccc acagtctgcc acagcagcaa caagctagac     2820
atacctgcgt gcgtacgtac gttttcgttt tcctttcttg ctccggccgg ccggccggcc    2880
acgtagaata gatacctgcc caggtacgta cctcgttggc tcagacgatc ggcggttgga    2940
cttgggtgcg cgccctgccc tgctccggcc aaggaaagag gttgcgctaa agacgggcgg    3000
atg                                                                  3003
```

<210> SEQ ID NO 41
<211> LENGTH: 3458
<212> TYPE: DNA
<213> ORGANISM: Artificial Sequence
<220> FEATURE:
<223> OTHER INFORMATION: Tamlo-R32-B upstream sequence

<400> SEQUENCE: 41

| | | | | | | |
|---|---|---|---|---|---|---|
| ccccgtagct | cttttatttc | gcgagggctt | tgatcatgta | tagctagcca | taaacaacat | 60 |
| gacaggcatg | ttttgggtgc | ccacagcaca | cacaagttgt | gaaacagtac | gtacatgact | 120 |
| gggcacagag | caggttagag | gaaacctcca | catcatcata | aattctgagg | agccactaga | 180 |
| ttcagcatgt | ctgtttaggg | ttctggctac | ttgccaataa | aaaaatatta | tgatttacta | 240 |
| gcatagattc | cagaatgcca | tgacatttct | gctttgattt | caatccactg | ctcataacag | 300 |
| aagcatatgg | cccggactca | ttaacttggt | cgttcctcat | gatttgttct | agtctcgttt | 360 |
| tatctcacaa | gatgcttgtt | cacaaggttg | tcagaatcgc | gattctgaat | cggatcggag | 420 |
| ctccaatggc | aggatcacaa | atcatagaat | cttcactatc | aggatcgtga | aaacgtagat | 480 |
| tctatgaacc | aaaatcataa | aatcagaggg | gttagtttga | atcgtaaaat | cgtagaatcg | 540 |
| tacaacataa | tcgcgattct | gacaaccttg | cttgttcatt | tgctgctata | tatattagga | 600 |
| ccatgcatat | tggtcacacg | agggcagcgc | tgcaagtgca | aagtcgccga | gacaagactg | 660 |
| agcaccgttt | catgggcttg | atctcttggt | aagcagccgc | cgccggacca | tcatcagcca | 720 |
| agaaagacac | attcttgtgc | tactatattt | gtgcggttgc | gcgcatgaga | taagatccgg | 780 |
| atgaggatgg | cgcgcataaa | aaaatgagca | atgtcaaagc | agtgtaccct | gagcttcctt | 840 |
| ccattcatga | accagtagcg | tcaactacag | gaacgagcaa | cgaaccgtca | ccttatatta | 900 |
| gtggatcggg | cccatccatc | ccatcagggt | gtgccgtcaa | gcagatctcc | atgcatgcat | 960 |
| ctcggattgc | acctagtagc | cacataaaca | gaggctgatt | agtactacta | caaaggtacc | 1020 |
| ggctaggcca | aatcatctcg | cctcgttgaa | attcaaacct | gccattaact | ttccccgatc | 1080 |
| agaagaaacg | gtccggatcc | gatcgttaat | tcggcgacca | gtgacttgat | ctcgtccgtt | 1140 |
| taagcactat | actagcagca | gatcactgat | cacatggatg | gaccgctgct | aagaatagta | 1200 |
| tatccttcct | gcatatacaa | gtccgcaaaa | aagtagcagc | cacacaaatg | cagtcaacgc | 1260 |
| tccatttgac | ttgacccgct | ccatcaggcc | cgtactccac | tggttgaaac | gcccacttcg | 1320 |
| ccggagcggc | gtggtcgact | tctccacgca | ggggaccgac | catgagcagt | caaacttggg | 1380 |
| atgccacgtc | gaccgacgtg | tgcaagtcgt | cgcaacttgc | ttggcacagt | acgagaccac | 1440 |
| aagcgagcag | gagtgcgcca | cgtatacgtg | acgggcccgt | ttgcctgcag | tgacggaacc | 1500 |
| gtgcacgctt | tggctaaata | taaacgtgcg | catgcagcag | ggcttacaag | aaccattaag | 1560 |
| taactttcac | gtccacgtcg | tacagtacat | gtttatatat | aacgtcgtaa | actacagtta | 1620 |
| gcgcatgctc | tagcggcata | cggtgccagc | cgactgatgg | tccggcaagt | ttgggctgat | 1680 |
| gacctacctg | atgatgtaaa | cgttcagatg | gccagcgttt | tgcctgcgcc | cgtgtgattt | 1740 |
| atggaatctg | ggtgttccat | ttaaaaaaaa | aaacccattc | atgcttcgaa | atgaagcatg | 1800 |
| gaggaagtcg | gacgtcacac | aattcgatcg | atcgacccat | cgttttctc | ggccggggaa | 1860 |
| gaggcaaggc | gggcacagtt | ttgccctttt | cgatcgtttg | gtccgtccca | acagattctc | 1920 |
| cgtccccatt | aatcaagtcc | aaaacaggaa | tacatgcagc | aatactctat | gcttgtccaa | 1980 |
| ttagcaatta | ctctcacgtc | aaccgctggc | gattaacaat | ggctctccgt | atgaaaaact | 2040 |

```
aactcgatgg gagcaccagg ctagccatcg tgcacgcacg tcccggccgg tgaatgtttc    2100
gaccgtctgg gtacgagccc gacccgctcg aaggtgccac gccccctgcct accaggcgcc    2160 ggcgacctga tccaccaccc gacgcgcggc tcgccggcgg aacagtcag tcgcgttgac    2220 ctctcgcctc taccaacgtg tggctacgtg taaccgtggt ccgtaaaccc gtgttcgttt    2280
taccttacct ttctcacgcg cacaatacat gtttcgcgtc attttctcca cgtaaaactt    2340
tggcgcgaac gggtctccga tcgagcagca tcaaatcaat caacccaacg aaagtgatcc    2400
gacgtcacac aattcgattc cccaagaaac ggggcagcac atttgccgtt tccttgccgg    2460
tccaacgaac tctccgtcct aatttaacgt cagttttttt tctccgcccg cgttgatgat    2520
cccgataacc agcaagctag ccagacgcgt cggcttttgt cctgcttagc taggagtatc    2580
tccaagtaac cttacctacg cgggacaaaa ctatggccag atatagatat actagtcaaa    2640
cgatggcaac aagaacaaaa aaaaactact ccctccgctt ctaaatataa gttttttctag    2700 agattttact ataaactata tacgacgta tatagacaaa atttaagtgt atattcactt    2760
attttgctct gtatgtagtt ttttgttgga atctctaaaa agaaatatag gagtatttag    2820
gaacagaggg agtagtcaag aataatacta cggattccct aaaggaaaaa atagaaaaaa    2880
aatactacta gtattttttg agaaataata ctacaagtaa agtgaccgtc tctgtcagaa    2940
aatactacgg gaccgaccgg gtgttccccc tcgccccggc ccggtgccgg ccgagcaccc    3000
agagtgccat cactggatca accaccccgt ccaacctcgc gctaggaaac atagctcgat    3060
ccctcaaaca aaaaaaaaaa ggaaacatag ctcgtatcag ccgaaacccg ccactcgaca    3120
ttcgtatcag ctctaggcag gtctcccgct ccgcagcgcg ccgctgccga gccaccggc    3180 cggcgcgcag gcgcgcacgc acgcggtttg accggccgc cgcgcgcccg cgccgcgccg    3240
ataaaaggcc ccgcgcggca gctccctccc acccggttgc cacgcccaca cttcgccaac    3300
acacaacgta cctgcgtacg tacgcttttcc atttcctttc ttgctccggc cggccggcca    3360
cgtagaatag atacccggcc aggtaggtac ctcgttggct cagacgaccg gcggctgggt    3420
ctccggacaa ggaaagaggt tgcgctcggg gaccgatg                           3458
```

<210> SEQ ID NO 42
<211> LENGTH: 2997
<212> TYPE: DNA
<213> ORGANISM: Artificial Sequence
<220> FEATURE:
<223> OTHER INFORMATION: Tamlo-R32-D upstream sequence

<400> SEQUENCE: 42

```
gagggaaatg ttttagaact gggcgagggc ccggactcat taacttggct gttcctcatg      60
atctgttctt gtctcgtttt atctcaggag atgcttgttc atttgttgct atataatact     120
tcctccgttc ggaattactt gtcgcagaaa tggatgtatc tagacatatt ttaattttag     180
atacattcat tttcgagaca agtaattccg aatggaggga gtacccatgc atattcgtct     240
cacgagggca gcgctgcaaa tgcaaagtct cgccgagaca agaccggtca cccttttcat     300
gagcttgatc tcttggtaag cagccccgc cggaccatca taataacttc ataagccggg     360
aaagacccat ttgtggtacg tactaatact atatttgtgc ggttgtgcgc atgagataag     420
atccggttga gggtggcgcg cataaaaaat gggctatgtc aaagcaatat cccctgagcc     480
tccatccatg aaccagtagc gtccgtcaac tacacgaacg agcgacgagg ccgcgcgcta     540
cgagcgccac catatacgta cgtatatatt agtggatcgg gccattagca taagatctcc     600
atgcatgcat gtcggatagt acatctcgaa atagtctttc gccccgcttt atctcggatg     660
```

```
cacctagtag ccacatagac aggccaaatc atcgcttgct aaaagaactg agctagtagt    720
agtactggca tctcttgatg tgcctcgttg aaattcaaac cgaccattaa ctttccccga    780
tcagaggaac cggtccggat ccgatcgtta gttcggcgac gggcgacttg atcccgtctg    840
tttaagcact agtagtagca gatcactcat cacatggacg gaccgctgct aataattaat    900
agtatacctg cctgctgtgc atatacaagt cctggtaaaa gtagcagcca cacaaatgca    960
gtcaacgctt cgtttgactt gactcgctca ggcccgtagc cgtactccac tggatctgga   1020
tggaacgccc gcttcgccgg agctgcctgg tcagacttct ccacgcacgc acgaccgacc   1080
atgggcagtc aaacttcgga tgccacgtcg acgtccacgt tgtcggtcgc atgcggacgt   1140
gcgtgtgcag gtcgtcgcaa cttgcgtggt acagtacgag actactccgt acaagcgagt   1200
agaagtgcac cacgtatacg tgccgggccc gtttacctgc agtaacggaa ccgtgcacgc   1260
tttggctata cgtgcgcatg cagcaggctg cacgtcgatg ccgtgcaggt tttataatgt   1320
aggagtatac tgtaactacc ttacaattaa taaccatgga tggatgcttc gaaatgaagc   1380
atggaggaag cccgacgtca cacagttcga tcgcccgatc cctcgttttt cccggccggg   1440
gaagagacaa gagaaacaga gctttgccct tttcgatcgt ctggtctgtc caacagact   1500 ctccgtcctc attaatcaag tccaaaacag gaatacatgc agcaatactg tatgcttgcc   1560
aaattagcaa tcactatcac gtcaaccggg ggcgattaac aatggcccct ccgtatgaaa   1620
aactaactcg atgggagcac caggctagcc atcgtacacg cacgtcccgg ccggtgaatg   1680
tttcgaccgt ctgggtacga gtctgacccg ctcgaaggtg ccacgcccct gcctgccggg   1740
cgccggcgac ctgatccacc accacccgac gcgcggctcg ccagcgggaa cagtcagtcg   1800
cgcgcgtgga cggcgagtct cgcctctacc aacgtgtggc tacgtgtaac cgtgctccgt   1860
aaaaccgtgt tcgttttacc ttacctttct cgcgcgcaca cacgtcgccg ccaatacatg   1920
tttcgcgtca ttttctccac gcaataactt tggcgcgaac gggtctccga tcgagcggca   1980
tcaaatcaat caacccaaca aaagtgatcc gacgtcacac aattcgatcc cccaagaaac   2040
ggggcagcac atttgccgtt ttcttgccgg tcccaacgaa ctctccgtcc taatttaacg   2100
tcagtttttt ttctccgccc gcgttgatga tcccgataac gagcaagcta gccagacgcg   2160 tcggttttg tcctgcctag ctaggagtat ctccaagtaa cctacctacg cgggacaaaa   2220
ctatggccag atatagatat actagtcaaa cgatggcaac aagaaaaaaa actagtcaag   2280
aataatactc cctccattct aaattacttg tcgcaggtat gaatgtatct agatgtattt   2340
tagttctaga tacatccatt tctgcaacga gtaatttgaa acggagggag tactacggat   2400
tccctaaaga aaaaaatact actaaaaact agtactagta gtaaagtgac cgtccccatc   2460
aagaaatact acgggaccga ccgggtgtcc ccctcgccc cggccggtg ccggccgagc   2520 acccagagcg ccatcgctgg atcaaccacc ccgtccaacc tcgcgctagg aaacataggt   2580
cgtttcagcc gaaacccgcc actcgacatt cgtatcagct ctaggcaggt ctcccgctcc   2640
gcagcgccgc tgccgagcca cccggccggc gcgcaggcct aggtttgacc cggccgccgg   2700
gcgcccggcc gataaaaggc cccgcgcggc agctccctcc cacccggttg ccacgcacac   2760
acttcgccac agcagaaaca agctagacac acaacgtacc tgcgtacgta cgcttccctt   2820
ctccttgctt gctccggccg gccggccacg tagaatagat acctggccag gtaggtacct   2880
cgttggctca gacgatcggt ggttgggctc gggcgcgcgc ctgtccggct gaggtggccg   2940
ccgttcgctc cggccaagga aagaggttgt gctcaggacg ggcggcgggg agccatg     2997
```

<210> SEQ ID NO 43
<211> LENGTH: 53
<212> TYPE: DNA
<213> ORGANISM: Artificial Sequence
<220> FEATURE:
<223> OTHER INFORMATION: TaMLO-A1

<400> SEQUENCE: 43
tcgctgctgc tcgccgtcac gcaggaccca atctccggga tatgcatctc cca          53

<210> SEQ ID NO 44
<211> LENGTH: 53
<212> TYPE: DNA
<213> ORGANISM: Artificial Sequence
<220> FEATURE:
<223> OTHER INFORMATION: TaMLO-B1

<400> SEQUENCE: 44
tcgctgctgc tcgccgtgac gcaggacccc atctccggga tatgcatctc cga          53

<210> SEQ ID NO 45
<211> LENGTH: 53
<212> TYPE: DNA
<213> ORGANISM: Artificial Sequence
<220> FEATURE:
<223> OTHER INFORMATION: TaMLO-D1

<400> SEQUENCE: 45
tcgctgctgc tcgccgtgac gcaggaccca atctccggga tatgcatctc cga          53

<210> SEQ ID NO 46
<211> LENGTH: 41
<212> TYPE: DNA
<213> ORGANISM: Artificial Sequence
<220> FEATURE:
<223> OTHER INFORMATION: MLO-A1 alignment

<400> SEQUENCE: 46
tgctcgccgt cacgcaggac ccaatctccg ggatatgcat c                       41

<210> SEQ ID NO 47
<211> LENGTH: 53
<212> TYPE: DNA
<213> ORGANISM: Artificial Sequence
<220> FEATURE:
<223> OTHER INFORMATION: MLO-B1 alignment

<400> SEQUENCE: 47
tcgctgctgc tcgccgtcac gcacgacccc atctccggga tatgcatctc cga          53

<210> SEQ ID NO 48
<211> LENGTH: 53
<212> TYPE: DNA
<213> ORGANISM: Artificial Sequence
<220> FEATURE:
<223> OTHER INFORMATION: MLO-D1 alignment

<400> SEQUENCE: 48
tcgctgctgc tcgccgtgac gcaggaccca atctccggga tatgcatctc cga          53

<210> SEQ ID NO 49
<211> LENGTH: 1606
<212> TYPE: DNA
<213> ORGANISM: Artificial Sequence
<220> FEATURE:
<223> OTHER INFORMATION: GFP donor cassette

<400> SEQUENCE: 49

```
tcgctgctgc tcgccgtgac gcaggacccc atctccggga tatgcatctc cgaaagcttg      60
tcgacggatc catggtgagc aagggcgagg agctgttcac cggggtggtg cccatcctgg     120
tcgagctgga cggcgacgta aacgccaca agttcagcgt gtccggcgag ggcgagggcg      180
atgccaccta cggcaagctg accctgaagt tcatctgcac caccggcaag ctgcccgtgc     240
cctggcccac cctcgtgacc accttcacct acggcgtgca gtgcttcagc cgctaccccg     300
accacatgaa gcagcacgac ttcttcaagt ccgccatgcc cgaaggctac gtccaggagc     360
gcaccatctt cttcaaggac gacggcaact acaagacccg cgccgaggtg aagttcgagg     420
gcgacaccct ggtgaaccgc atcgagctga agggcatcga cttcaaggag gacggcaaca     480
tcctggggca caagctggag tacaactaca acagccacaa cgtctatatc atggccgaca     540
agcagaagaa cggcatcaag gtgaacttca gatccgcca caacatcgag gacggcagcg      600
tgcagctcgc cgaccactac cagcagaaca cccccatcgg cgacggcccc gtgctgctgc     660
ccgacaacca ctacctgagc acccagtccg ccctgagcaa agaccccaac gagaagcgcg     720
atcacatggt cctgctggag ttcgtgaccg ccgccgggat cactcacggc atggacgagc     780
tgtacaagta accgggcgag ctcgaattcg ctgaaatcac cagtctctct ctacaaatct     840
atctctctct attttctcca taaataatgt gtgagtagtt tcccgataag ggaaattagg     900
gttcttatag ggtttcgctc atgtgttgag catataagaa acccttagta tgtatttgta     960
tttgtaaaat acttctatca ataaaatttc taattcctaa aaccaaaatc cagtactaaa    1020
atccagatct cctaaagtcc ctatagatct ttgtcgtgaa tataaaccag acacgagacg    1080
actaaacctg gagcccagac gccgttcgaa gctagaagta ccgcttaggc aggaggccgt    1140
tagggaaaag atgctaaggc agggttggtt acgttgactc ccccgtaggt ttggtttaaa    1200
tatgatgaag tggacggaag gaaggaggaa gacaaggaag gataaggttg caggccctgt    1260
gcaaggtaag aagatggaaa tttgatagag gtacgctact atacttatac tatacgctaa    1320
gggaatgctt gtatttatac cctataccc ctaataaccc cttatcaatt taagaaataa     1380
tccgcataag cccccgctta aaattggta tcagagccat gaataggtct atgaccaaaa     1440
ctcaagagga taaaccctca ccaaaatacg aaagagttct taactctaaa gataaaagat    1500
cttttcaagat caaaactagt tccctcacac cggtgacggg gatcgcatgc gattcgctgc    1560
tgctcgccgt gacgcaggac cccatctccg ggatatgcat ctccga                   1606
```

<210> SEQ ID NO 50
<211> LENGTH: 32
<212> TYPE: PRT
<213> ORGANISM: Artificial Sequence
<220> FEATURE:
<223> OTHER INFORMATION: Binding site

<400> SEQUENCE: 50

```
His Asp Asn Asn His Asp Asn Gly Asn Asn His Asp Asn Gly Asn Asn
1               5                   10                  15
His Asp Asn Gly His Asp Asn Asn His Asp His Asp Asn Asn Asn Gly
            20                  25                  30
```

<210> SEQ ID NO 51
<211> LENGTH: 34
<212> TYPE: PRT
<213> ORGANISM: Artificial Sequence
<220> FEATURE:

```
<223> OTHER INFORMATION: Binding site

<400> SEQUENCE: 51

His Asp Asn Asn Asn Asn Ile Asn Asn Asn Ile Asn Gly Asn Asn
1               5                   10                  15

His Asp Asn Ile Asn Gly Asn Ile Asn Gly His Asp His Asp His Asp
            20                  25                  30

Asn Asn
```

WHEAT PLANTS RESISTANT TO POWDERY MILDEW

CROSS-REFERENCE TO RELATED APPLICATIONS

This application is the U.S. National phase application corresponding to PCT/GB2016/052149 which was assigned an international filing date of Jul. 15, 2016 and associated with publication WO 2017013409 A2 and which claims priority to PCT/CN2015/084370 filed on Jul. 17, 2015, the disclosures of which are expressly incorporated herein by reference.

FIELD OF THE INVENTION

The present invention relates to conferring pathogen resistance in wheat plants.

INTRODUCTION

In plants, resistance to pathogens is frequently triggered by a recognition event followed by a coordinated complex defence response resulting in localized containment of the intruder.

Powdery mildew (Pm) is one of the most important cereal diseases worldwide. The powdery mildew disease, caused by obligate biotrophic ascomycete fungi of the order Erysiphales, is a major impediment for cereal (e.g. wheat and barley) agriculture in temperate climates. Powdery mildew in wheat is caused by the infection of Blumeria graminis f. sp. tritici (Bgt) (also called Erysiphe graminis f. sp. tritici).

MLO proteins function as negative regulators of plant defence to powdery mildew disease[25]. Loss-of-function mlo alleles in barley[26,40] Arabidopsis[27] and tomato[28] lead to broad-spectrum and durable resistance to the fungal pathogen causing powdery mildew.

Resistance responses to the powdery mildew pathogen have been genetically well characterized. In most analyzed cases resistance is specified by race-specific resistance genes following the rules of Flor's gene-for-gene hypothesis. In this type of plant-pathogen interactions, resistance is specified by and dependent on the presence of two complementary genes, one from the host and one from the fungal pathogen. The complementary genes have been termed operationally (pathogen) resistance ("R") gene and avirulence ("Avr") gene, respectively. Most of the powdery mildew resistance genes (Mlx) act as dominant or semidominant traits.

However, monogenic resistance mediated by recessive (mlo) alleles of the Mlo locus is different. Apart from being recessive, it differs from race-specific resistance to single pathogen strains in that it confers broad spectrum resistance to almost all known isolates of the pathogen and mlo resistance alleles exhibit a defence mimic phenotype in the absence of the pathogen. Thus, the genetic data indicate that the Mlo wild type allele exerts a negative regulatory function on defence responses to pathogen attack (WO98/04586).

Bread wheat (Triticum aestivum L., 2n=42, AABBDD) is a major staple crop worldwide and provides about 20% of all calories consumed by humans. Because of its economic importance, new traits have always been sought to improve yield, quality and adaptation to biotic and abiotic stresses, mostly through classical breeding. Bread wheat is an allohexaploid, with three similar but not identical copies of most of its genes[5]. Its large genome (17,000 megabases), high ploidy level and high content of repetitive DNA (80% to 90%) make it one of the most challenging species for forward and reverse genetics studies[6].

In wheat, powdery mildew is caused by Blumeria graminis f. sp. tritici (Bgt), and is one of the most destructive diseases worldwide. Modification of MLO genes in wheat may provide the opportunity to breed varieties with broad-spectrum and durable resistance to Bgt. In bread wheat, there are three MLO homoeologs (TaMLO-A1, TaMLO-B1 and TaMLO-D1), which are 98% and 99% identical at the nucleotide and protein levels, respectively[29]. TaMLO-B1 can rescue the resistance of a barley mlo mutant to powdery mildew disease, indicating that the function of these MLO genes has been conserved during evolution[29]. However, to date, no spontaneous or and induced mlo mutants have been reported in bread wheat, probably because of its hexaploid nature and the inherent difficulty in mutating all three MLO homoeoalleles. Moreover, no successful progress has been made with transgenic approaches to downregulating MLO in wheat. Broad spectrum resistance to powdery mildew is a resistance trait that has not been found in the natural wheat population[4]. Therefore, there is a significant need to develop wheat genotypes that are resistant to Pm.

Recently, genome editing techniques have emerged as alternative methods to conventional mutagenesis methods (such as physical and chemical mutagenesis) or methods using the expression of transgenes in plants to produce mutant plants with improved phenotypes that are important in agriculture. These techniques employ sequence-specific nucleases (SSNs)[1] including zinc finger nucleases (ZFNs)[7], rare-cutting endonucleases, for example transcription activator-like effector nucleases (TALENs[2]), and the RNA-guided nuclease Cas9 (CRISPR/Cas9)[41,38,3], which generate targeted DNA double-strand breaks (DSBs), which are then repaired mainly by either error-prone non-homologous end joining (NHEJ)[8] or high-fidelity homologous recombination (HR)[1,9]. The SSNs have been used to create targeted knock-out plants in various species ranging from the model plants, Arabidopsis[10,11] and tobacco[12], to important crops, such as barley[13,14], soybean[15], rice[16-21] and maize[22,23]. Heritable gene modification has been demonstrated in Arabidopsis[10,11,24] and rice[18] using the CRISPR/Cas9 system and TALENs. Genome editing of a single MLO gene in bread wheat using a transient protoplast expression system[17] has been demonstrated and it has been shown that introducing mutations in the coding region of all three MLO homoeoalleles in wheat confers heritable resistance to powdery mildew fungus[43]. However, the inventors have found that these mutants also show detrimental development related phenotypes compared to wild type plants when grown under disease free conditions.

The invention described herein is thus aimed at providing alternative mutant wheat plants resistant to powdery mildew and related methods which do not show detrimental development related phenotypes compared to wild type plants when grown under disease free conditions, thus providing products and methods of agricultural importance.

SUMMARY OF THE INVENTION

The inventors have generated mutant wheat lines with mutations inactivating all three MLO homoeoalleles which confer heritable resistance to powdery mildew fungus. These plants do not show senescence like phenotypes which negatively impact on crop yield and quality under non-disease conditions. Thus, the invention relates to these mutant wheat lines and related methods.

In particular, in a first aspect, the invention relates to a wheat plant, plant part or plant cell that has increased resistance to powdery mildew compared to a wild type wheat plant and comparable yield under non-disease conditions compared to a wild type wheat plant wherein said plant comprises a loss of function mutation in the coding regions of two alleles selected from TaMLO-A1, TaMLO-B1 and TaMLO-D1 and reduced expression of the third TaMLO allele.

In another aspect, the invention relates to a wheat plant, plant part of plant cell that has increased resistance to powdery mildew compared to a wild type plant comprising a loss of function mutation in the coding regions of two alleles selected from TaMLO-A1, TaMLO-B1 and TaMLO-D1 and reduced expression of the third TaMLO allele wherein said third TaMLO allele does not have a mutation in its coding region.

In one specific aspect, the invention relates to a wheat plant, plant part or plant cell that has increased resistance to powdery mildew compared to a wild type wheat plant and comparable yield under non-disease conditions compared to a wild type wheat plant wherein said plant comprises a loss of function mutation in the coding regions of TaMLO-A1 and TaMLO-D1 and reduced expression of TaMLO-B1 wherein the coding region of TaMLO-B1 does not contain a mutation as compared to the coding region of TaMLO-B1 from a wild type plant.

In one specific aspect, the invention relates to a wheat plant, plant part or plant cell that has increased resistance to powdery mildew compared to a wild type wheat plant and comparable yield under non-disease conditions compared to a wild type wheat plant comprising a Tamlo-a sequence as shown in SEQ ID No. 38, a Tamlo-d sequence as shown in SEQ ID No. 39 and a TaMLO-B1 sequence having a wild type sequence of SEQ ID NO. 2.

In another specific aspect, the invention relates to a wheat plant, plant part or plant cell or part thereof wherein said wheat genotype has the CGMCC Accession Number 10951.

In another aspect, the invention relates to a method for producing a wheat plant, plant part or plant cell with increased resistance to powdery mildew compared to a wild type plant and comparable yield under non-disease conditions compared to a wild type wheat plant using targeted genome modification comprising introducing a loss of function mutation into the coding regions of two MLO alleles selected from TaMLO-A1, TaMLO-B1 and TaMLO-D1 and decreasing expression of the third TaMLO allele.

In another aspect, the invention relates to a plant, plant part or plant cell obtained or obtainable by this method.

DESCRIPTION OF FIGURES

The invention is further illustrated in the following non-limiting figures.

FIG. 5. DNA sequence of the GFP donor cassette. The cassette contains the GFP coding sequence (in bold) and the CaMV 35S terminator sequence (in italics), and is flanked by two T-MLO target sequences (underlined) at both ends.

FIG. 6. Vector sequences. (A-1, A2) The sequence of UBI-attr1-attr2-Nos in vector pYP010: 4047 bp. The sequence of Ubi-1 is underlined is and the attr1 and attr2 are in italics. Nos is indicated in bold. (SEQ ID NO. 7) (b) The sequence of TAL-L in vector pZHY500: 2202 bp. The sequences of N terminal and C terminal are underlined. TAL-L is labelled in bold. (SEQ ID NO. 8) (C-1, C-2) The sequence of TAL-R in vector pZHY501: 2304 bp. The sequences of N terminal and C terminal are indicated. TAL-R is labelled in bold. (SEQ ID NO. 9) (D-1, D-2, D-3, D-4) The sequence of TALENs (TAL-L+TAL-R) in vector pZHY013. Sequences in italics are attr1 and attr2. The sequences of N terminal and C terminal parts are indicated underlined. TAL-L and TAL-R are in bold. The FokI sequences are in italics and underlined. T2A motif is underlined and in bold. (SEQ ID NO.10).

FIG. 7. Genetic mapping.

DETAILED DESCRIPTION

Figure 1:
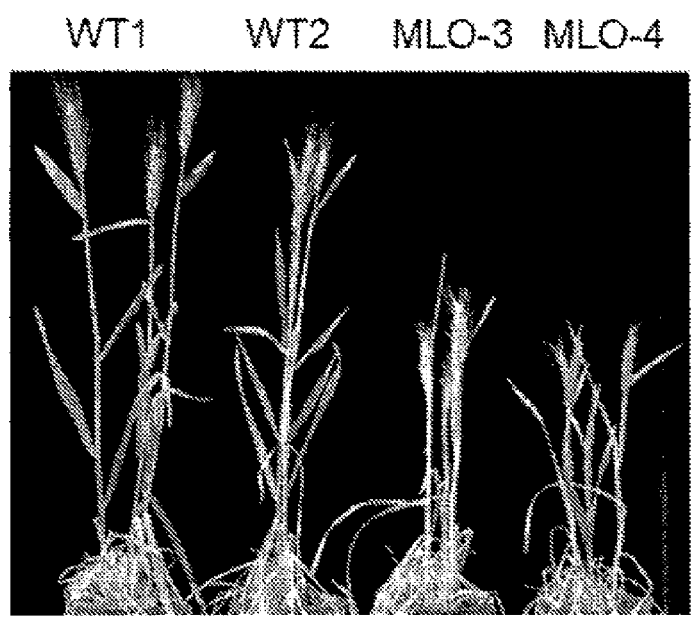
FIG. 1. TaMLO homologous triple mutants When TaMLO homologous triple mutants[42] (tamlo-aabbdd) were grown under axenic (disease free) conditions, these triple mutant plants show development related phenotypes, including cell death and senescence-like chlorosis about at 12 weeks.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene", "allele" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences. Thus, according to the various aspects of the invention, genomic DNA, cDNA or coding DNA may be used. In one embodiment, the nucleic acid is cDNA or coding DNA.

The terms "peptide", "polypeptide" and "protein" are used interchangeably herein and refer to amino acids in a polymeric form of any length, linked together by peptide bonds.

The term "allele" designates any of one or more alternative forms of a gene at a particular locus. Heterozygous alleles are two different alleles at the same locus. Homozygous alleles are two identical alleles at a particular locus. A wild type allele is a naturally occurring allele.

For the purposes of the invention, a "mutant" plant is a plant that has been altered compared to the naturally occurring wild type (WT) plant. Specifically, the endogenous nucleic acid sequences of each of the MLO homologs in wheat (wild type nucleic acid sequences TaMLO-A1, TaMLO-B1 and TaMLO-D1) have been altered compared to wild type sequences using mutagenesis methods as described herein. This causes inactivation of the endogenous Mlo genes and thus disables Mlo function. Such plants have an altered phenotype and show resistance or increased resistance to Pm compared to wild type plants. Therefore, the resistance is conferred by the presence of mutated endogenous TaMLO-A1, TaMLO-B1 and TaMLO-D1 genes in the wheat plant genome which has been specifically targeted using targeted genome modification and is not conferred by the presence of transgenes expressed in wheat.

As used herein, wild type nucleic acid sequences of wild type alleles are designated using capital letters, that is TaMLO-A1, TaMLO-B1 and TaMLO-D1. Mutant mlo nucleic acid sequences use non-capitalisation, that is tamlo-aa1, tamlo-bb1, tamlo-dd1. Wheat plants of the invention are mutant plants compared to wild type plants which comprise and express mutant mlo alleles.

mlo mutations that down-regulate or disrupt functional expression of the wild-type Mlo sequence are recessive, such that they are complemented by expression of a wild-type sequence. Thus "Mlo function" can be determined by assessing the level of constitutive defence response and/or susceptibility of the plant to a pathogen such as, for example, powdery mildew. Thus, according to the invention, a putative nucleotide sequence with Mlo function can be tested upon complementation of a suitable mlo mutant. The term "mlo function" is used to refer to sequences which confer a mlo mutant phenotype on a plant. The capitalisation of "Mlo" and non-capitalisation of "mlo" is thus used to differentiate between "wild-type and mutant" function.

A mlo mutant phenotype according to the invention is characterised by the exhibition of an increased resistance against Pm. In other words, a mlo mutant according to the invention confers resistance to the pathogen causing Pm. Moreover, the mutant according to the invention is characterised in that it does not show any negative phenotype compared to the wild type which impacts on crop yield and quality, when grown under disease free conditions. In other words, the mutants of the invention do not show any yield and quality penalties compared to a wild type (wt) plant when grown under disease free conditions.

A negative phenotype compared to the wild type which impacts on crop yield and quality includes senescence-like phenotypes, reduced growth or reduced seed yield compared to a wild type plant. Senescence-like phenotypes can be assessed through the appearance of chlorosis. The reduction can be 1%, 2%, 3%, 4%, 5%, 6%, 7%, 8%, 9%, 10% or more.

A wild type wheat plant is a plant that does not have any mutant Mlo alleles.

The aspects of the invention involve targeted mutagenesis methods, specifically genome editing, and exclude embodiments that are solely based on generating plants by traditional breeding methods. As explained herein, the disease resistant trait is not due to the presence of a transgene.

The inventors have generated mutant wheat lines with mutations inactivating all three MLO homoeoalleles which confer heritable resistance to powdery mildew fungus so that no functional TaMLO-B1, TaMLO-A1 or TaMLO-D1 protein is made. These plants do not show senescence like phenotypes which negatively impact on crop yield and quality. Thus, the invention relates to these mutant wheat lines and related methods.

As shown in FIG. 1, when TaMLO homologous triple mutants[42] (genotype: tamlo-aabbdd) were grown under axenic (disease free) conditions, these triple mutant plants show development related phenotypes, including cell death and senescence-like chlorosis at about 12 weeks. These phenotypes also occurred, as previously reported, in barley[42] and *Arabidopsis*[44]. The senescence-like phenotypes may negatively influence wheat crop yield and quality.

However, in wheat mlo mutants generated using TALENs, we identified one line, Tamlo-R (with genetic profile tamlo-AaBBDd), which is heterozygous in genome A and D, but which does not have a mutation at the target site in genome B in T0 plants (FIG. 2). After segregation, in the T1 generation, we identified 7 plants homozygous for the mutation in genome A and D (tamlo-aaBBdd), named as R4, R25, R26, R32, R40, R51 and R54. When all the 7 homozygous T1 plants were challenged with conidiospores of a virulent Bgt race, we found that only the homozygous plant R32 confers resistance to powdery mildew (FIG. 2). Interestingly, R32 did not display the senescence-like chlorosis, and the plant grew as vigorously as the wild type in disease free conditions.

Figure 3:
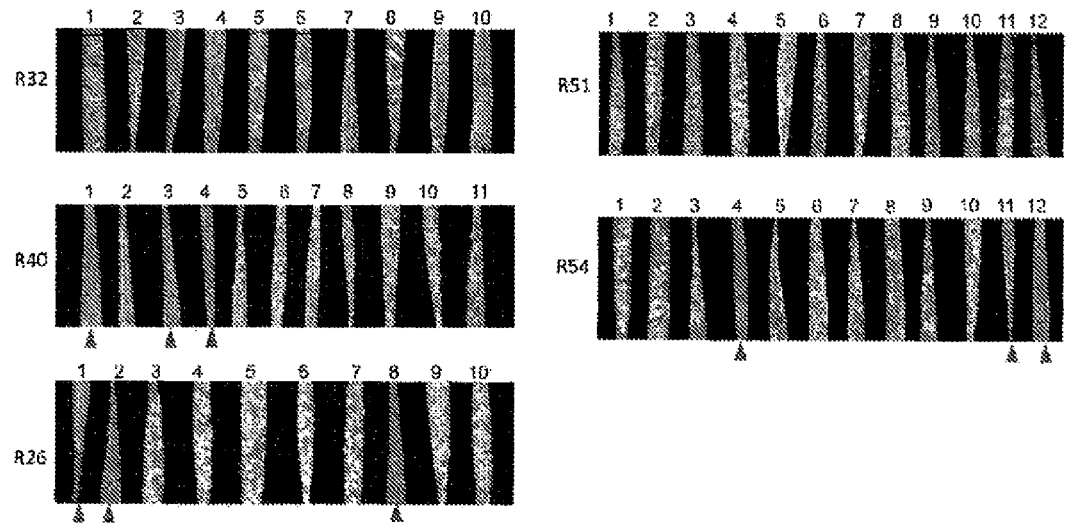
FIG. 3. Phenotype of homozygous T1 mutant lines. All the progeny of R32 showed resistance to Bgt, and about ⅓ of R26, R40 and R54 offsprings were resistant to the Bgt. All the progeny of R51 were susceptible to the Bgt. In contrast to fully resistant mutant tamlo-aabbdd plants, the resistant mutant plants allow the low-level growth of sporulating Bgh.

We also assessed the resistance to powdery mildew of offspring of all the homozygous mutant progeny of line Tamlo-R (R4, R25, R26, R32, R40, R51 and R54). We found that all the progeny of R32 showed resistance to Bgt, and about ⅓ of R26, R40 and R54 offspring were resistant to the Bgt. All the progeny of R51 were susceptible to the Bgt (FIG. 3). In contrast to fully resistant mutant tamlo-aabbdd plants, the resistant mutant plants allow the low-level growth of sporulating Bgh (FIG. 3.). This phenotype was similar to the well-known and widely used (in agriculture) barley mlo mutant mlo-11[42]. None of these powdery mildew resistant mutant plants showed developmentally related negative phenotypes, such as cell death or senescence-like chlorosis.

Figure 4:
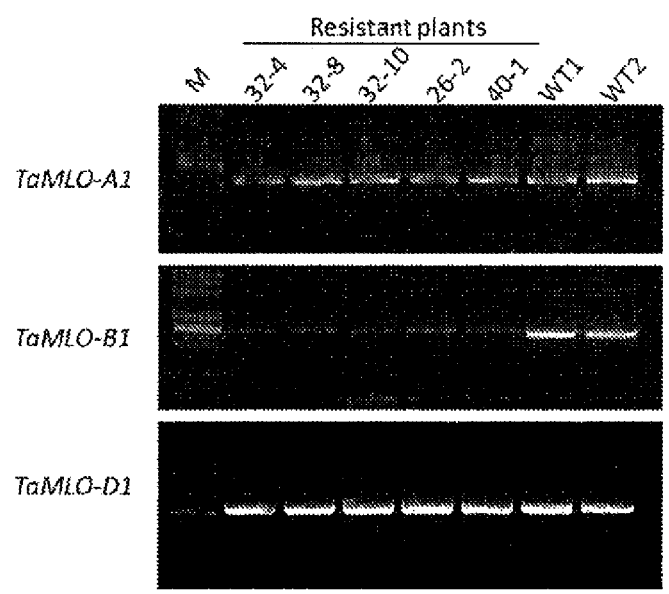
FIG. 4. Transcription level of mlo in mutant lines. Transcription of the TaMLO protein of genome B (TaMLO-B1) of these resistant plants is lower compared with wild type.

We assessed the level of transcription of mlo for these mutants in genome A, B and D, respectively. We found that the transcription of the TaMLO protein of genome B (TaMLO-B1) of these resistant plants was lower compared with wild type (FIG. 4). This result is also similar to that described in barley mutant mlo-11[42]. Accumulation of both Mlo-B transcript and protein is impaired in the R32 line, but the mutation does not reside in the coding region of TaMLO-B1.

Thus, the invention relates to a wheat plant, plant part or plant cell generated by genome editing techniques which has increased resistance to powdery mildew compared to a wild type what plant and which does not show growth or yield penalties under non-disease conditions compared to a wild type plant. Compared to fully resistant mutant tamlo-aabbdd plants, such plant shows better growth and/or yield under non-disease conditions. Thus, yield of the plants of the invention is comparable to the yield of wild type plants under non-disease conditions, that is where the plant is not exposed to powdery mildew. This means that there is essentially no reduction in yield or no more than 1-5% reduction in yield.

Specifically, in a first aspect, the invention relates to a wheat plant, plant part or plant cell that has increased resistance to powdery mildew compared to a wild type plant and comparable yield under non-disease conditions compared to a wild type wheat plant wherein said plant comprises a loss of function mutation in the coding regions of two alleles selected from TaMLO-A1, TaMLO-B1 and TaMLO-D1 and reduced expression of the third TaMLO allele or inactivated function of the third TaMLO protein.

In one embodiment, the coding region of said third TaMLO allele does not contain a mutation as compared to the coding region of the TaMLO allele from a wild type plant.

In one embodiment, the coding region of said third TaMLO allele does not contain a mutation as compared to the coding region of TaMLO allele from a wild type plant that renders the protein non-functional or reduces gene expression.

For example, the third TaMLO allele may comprise a mutation that reduces expression of the third TaMLO allele or inactivates function of the third third TaMLO protein wherein said mutation is not in the coding region of said third TaMLO allele.

In another aspect, the invention relates to a wheat plant, plant part of plant cell that has increased resistance to powdery mildew compared to a wild type plant comprising a loss of function mutation in the coding regions of two alleles selected from TaMLO-A1, TaMLO-B1 and TaMLO-D1 and reduced expression of the third TaMLO allele wherein said third TaMLO allele does not have a mutation in its coding region.

In one embodiment, the invention relates to a wheat plant, plant part or plant cell wherein said plant comprises a loss of function mutation in the coding regions of TaMLO-A1 and TaMLO-D1 and reduced expression of TaMLO-B1 wherein the coding region of TaMLO-B1 does not contain a mutation as compared to the coding region of TaMLO-B1 from a wild type plant.

The loss of function mutations in the two MLO alleles result in impaired transcript and/or protein accumulation. Expression of the third TaMLO allele is reduced compared to wild type expression, for example by at least 5-50%. In one embodiment, there is essentially no expression. A mutation that reduces expression of or otherwise inactivates the third TaMLO allele does not reside in the coding region of said allele, but results in impaired accumulation of the transcript of the third TaMLO allele and/or impaired accumulation of the protein encoded by the third TaMLO allele. For example, the mutation may be in the regulatory region of the allele (for example in SEQ ID No. 40, 41 or 42 or 5' thereof). Alternatively, the mutation that inactivates the third TaMLO allele can be a mutation found in another gene in the pathway which interacts with said TaMLO allele, or due to epigenetic factors affecting the sequence of regulatory region. Thus, said reduced expression of the TaMLO allele, for example TaMLO-B1, is caused by a mutation in the regulatory region of the TaMLO allele, for example TaMLO-B1, a mutation in a gene downstream in the MLO pathogen response pathway or is due to an epigenetic factor.

Thus, the mutant wheat plant according to the invention is a triple mutant and comprises a genotype selected from tamlo-aaBBdd, tamlo-aabbDD or tamlo-AAbbdd. The triple mutants do not have a mutation in the coding region in one of the TaMLO alleles selected from TaMLO-A1, TaMLO-B1 and TaMLO-D1. Thus, the mutation cannot be found in an exon of said TaMLO allele.

The mutations are introduced into the wild type TaMLO alleles using targeted genome modification, preferably they are introduced simultaneously.

In one embodiment, said targeted genome modification comprises the use of SSNs. These may be selected from ZFNs, a rare-cutting endonuclease, for example a TALEN or CRISPR/Cas9.

Rare-cutting endonucleases are naturally or engineered proteins having endonuclease activity. These bind to nucleic acid target sequences which have a recognition sequence typically 12-40 bp in length. In one embodiment, the SSN is selected from a TALEN. In another embodiment, the SSN is selected from CRISPR/Cas9. This is described in more detail below.

The loss of function mutation may be a deletion or insertion ("indels") with reference the wild type TaMLO-A1, TaMLO-B1 and TaMLO-D1 allele sequence are shown herein. The deletion may comprise 1-20, for example 1, 2, 3, 4, 5, 6, 7, 8, 9, 10, 1, 12, 13, 14, 15, 16, 17, 18 or 20 nucleotides in one or more strand. The insertion may comprise 1-20, for example 1, 2, 3, 4, 5, 6, 7, 8, 9, 10, 1, 12, 13, 14, 15, 16, 17, 18 or 20 nucleotides in one or more strand.

The plant of the invention includes plants wherein said plant is heterozygous for the each of the mutations. In a preferred embodiment however, said plant is homozygous for the mutations. Progeny that is also homozyous can be generated from these plants according to methods known in the art.

According to the various aspects of the invention, the wild type TaMLO-A1 allele comprises or consists of SEQ ID NO. 1 or a fragment or a functional variant thereof. The corresponding amino acid sequence is SEQ ID NO. 4. According to the various aspects of the invention, the wild type TaMLO-B1 allele comprises or consists of SEQ ID NO. 2 or a fragment or a functional variant thereof. The corresponding amino acid sequence is SEQ ID NO. 5. According to the various aspects of the invention, the wild type TaMLO-D1 allele comprises or consists of SEQ ID NO. 3 or a fragment or a functional variant thereof. The corresponding amino acid sequence is SEQ ID NO. 6.

The term "functional variant of a nucleic acid or protein sequence" as used herein, for example with reference to SEQ ID NOs: 1, 2 or 3 refers to a variant gene sequence or part of the gene sequence which retains the biological function of the full non-variant TaMLO allele and hence act to modulate responses to Pm. A functional variant also comprises a variant of the gene of interest encoding a polypeptide which has sequence alterations that do not affect function of the resulting protein, for example in non-conserved residues. Also encompassed is a variant that is substantially identical, i.e. has only some sequence variations, for example in non-conserved residues, to the wild type nucleic acid sequences of the alleles as shown herein and is biologically active.

As used herein, variants of a particular TaMLO nucleotide or amino acid sequence according to the various aspects of the invention will have at least about 50%-99%, for example at least 75%, for example at least 85%, 86%, 87%, 88%, 89%, 90%, 92%, 94%, 95%, 96%, 97%, 98% or 99% or more sequence identity to that particular non-variant TaMLO nucleotide sequence of the TaMLO allele as shown in SEQ ID NO. 1, 2 or 3 or 4, 5 or 6. Sequence alignment programs to determine sequence identity are well known in the art.

Also, the various aspects of the invention the aspects of the invention encompass not only a TaMLO nucleic acid sequence, but also fragment thereofs. By "fragment" is intended a portion of the nucleotide sequence or a portion of the amino acid sequence and hence of the protein encoded thereby. Fragments of a nucleotide sequence may encode protein fragments that retain the biological activity of the native protein and hence act to modulate responses to Pm.

In one embodiment, said mutation is introduced using a TALEN and wherein said TAL effector binds to a sequence in exon 2. In one embodiment, said TAL effector binds to TCGCTGCTGCTCGCCGTgacgcaggacccatctcCGGGA-TATGCATCTCCGA (SEQ ID NO. 13).

Specifically, the binding site sequences of the second exon conserved region TaMLO-A, TaMLO-B and TaMLO-D to which these TALENs bind are:

```
                                          (SEQ ID NO. 14)
MLO-A:TCGCTGCTGCTCGCCGTcacgcaggacccaatctcCGGGATATG
CATCTCCCA (SEQ ID NO. 15)
MLO-B:TCGCTGCTGCTCGCCGTgacgcaggacccatctcCGGGATATG
CATCTCCGA (SEQ ID NO. 16)
MLO-D:TCGCTGCTGCTCGCCGTgacgcaggacccaatctcCGGGATATG
CATCTCCGA
```

The three SNPs are in bold and underlined. The AvaII restriction site is shown in small letters and underlined.

A TALEN pair has for example the nucleic acid sequence SEQ ID NO. 11. The corresponding amino acid sequence is SEQ ID NO. 12.

In one embodiment, the plant of the invention comprises the mutations in TaMLO-A1 and/or TaMLO-D1 as shown in FIG. 1. In one embodiment, the mutations are as shown for tamlo-aaBBdd. In other words, in said wheat plant, the endogenous TaMLO-A1 allele is a mutant Tamlo-a1 allele and comprises SEQ ID NO. 38 the endogenous TaMLO-B1 allele is a wild type TaMLO-B1 allele and comprises SEQ ID NO. 2, and the endogenous TaMLO-D1 allele is a mutant Tamlo-d1 allele and comprises SEQ ID NO. 39.

In one aspect, the mutant plant is TALEN free.

The wheat plant is selected from the list that includes, but is not limited to, *Triticum aestivum, T. aethiopicum, T. araraticum, T. boeoticum, T. carthlicum, T. compactum, T. dicoccoides, T. dicoccum, T. durum, T. ispahanicum, T. karamyschevii, T. macha, T. militinae, T. monococcum, T. polonicum, T. repens, T. spelta, T. sphaerococcum, T. timopheevii, T. turanicum, T. turgidum, T. urartu, T. vavilovii* and *T. zhukovskyi*.

According to another embodiment the various aspects of the invention described herein, the plant is of the species *Triticum aestivum* or *Triticum turgidum*. According to another preferred embodiment, the plant belongs to the cultivar Bobwhite or the cultivar Don Pedro. More preferably, the cultivars BW208 and BW2003 (Bobwhite), which belong to the wheat species *Triticum aestivum* L. ssp *aestivum*, and the variety Don Pedro, which belongs to the wheat species *Triticum turgidum* L. ssp *durum*, are selected.

Bobwhite is the name of the cultivar obtained from the International Maize and Wheat Improvement Center (CIM-MYT). BW208 and BW2003 are different Bobwhite lines. Don Pedro is a hard wheat variety, also from CIMMYT.

In particular, the invention relates to a mutant wheat genotype (*Triticum aestivum*), designated Accession Number CGMCC 10951 deposited under the Budapest Treaty at the China General Microbiological Culture Collection Center, Institute of Microbiology, Chinese Academy of Sciences, No. 1 Beichen West Road, Chaoyang District, Beijing 100101 on 29 Jun. 2015 by The Institute of Genetics and Developmental Biology Chinese Academy of Sciences, No. 1 Beichen West Road, Chaoyang District, Beijing 100101. The depositor's reference is Tamlo-R32. The deposited material was found viable in a test performed on 6 Jul. 2015. The invention thus relates to any what plants, parts thereof, including seeds, having this genotype. This mutant is described herein as Tamlo-aaBBdd (FIG. 1).

A triple mutant wheat plant according to the invention shows resistance or increased resistance to Pm compared to a control plant, preferably a wild type plant, because the mutations in impair accumulation of the TaMLO allele transcript and/or protein. The wheat plant according to the invention shows increased yield compared to a wild type control plant under biotic stress conditions wherein said stress is Pm.

Resistance can for example be assessed by assessing survival, growth, yield or size of pathogen colonies.

The terms "increase", "improve" or "enhance" are interchangeable. Yield for example is increased by at least a 3%, 4%, 5%, 6%, 7%, 8%, 9% or 10%, preferably at least 15% or 20%, more preferably 25%, 30%, 35%, 40% or 50% or more in comparison to a control plant. The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" of a plant may relate to vegetative biomass (root and/or shoot biomass), to reproductive organs, and/or to propagules (such as seeds) of that plant. Thus, according to the invention, yield comprises one or more of and can be measured by assessing one or more of: increased seed yield per plant, increased seed filling rate, increased number of filled seeds, increased harvest index, increased number of seed capsules and/or pods, increased seed size, increased growth or increased branching, for example inflorescences with more branches. Preferably, yield comprises an increased number of seed capsules/pods and/or increased branching. Yield is increased relative to control plants.

A control plant as used herein is a plant, which has not been modified according to the methods of the invention. Accordingly, the control plant does not have a mutant tamlo nucleic acid sequence as described herein. In one embodiment, the control plant is a wild type wheat plant. In another embodiment, the control plant is a plant that does not have a mutant tamlo nucleic acid sequence as described here, but is otherwise modified. The control plant is typically of the same plant species, preferably the same ecotype or the same or similar genetic background as the plant to be assessed.

The term "plant" as used herein encompasses whole plants, ancestors and progeny of the plants and plant parts, including seeds, fruit, shoots, stems, leaves, roots (including tubers), flowers, and tissues and organs, wherein each of the aforementioned comprise the gene/nucleic acid of interest. The term "plant" also encompasses plant cells, suspension cultures, protoplasts, callus tissue, embryos, meristematic regions, gametophytes, sporophytes, pollen and microspores, again wherein each of the aforementioned comprises the gene/nucleic acid of interest.

The invention also extends to harvestable parts of a mutant plant of the invention as described above such as, but not limited to seeds, leaves, flowers, stems and roots. The invention furthermore relates to products derived, preferably directly derived, from a harvestable part of such a plant, such as dry pellets or powders, oil, fat and fatty acids, flour, starch or proteins. The invention also relates to food products and food supplements comprising the plant of the invention or parts thereof.

In one aspect, the invention relates to a seed of a mutant wheat plant of the invention. Seeds harvested from a mutant plant that is homozygous for the mlo mutations are preferred.

In another embodiment, the present invention provides a regenerable mutant plant as described herein cells for use in tissue culture. The tissue culture will preferably be capable of regenerating plants having essentially all of the physiological and morphological characteristics of the foregoing mutant wheat plant, and of regenerating plants having substantially the same genotype. Preferably, the regenerable cells in such tissue cultures will be callus, protoplasts, meristematic cells, cotyledons, hypocotyl, leaves, pollen, embryos, roots, root tips, anthers, pistils, shoots, stems, petiole, flowers, and seeds. Still further, the present invention provides wheat plants regenerated from the tissue cultures of the invention.

In a preferred embodiment, the mutant wheat plants are produced by simultaneous editing of the target M/o sequences.

The invention also relates to an isolated nucleic acid sequence as defined in SEQ ID NO. 38 or 39. Also within scope of the invention are vectors comprising such sequences and host cells comprising such sequences or such vector.

Method for Producing Plants

In another aspect, the invention relates to a method for producing a wheat plant, plant part of plant cell resistant to powdery mildew compared to a wild type wheat plant and comparable yield under non-disease conditions compared to a wild type wheat plant using targeted genome modification comprising introducing a loss of function mutation into the coding regions of two TaMLO alleles selected from TaMLO-A1, TaMLO-B1 and TaMLO-D1 and reducing expression of the third TaMLO allele. For example, a mutation that reduces expression of the third TaMLO allele may be introduced wherein said mutation is not in the coding region of said third TaMLO allele.

In one embodiment, loss of function mutations are introduced in the coding regions of TaMLO-A1 and TaMLO-D1 and the expression of TaMLO-B1 is reduced.

The third mutation results in impaired accumulation of the transcript of the third TaMLO allele and/or impaired accumulation of the protein encoded by the third TaMLO allele but is not in the coding region of said third TaMLO allele.

Plants that have a loss of function mutation in one or two MLO genes according to the invention can be crossed to obtain a loss of function triple mutant. For example, a plant obtained by a method above that has a loss of function mutation in the TaMLO-A1 allele can be crossed with a plant obtained by a method above that has a loss of function mutation in TaMLO-B1 allele or TaMLO-D1 allele. The resulting double mutant can be crossed with another plant obtained by a method above that has mutation which inactivates the remaining allele.

In one embodiment of the methods described herein, all mutations are introduced simultaneously into the wheat plant using targeted genome modification. Progeny that is homozygous for the mutations can then be generated.

Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customizable DNA binding proteins can be used: meganucleases derived from microbial mobile genetic elements, ZF nucleases based on eukaryotic transcription factors, rare-cutting endonucleases, for example TALENs, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate its nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

The step of introducing a mutation comprises contacting a population of wheat plant cells with DNA binding protein targeted to endogenous TaMLOA, B and D sequences, for example selected from the DNA binding proteins listed above.

In one embodiment, the method comprises contacting a population of wheat plant cells with one or more rare-cutting endonucleases targeted to endogenous TaMLO-A, B and D sequences.

The method may further comprise the steps of selecting, from said population, a cell in which TaMLOA, B and D have been inactivated and regenerating said selected plant cell into a wheat plant.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats.

This is followed by a single truncated repeat of 20 amino acids. The majority of naturally occurring TAL effectors examined have been between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and U.S. Pat. No. 8,450,471. Reference 30 describes a set of customized plasmids that can be used with the Golden Gate cloning method to assemble multiple DNA fragments. As described therein, the Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

Cas9 is thus the hallmark protein of the type II CRISPR-Cas system, and a large monomeric DNA nuclease guided to a DNA target sequence adjacent to the PAM (protospacer adjacent motif) sequence motif by a complex of two non-coding RNAs: CRIPSR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3.

Cas9 expression plasmids for use in the methods of the invention can be constructed as described in the art. One example is provided as described in the example section herein.

The method for producing a mutant wheat plant according to the invention resistant to Pm using genome editing comprises the use of a SSN. This may be selected from a meganuclease, ZFN, TALEN, or CRISPR/Cas9. In one embodiment, the SSNs is a TALEN.

Thus, in one embodiment, the method comprises the use of TALEN. In this embodiment, the method comprises introducing an expression vector comprising a TALEN into a wheat plant and screening for TALEN-induced targeted mutations in TaMLO-A1, TaMLO-B1 and/or TaMLO-D1 genes. The method may also comprise the further step of regenerating a plant and selecting or choosing a plant resistant to Pm.

Figure 9:
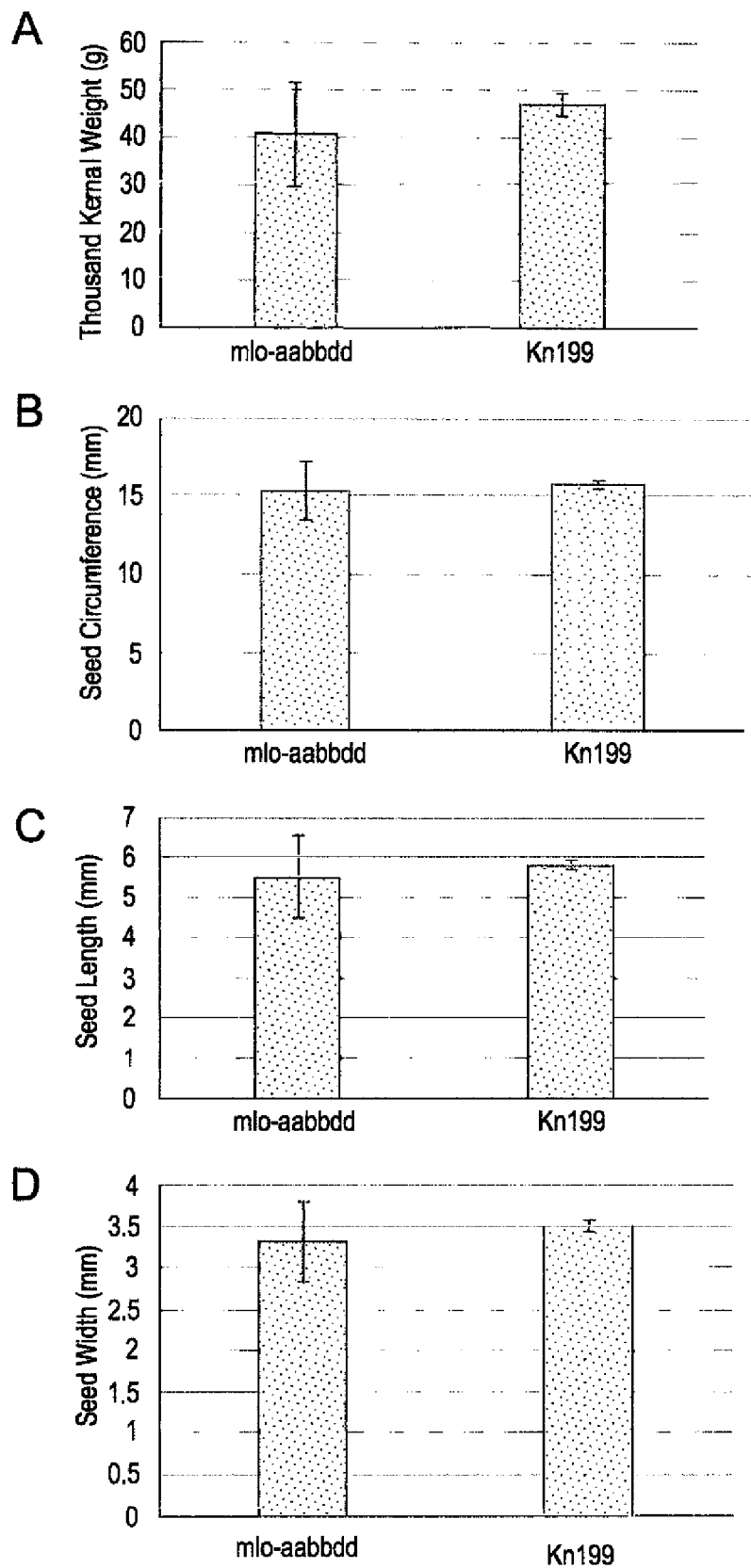
FIG. 9: Phenotypic analysis of mlo-aabbdd mutant. (A) Thousand kernel weights (TKW) of mlo-aabbdd mutant in Kn199 background compared to wild type Kn199(WT). (B) (C) and (D), the seed circumference, length and width of mlo-aabbdd mutant plants compared to WT. All the data are from 8 lines replicates for mlo-aabbdd and WT.

In one embodiment, said vector comprises a pair of TALENs (T-MLO) targeting a conserved region in exon 2 (FIG. 1a, 9 and table 1). The vector construct encodes a pair of TALENs that targets sequences conserved between all three homoeologues MLO genes of wheat.

Thus, in one embodiment, the target sequence site in TaMLO is TCGCTGCTGCTCGCCGTgacgcaggacccatctcCGGGATATGCATCTCCGA (SEQ ID NO. 13, Table 1).

Specifically, the binding site sequences of the second exon conserved region TaMLO-A, TaMLO-B and TaMLO-D to which these TALENs bind are:

```
                                          (SEQ ID NO. 14)
MLO-A:TCGCTGCTGCTCGCCGTcacgcaggacccaatctcCGGGATATG
CATCTCCCA (SEQ ID NO. 15)
MLO-B:TCGCTGCTGCTCGCCGTgacgcaggacccatctcCGGGATATG
CATCTCCGA (SEQ ID NO. 16)
MLO-D:TCGCTGCTGCTCGCCGTgacgcaggacccaatctcCGGGATATG
CATCTCCGA
```

The three SNPs are in bold and underlined. The AvaII restriction site is shown in small letters and underlined.

A TALEN pair has for example the nucleic acid sequence SEQ ID NO. 11. The corresponding amino acid sequence is SEQ ID NO. 12.

Figures 2A, 2B, 2C:
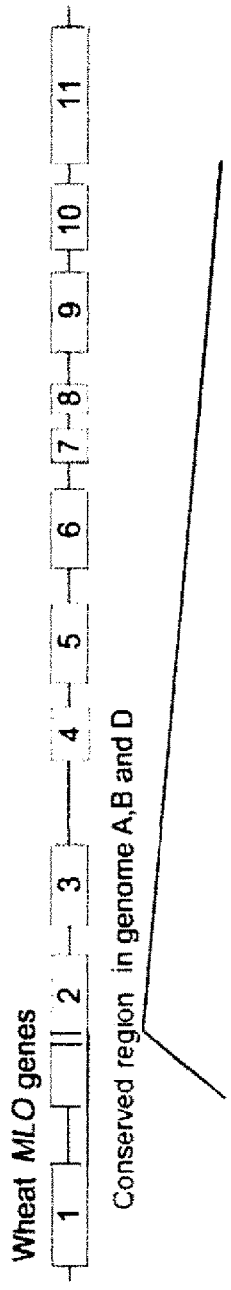
FIG. 2. Targeted knock-out of TaMLO genes using TALENs. (a) Sites within a conserved region of exon 2 of wheat TaMLO homoeologs targeted by TALENs. The TALEN-targeted sequences in MLO-A1, MLO-B1 and MLO-D1 are underlined, and the AvaII restriction site in the spacer is GGACC (SEQ ID NO. 43, SEQ ID NO. 44, SEQ ID NO. 45). There are three SNPs, two are in the spacer region. The first is C/G/G respectively directly adjacent to the underlined 5' region. The second is A/C/A 3' of the AvaII region following residue C directly adjacent to the AvaII region. The third one lies near the far right of the TALEN binding site (penultimate 3' residue). (b) Mutations in TaMLO homologous "triple" mutants are located in the A and D coding sequences. Tamlo-R (with genetic profile tamlo-AaBBDd) is heterozygous in genome A and D. No mutation was identified at the target site in genome B in T0 plants (SEQ ID NO. 46, SEQ ID NO. 47, SEQ ID NO. 48). (c) Phenotype of homozygous T1 mutant lines. When all the 7 homozygous T1 plants were challenged with conidiospores of a virulent Bgt race, only the homozygous plant R32 confers resistance to powdery mildew. R32 did not display the senescence-like chlorosis, and the plant grew as vigorously as the wild type.

In this embodiment, the TALEN pair recognizes 16 bp and 17 bp, respectively, of contiguous DNA separated by an 18 bp spacer DNA containing an AvaII restriction site as shown above, (Table 1). The TALEN recognition sequences are strictly conserved in TaMLO-B1 and TaMLO-D1, but have one nucleotide mismatch with the cognate TaMLO-A1 target site (FIG. 2a). In addition, the conserved spacer region in FIG. 2a contains two single nucleotide polymorphisms (SNPs) among the three MLO homoeo-alleles.

As shown in the examples, in order to detect the mutation at the site targeted by the genetic editing technique, an Ava II enzyme digestion locus was selected from the targeted sites; if mutation occurred, then the Ava II enzyme digestion locus was damaged and cannot be digested. However, non-mutated PCR products are susceptible to digestion.

In one embodiment, the TALENs are assembled by the Golden Gate cloning method and built into a single plasmid as described in the examples.

In one embodiment, screening for TALEN-induced targeted mutations in TaMLO-A1, TaMLO-B1 and TaMLO-D1 genes comprises obtaining a DNA sample from a transformed plant and carrying out DNA amplification and optionally restriction enzyme digestion to detect a mutation in TaMLO-A1, TaMLO-B1 and/or TaMLO-D1. When the target site is as shown above, the restriction enzyme is AvaII.

PCR fragments amplified from the transformed plants are then assessed using a gel electrophoresis based assay. In a further step, the presence of the mutation may be confirmed by sequencing the TaMLO-A1, TaMLO-B1 and/or TaMLO-D1 genes.

In another embodiment, the method comprises the use of CRISPR/Cas9. In this embodiment, the method therefore comprises introducing and co-expressing in a wheat plant Cas9 and sgRNA targeted to TaMLO-A1, TaMLO-B1 and/or TaMLO-D1 and screening for induced targeted mutations in TaMLO-A1, TaMLO-B1 and TaMLO-D1 genes. The method may also comprise the further step of regenerating a plant and selecting or choosing a plant resistant to Pm.

Cas9 and sgRNA may be comprises in a single or two expression vectors.

The target sequence in TaMLO-A1 may be CCGTCACGCAGGACCCAATCTCC (SEQ ID NO. 17, see table 1).

In one embodiment, screening for CRISPR-induced targeted mutations in TaMLO-A1, TaMLO-B1 and TaMLO-D1 genes comprises obtaining a DNA sample from a transformed plant and carrying out DNA amplification and optionally restriction enzyme digestion to detect a mutation in TaMLO-A1, TaMLO-B1 and/or TaMLO-D1.

In one embodiment, the restriction enzyme is mismatch-sensitive T7 endonuclease. T7E1 enzyme that is specific to heteroduplex DNA caused by genome editing.

PCR fragments amplified from the transformed plants are then assessed using a gel electrophoresis assay based assay. In a further step, the presence of the mutation may be confirmed by sequencing the TaMLO-A1, TaMLO-B1 and/or TaMLO-D1 genes.

As shown in the examples, genomic DNA (i.e. wt and mutant) can be prepared from each sample, and DNA fragments encompassing each target site are amplified by PCR (see Table). The PCR products are digested by restriction enzymes as the target locus includes a restriction enzyme site. The restriction enzyme site is destroyed by CRISPR- or TALEN-induced mutations by NHEJ or HR, thus the mutant amplicons are resistant to restriction enzyme digestion, and result in uncleaved bands. Alternatively, the PCR products are digested by T7E1 (cleaved DNA produced by T7E1 enzyme that is specific to heteroduplex DNA caused by genome editing) and visualized by agarose gel electrophoresis. In a further step, they are sequenced.

In another aspect, the invention relates to a method for conferring resistance to Pm to a wheat plant, plant part or plant cell comprising introducing a loss of function mutation into the coding region of two MLO alleles selected from TaMLO-A1, TaMLO-B1 and TaMLO-D1 and reducing expression of the third TaMLO allele, for example by introducing a further mutation which results in impaired accumulation of the transcript of the third TaMLO allele and/or impaired accumulation of the protein encoded by the third TaMLO allele wherein said mutation is not in the coding region of the third TaMLO allele wherein said mutations are introduced using targeted genome modification.

In one embodiment, ZFN, a rare-cutting endonuclease, for example TALEN, or CRISPR/Cas9 is used. In one embodiment, the method comprises producing a mutant plant as described above.

In the methods above, amplification is preferably carried out using PCR and primers that specifically amplify TaMLO-A1, TaMLO-B1 and TaMLO-D1 (table 2) and as shown below:

The following primer pair amplifies the TaMLO-A1 target site:

```
MLO-A1-F
                                      (SEQ ID NO. 18)
TGGCGCTGGTCTTCGCCGTCATGATCATCGTC

MLO-A1-R
                                      (SEQ ID NO. 19)
TACGATGAGCGCCACCTTGCCCGGGAA
```

The following primer pair amplifies the TaMLO-B1 target site:

```
MLO-B1-F
                                      (SEQ ID NO. 20)
ATAAGCTCGGCCATGTAAGTTCCTTCCCGG

MLO-B1-R
                                      (SEQ ID NO. 21)
CCGGCCGGAATTTGTTTGTGTTTTTGTT
```

The following primer pair amplifies the TaMLO-D1 target site:

```
MLO-D1-F
                                      (SEQ ID NO. 22)
TGGCTTCCTCTGCTCCCTTGGTGCACCT

MLO-D1-R
                                      (SEQ ID NO. 23)
TGGAGCTGGTGCAAGCTGCCCGTGGACATT
```

The following primer pair amplifies all three alleles

```
MLO-F
                                      (SEQ ID NO. 24)
GTCTTCGCCGTCATGATCATCGTCTCC

MLO-R
                                      (SEQ ID NO. 25)
TGGTATTCCAAGGAGGCGGTCTCTGTCT
```

In a preferred embodiment, the methods above are carried out by transforming wheat embryos. In a further preferred embodiment, the methods comprise generating stable T2 plants preferably homozygous for the mutation.

In one embodiment, the methods do not comprise transforming wheat protoplasts.

The methods above use plant transformation to introduce an expression vector comprise a SSN into a plant. The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The resulting transformed plant cell may then be used to regenerate a transformed plant in a manner known to persons skilled in the art. The transfer of foreign genes into the genome of a plant is called transformation. Transformation of plants is now a routine technique in many species. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle bombardment as described in the examples, transformation using viruses or pollen and microprojection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation.

To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. Alternatively, the transformed plants are screened for the presence of a selectable marker.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The SSN is preferably introduced into a plant as part of an expression vector. The vector may contain one or more replication systems which allow it to replicate in host cells. Self-replicating vectors include plasmids, cosmids and virus vectors. Alternatively, the vector may be an integrating vector which allows the integration into the host cell's chromosome of the DNA sequence. The vector desirably also has unique restriction sites for the insertion of DNA sequences. If a vector does not have unique restriction sites it may be modified to introduce or eliminate restriction sites to make it more suitable for further manipulation. Vectors suitable for use in expressing the nucleic acids, are known to the skilled person and a non-limiting example is pYP010.

The nucleic acid is inserted into the vector such that it is operably linked to a suitable plant active promoter. Suitable plant active promoters for use with the nucleic acids include, but are not limited to CaMV35S, wheat U6, or maize ubiquitin promoters.

The vector may also comprise a GFP sequence or other marker as explained in the examples and in the figures.

A plant, plant part or plant cell obtained or obtainable by the methods described above is also within the scope of the invention.

In one aspect, the mutant is TALEN free. Thus, according to the method above, the presence of a TALEN can be assessed as described in the examples.

In additional steps, the method may comprise determining the presence of a mutant tamlo-a1, tamlo-b1 and/or tamlo-d1 nucleic acid or detecting the presence or absence of a TaMLO-A, B or D protein in a wheat plant.

A diagnostic test determining the presence of a mutant tamlo-a1, tamlo-b1 and/or tamlo-d1 nucleic acid may involve hybridisation of a suitable oligo- or poly-nucleotide, such as a fragment of the Mlo gene. The hybridisation may involve PCR designed to amplify a nucleic acid product from a given allelic version of mlo, with subsequent detection of an amplified product by any of a number of possible methods including but not limited to gel electrophoresis, capillary electrophoresis and direct hybridisation of nucleotide sequence probes. A diagnostic test may be based on PCR designed to amplify various mutant nucleic acids from the Mlo locus, with a test to distinguish the different possible mutant nucleic acids from the wild type by any of a number of possible methods, including DNA fragment size, restriction site variation (e.g. CAPS-cleaved amplified polymorphic sites) and so on. A diagnostic test may also be based on a great number of possible variants of nucleic acid analysis that will be apparent to those skilled in the art, such as use of a synthetic mlo-derived sequence as a hybridisation probe.

Suitable tests for assessing the presence of a mutant allele according to the invention include but are not limited to among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs-which are also referred to as Microsatellites), and Single Nucleotide Polymorphisms (SNPs). In one embodiment, Kompetitive Allele Specific PCR (KASP) genotyping is used. In one embodiment, the method comprises a) obtaining a nucleic acid sample from a wheat plant and
b) carrying out nucleic acid amplification of one or more TaMLO allele using one or more primer pairs selected from SEQ ID NOs 18 to 25 or SEQ ID NOs. 34-37.

```
MLO-R32-A1-F:
                                   SEQ ID NO. 34
TGATGATGATGATGATGGAACTTGTTCTCG

MLO-R32-A1-R:
                                   SEQ ID NO. 35
AAGGAGGCGGTCTCTGTCTCCCATTTCTTC

MLO-R32-D1-F:
                                   SEQ ID NO. 36
TTCATCTCGCTGCTGCTCCATCTCCG

MLO-R32-D1-R:
                                   SEQ ID NO. 37
AGCCATGATGATGACGCTGTAGGTGACATG
```

In one embodiment, the method comprises determining whether a TaMLO protein accumulates in the plant. Thus, the presence or absence of a TaMLO-A, B or D protein in a plant is detected. If the protein is absent, a mutation which impairs protein accumulation is present in the genome of the plant. In one embodiment, the presence or absence of a TaMLO-B protein in a plant is detected.

Suitable tests for assessing the presence of a protein are known in the art and include, but are not limited to, Gel Electrophoresis (such as Polyacrylamide Protein Gel Electrophoresis or 2D Gel Electrophoresis), colorimetric assays, Western Blotting, Immunoassays (such as ELISA, lateral flow strips or immunostaining) or spectrophotometry.

The invention also relates to an isolated nucleic acid sequence comprising one or more primer selected from SEQ ID NOs. 34-37. The invention also relates to a detection kit comprising one or more primer selected from SEQ ID NOs. 34-37.

The various aspects of the invention described herein clearly extend to any plant cell or any plant produced, obtained or obtainable by any of the methods described herein, and to all plant parts and propagules thereof unless otherwise specified. The present invention extends further to encompass the progeny of a mutant plant cell, tissue, organ or whole plant that has been produced by any of the aforementioned methods, the only requirement being that progeny exhibit the same genotypic and/or phenotypic characteristic(s) as those produced by the parent in the methods according to the invention.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification, including reference to sequence database identifiers, are incorporated herein by reference in their entirety. Unless otherwise specified, when reference to sequence database identifiers is made, the version number is 1.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The invention is further described in the following non-limiting examples.

EXAMPLES

Talen Design and Construction

TALEN target sites were designed using the TAL effector-Nucleotide Targeter 2.0 (TALE-NT) program (https://tale-nt.cac.cornell.edu/). All the target sites had a T at the −1 position, and the corresponding TAL effector arrays were constructed using the Golden Gate method as previously described[33]. Information on all the TAL effecter arrays and target sites is given in Table 1. TALENs were assembled in vectors with a truncated N152/C63 backbone architecture (pZHY500 and pZHY501). The Gateway-compatible entry plasmid, pZHY013, was used as the intermediate vector to create TALEN expression vectors[34]. This plasmid contains two heterodimeric FokI nuclease domains separated by a T2A translational skipping sequence. TAL arrays in the plasmids pZHY500 and pZHY501 were released by digestion with XbaI/BamHI and subcloned into pZHY013 one-by-one[34,35]. One array (left array) was first cloned into pZHY013 as an XbaI/BamHI fragment; the other (right array) was then cloned into the NheI/BglII sites, which have ends compatible with XbaI and BamHI. A Gateway LR reaction was performed to clone the TALEN coding sequences into the destination vector, pYPO10 (a derivative of pZHY05134 by replacing the 35S promoter with the maize ubiquitin promoter.

Construction of Cas9 and sgRNA Expression Vectors

The plasmid pJIT163 was used to construct the Cas9 expression plasmid. It was digested with KpnI and HindIII and fused with the maize ubiquitin 1 promoter (Ubi) to construct vector pJIT163-Ubi. Full-length Cas9 (plant codon-optimized) products were digested with BamHI and MfeI and inserted into plasmid pJIT163-Ubi between the BamHI and MfeI sites to yield the expression vector pJIT163-Ubi-Cas9. The wheat U6 promoters and wheat gRNA scaffolds were synthesized by GenScript and cloned into pEASY-blunt vector (TransGen Biotech). The sequences of Cas9 and the gRNAs are given in a previous publication[17]. Wheat genomic DNA region immediately precede a 5'-NGG PAM, such as 5'-G-N(20)-GG-3' or 5'-N (21)-GG-3' was selected as target.

The CRISPR/Cas9 target site in TaMLO contains two single nucleotide polymorphisms (SNPs) among the three homoeoalleles. We designed a sgRNA (sgMLO-A1) to specifically target TaMLO-A1. Our results show that sgRNA-A1-induced mutations only occurred in TaMLO-A1, so confirming the specificity of the sgRNA for TaMLO-A1. Therefore, off-target cleavage did not occur in TaMLO-B1 and TaMLO-D1. The results show that CRISPR/Cas9 is active in wheat plants and that transgenic mutant lines can be generated. Other mutants, including a triple mutant AA, BB and DD can be obtained using Cas9/sgRNA by targeting a conserved target site.

Wheat Protoplast Transformation

Wheat protoplasts were isolated and transformed as previously described[3]. Average transformation efficiencies were 60-80%. Protoplast transformation was carried out with 20 µg of TALEN plasmid per transformation, or a mixture of 10 µg pJIT163-Ubi-Cas9 plasmid and 10 µg pU6-gRNA plasmid.

Biolistic Transformation of Wheat

Biolistic transformation was performed using a PDS1000/He particle bombardment system (Bio-Rad, Hercules, Calif.) with a target distance of 6.0 cm from the stopping plate at helium pressure 1100 psi. Plasmid DNAs (T-MLO and pAHC20) were mixed in a 1:1 (1:1:1 for Cas9, sgRNA and pAHC20) molar ratio prior to bombardment. After bombardment, embryos were transferred to callus induction medium. In the third or fourth week, all calli were transferred to selective regeneration medium containing 5 mg/l phosphinothricin (PPT). PPT was present in all subsequent tissue culture procedures including 2 rounds of regeneration (4 weeks) and 2 rounds of rooting (4 weeks). After 10-12 weeks, T0 transgenic plants were obtained, transferred into soil and grown in a management greenhouse[37].

Screening of SSN-Induced Mutations

Genomic DNA from individual wheat plants was extracted using the high-throughput Automation Workstation Biomek® FX (Beckmen) with the magnetic bead-based DNA extraction kit (GeneOn Biotech). The PCR/RE digestion screen assay and T7E1 assay were used to identify the mutations as previously described[35, 36, 37]. The PCR products amplified with TaMLO-specific primers (Table 3) from individual mutant plants were cloned into pUC-T vector (CWBIO) for sequencing. Mutation frequencies (indels (%)) in protoplasts were calculated by measuring band intensities with UVP VisionWorks LS Image Acquisition Analysis Software 7.0[36].

Powdery Mildew Infection and Microscopic Analyses

Wheat plants were grown on soil in controlled environment chambers at 22° C. and 16-h photoperiod with light intensity ranging from 400-1,000 µmol m$^{-2}$ s$^{-1}$. Powdery mildew infection and microscopic analyses were performed as previously reported[39] with some modifications. Leaves originating from the main stem (leaves 2, 3, and 4) were cut into 5 cm segments and immediately placed in Petri dishes containing 1% (w/v) distilled water agar and 8.5 mM benzimidazole. The leaf segments were incubated at 22° C. in continuous light (100 µmol m$^{-2}$ s$^{-1}$) for four hour, then inoculated with virulent strains of *Blumeria graminis* f. sp. *tritici* (Bgt) E09, E22 and B13 to give approximately 15 to 20 sporulating colonies per cm$^2$ and incubated at 22° C. in continuous light (100 umol m$^{-2}$ s$^{-1}$). Seventy-two hours after inoculation, the leaf segments were fixed with 1:1 (v/v) ethanol: acetic acid for 24 h, cleared with lactoglycerol (1:1:1 [v/v] lactic acid:glycerol:H2O) for 48 h, and stained for 7 sec with Coomassie blue (0.6% [w/v] Coomassie Brilliant Blue R 250 [Sigma] in methanol) to visualize the fungal structure, finally rinsed in distilled water and mounted in 50% (v/v) glycerol prior to microscopy. Samples were observed and analyzed under an Olympus BX51light microscope, and photographs were taken using software Cellsens Entry 1.21.

Yield Index Test for Mlo Mutants

Plants were grown in a standard wheat field in 20×10 cm plots (20 plants) under conventional cultivation conditions. There was no powdery mildew disease in the field and no fungicide was used. All phenotypical data including thousand seed weight (TKW), seed circumference, seed length and seed width were measured. Data were from 9 replicates for the mutant R32 and wildtype control (Bobwhite), 8 replicates for the mutat mlo-aabbdd and wildtype control (Kn199), respectively.

About 400 filled grains of mutant lines and wildtype plants of one 5-plant sample in every replicate were picked for TKW measurements using Electron balance. About 150 filled mutants and wildtype grains of one treatment in every sample were used to measure the seed circumference, seed length and seed width by Wanshen kaozhong examination analyzer.

Results and Discussion

We deployed a pair of TALENs (T-MLO) targeting a conserved region in exon 2 (FIG. 2*a*). The TALEN pair recognizes 16 bp and 17 bp, respectively, of contiguous DNA separated by an 18 bp spacer DNA containing an AvaII restriction site (FIG. 1*a* and Table 1). The TALEN recognition sequences are strictly conserved in TaMLO-B1 and TaMLO-D1, but have one nucleotide mismatch with the cognate TaMLO-A1 target site (FIG. 2*a*). In addition, the conserved spacer region in FIG. 2*a* contains two single nucleotide polymorphisms (SNPs) among the three MLO homoeo-alleles. The TALENs were assembled by the Golden Gate cloning method[30], and built into a single plasmid by a T2A translational skipping sequence driven by the maize ubiquitin promoter. The activity of the resulting T-MLO was first evaluated by transforming the TALEN-carrying plasmid into wheat protoplasts. Analysis of genomic DNA from the transformed protoplasts using a previously developed PCR restriction enzyme digestion assay (PCR/RE)[16] demonstrated the occurrence of mutations at the target site.

We then co-transformed the T-MLO plasmid and pAHC20[31], a plasmid harboring the selectable bar gene, into immature wheat embryos by the particle bombardment method. Wheat seedlings were regenerated from herbicide-resistant calli after 6-8 weeks of selection on 5 µg/ml phosphinothricin (PPT). The MLO target sites (in TaMLO-A1, TaMLO-B1 and TaMLO-D1) were first amplified from the genomic DNA of these transgenic seedlings (T0 plants) using a conserved primer set (Table 2), and analyzed by the PCR/RE assay to detect potential mutations. In order to identify in which of the TaMLO genes the mutations occurred, we designed primers to specifically amplify TaMLO-A1, TaMLO-B1 and TaMLO-D1 and conducted PCR/RE assays of the PCR amplicons with the specific primers (Table 2). This revealed the revealed that T-MLO-induced mutations as shown in FIG. 1.

We identified Tamlo-R (with genetic profile tamlo-AaBBDd), which is heterozygous in genome A and D, but no mutation was identified at the target site in genome B in T0 plants (FIG. 2). After segregation, in T1 generation, we identified 7 plants homozygous for the mutation in genome A and D (tamlo-aaBBdd), named as R4, R25, R26, R32, R40, R51 and R54. When all the 7 homozygous T1 plants were challenged with conidiospores of a virulent Bgt race, we found that only the homozygous plant R32 confers resistance to powdery mildew (FIG. 2). Interestingly, R32 did not display the senescence-like chlorosis, and the plant grew as vigorously as the wild type.

Figure 8:
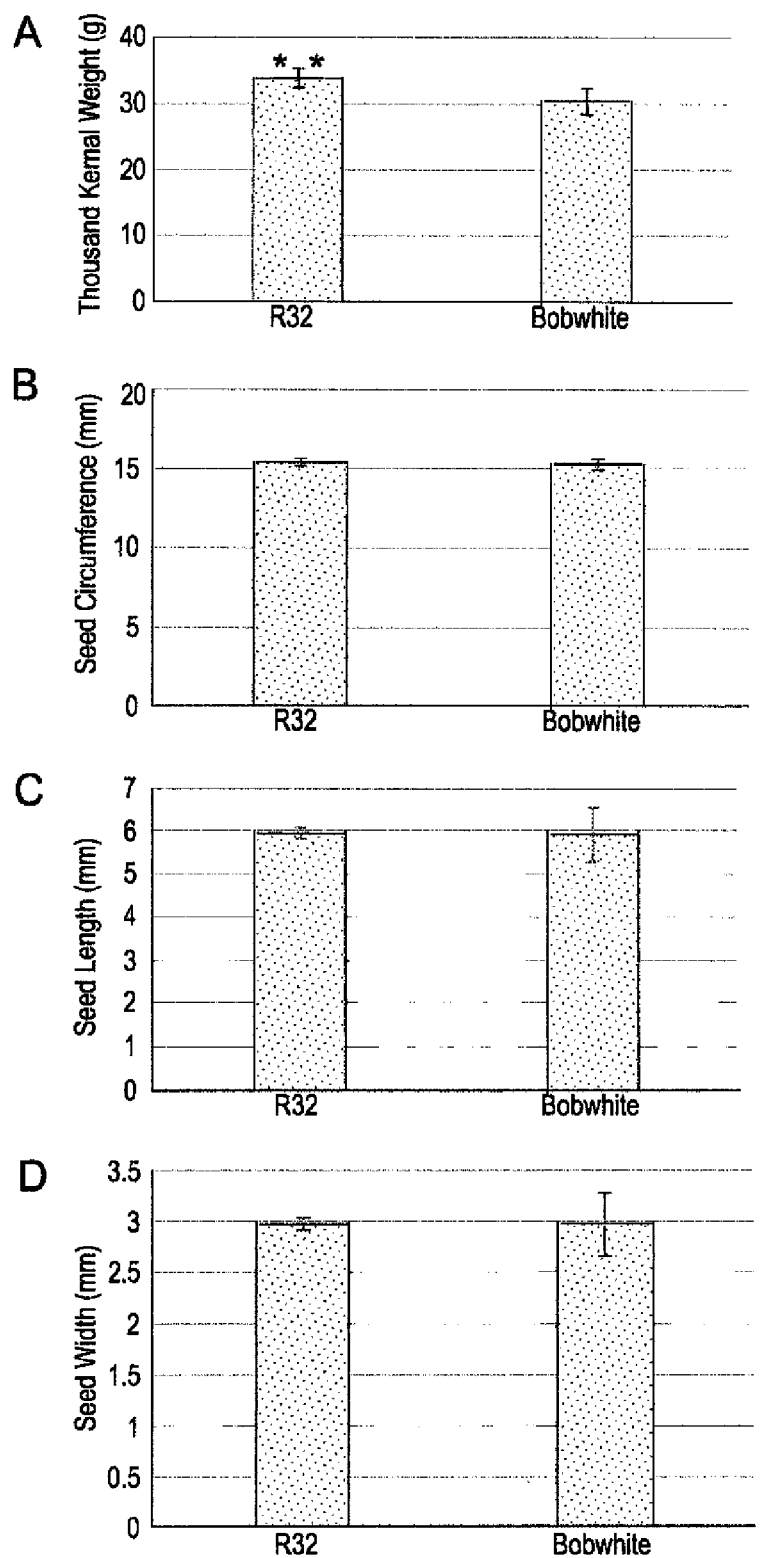
FIG. 8: Phenotypic analysis of mlo mutant R32. (A) Thousand kernel weights (TKW) of R32 mutant in Bobwhite background compared to wildtype Bobwhite control (WT). Values are mean±s.d**P<0.01 (t-tests). (B) (C) and (D), the seed circumference, length and width of R32 mutant plants compared to WT. All the data are from 9 line replicates for R32 and WT.

To confirm this view, we tested the thousand kernel weight (TKW) for the R32 mutant and wild type plant in the yield. The results showed that the R32 (which is in Bobwhite background) has significantly elevated thousand kernel weight (TKW) compared with wildtype in Bobwhite WT control (P<0.01), but there was no such difference between the mlo-aabbdd mutant (in Kn199 background) and Kn199 WT control (FIG. 8A and FIG. 9A). Moreover, there is no obvious change in other parameters including seed circumference, seed length and seed width between mutant (R32 and mlo-aabbdd) and wildtype both in Bobwhite and Kn199 (FIGS. 8 and 9).

We also assessed the resistance to powdery mildew of offspring of all the homozygous mutant progeny of line Tamlo-R (R4, R25, R26, R32, R40, R51 and R54). We found that all the progeny of R32 showed resistance to Bgt, and about ⅓ of R26, R40 and R54 offspring were resistant to the Bgt. All the progeny of R51 were susceptible to the Bgt (FIG. 3). In contrast to fully resistant mutant tamlo-aabbdd plants, the resistant mutant plants allow the low-level growth of sporulating Bgh (FIG. 3).

We assessed the level of transcription of mlo for these mutants in genome A, B and D, respectively. We find that the transcription of the TaMLO protein of genome B (TaMLO-B1) of these resistant plants was lower compared with wild type (FIG. 4).

To date, race-specific resistance controlled by the resistance (R) gene is commonly used for developing resistant wheat varieties, but this tends to break down as new Bgt races emerge in the field[32]. In contrast, loss-of-function mlo mutation-conferred resistance against powdery mildew has not been broken since its introgression into elite barley varieties three decades ago[25]. Therefore, the mlo-aaBBdd alleles we generated in the elite wheat cultivars may provide excellent starting materials for breeding durable and broad-spectrum resistance in bread wheat.

Genetic Mapping

Genetic mapping as shown in FIG. 7 is being carried out.

TABLE 1

SSN target loci and sequences

| Gene Name | SSN ID | Target Site | Left Binding Site RVDs/Oligo-F (5'-3') | Right Binding Site RVDs/Oligo-R (5'-3') | Detection method |
|---|---|---|---|---|---|
| TaMLO | T-MLO | TCGCTGCTGCTCGC CGTgacgcaggaccccatctc CGGGATATGCATCT CCGA SEQ ID NO. 13 | HD NN HD NG NN HD NG NN HD NG HD NN HD HD NN NG SEQ ID NO. 49 | HD NN NN NI NN NI NG NN HD NI NG NI NG HD HD HD NN SEQ ID NO. 50 | PCR/RE: AvaII |
| TaMLO-A1 | sgMLO-A1 | CCGTCACGCAGGAC CCAATCTCC SEQ ID No. 17 | CTTGGAGATTGGG TCCTGCGTGA SEQ ID No. 26 | AAACTCACGCAG GACCCAATCTC SEQ ID No. 27 | T7E1 |

TABLE 2

PCR primers used and their applications

| Primer name | Primer sequence | Experiment |
|---|---|---|
| MLO-A1-F | TGGCGCTGGTCTTCGCCGTCATGATCATCGTC SEQ ID No. 18 | Gene specific primer amplifying the TaMLO-A1 target site |
| MLO-A1-R | TACGATGAGCGCCACCTTGCCCGGGAA SEQ ID No. 19 | |
| MLO-B1-F | ATAAGCTCGGCCATGTAAGTTCCTTCCCGG SEQ ID No. 20 | Gene specific primer amplifying the TaMLO-B1 target site |
| MLO-B1-R | CCGGCCGGAATTTGTTTGTGTTTTTGTT SEQ ID No. 21 | |
| MLO-D1-F | TGGCTTCCTCTGCTCCCTTGGTGCACCT SEQ ID No. 22 | Gene specific primer amplifying the TaMLO-D1 target site |
| MLO-D1-R | TGGAGCTGGTGCAAGCTGCCCGTGGACATT SEQ ID No. 23 | |
| MLO-F | GTCTTCGCCGTCATGATCATCGTCTCC SEQ ID No. 24 | Amplifying the TaMLO target site: This primer can be used to amplify all three alleles |
| MLO-R | TGGTATTCCAAGGAGGCGGTCTCTGTCT SEQ ID No. 25 | |
| F1 | GTCTTCGCCGTCATGATCATCGTCTCC SEQ ID No. 28 | Detecting NHEJ-mediated GFP inserts |
| R1 | GGTGCTCAGGTAGTGGTTGTC SEQ ID No. 29 | |
| F2 | CTTTGTCGTGAATATAAACCAGACACGAG SEQ ID No. 30 | Detecting NHEJ-mediated GFP inserts |
| R2 | TGGTATTCCAAGGAGGCGGTCTCTGTCT SEQ ID No. 31 | |
| Ubi-F | CAGTTAGACATGGTCTAAAGGACAATTGAG SEQ ID No. 32 | Detecting the absence of TALENs |
| Ubi-R | CCAACCACACCACATCATCACAACCAA SEQ ID No. 33 | |

REFERENCES

All references are incorporated herein by reference.
1. Voytas, D. F. Plant genome engineering with sequence-specific nucleases. *Annu. Rev. Plant. Biol.* 64, 327-350 (2013).
2. Bogdanove, A. J. & Voytas, D. F. TAL effectors: customizable proteins for DNA pargeting. *Science* 333, 1843-1846 (2011).
3. Jinek, M. et al. A programmable dual-RNA-guided DNA endonuclease in adaptive bacterial immunity. *Science* 337, 816-821 (2012).
4. Várallyay, É., Giczey, G. & Burgyán, J. Virus-induced gene silencing of Mlo genes induces powdery mildew resistance in *Triticum aestivum*. *Arch. Virol.* 157, 1345-1350 (2012).
5. Slade, A. J. et al. A reverse genetic, nontransgenic approach to wheat crop improvement by TILLING. *Nat. Biotechnol.* 23, 75-81 (2005).
6. Dvoířák, J. in Genetics and Genomics of the Triticeae, Vol. 7. (eds. G. J. Muehlbauer & C. Feuillet) 685-711 (Springer US, 2009).
7. Bibikova, M., Beumer, K., Trautman, J. K. & Carroll, D. Enhancing gene targeting with designed zinc finger nucleases. *Science* 300, 764 (2003).
8. Gorbunova, V. & Levy, A. A. Non-homologous DNA end joining in plant cells is associated with deletions and filler DNA insertions. *Nucleic Acids Res.* 25, 4650-4657 (1997).
9. Puchta, H., Dujon, B. & Hohn, B. Homologous recombination in plant cells is enhanced by in vivo induction of double strand breaks into DNA by a site-specific endonuclease. *Nucleic Acids Res.* 21, 5034-5040 (1993).
10. Zhang, F. et al. High frequency targeted mutagenesis in *Arabidopsis thaliana* using zinc-finger nucleases. *Proc. Nat.l Acad. Sci.* 107, 12028-12033 (2010).
11. Feng, Z. et al. Multigeneration analysis reveals the inheritance, specificity, and patterns of CRISPR/Cas-induced gene modifications in *Arabidopsis*. *Proc. Nat.l Acad. Sci.* doi:10.1073/pnas.1400822111 (2014).
12. Zhang, Y. et al. Transcription activator-like effector nucleases enable efficient plant genome engineering. *Plant physiol.* 161, 20-27 (2013).
13. Wendt, T. et al. TAL effector nucleases induce mutations at a pre-selected location in the genome of primary barley transformants. *Plant Mol. Biol.* 83, 279-285 (2013).
14. Gurushidze, M. et al. True-breeding targeted gene knock-out in barley using designer TALE-nuclease in haploid cells. *PloS one* 9, e92046. doi:10.1371/journal.pone.0092046 (2014).
15. Curtin, S. J. et al. Targeted mutagenesis of duplicated genes in soybean with zinc-finger nucleases. *Plant physiol.* 156, 466-473 (2011).
16. Shan, Q. et al. Rapid and efficient gene modification in rice and brachypodium using TALENs. *Mol. Plant* 6, 1365-1368 (2013).
17. Shan, Q. et al. Targeted genome modification of crop plants using a CRISPR-Cas system. *Nat. Biotechnol.* 31, 686-688 (2013).
18. Li, T. et al. High-efficiency TALEN-based gene editing produces disease-resistant rice. *Nat. Biotechnol.* 30, 390-392 (2012).
19. Feng, Z. et al. Efficient genome editing in plants using a CRISPR/Cas system. *Cell Res.* 23, 1229-1232 (2013).
20. Miao, J. et al. Targeted mutagenesis in rice using CRISPR-Cas system. *Cell Res.* 23, 1233-1236 (2013).
21. Xie, K. & Yang, Y. RNA-guided genome editing in plants using a CRISPR-Cas system. *Mol. Plant.* doi: 10.1093/mp/sst119 (2013).
22. Shukla, V. K. et al. Precise genome modification in the crop species *Zea mays* using zinc-finger nucleases. *Nature* 459, 437-441 (2009).
23. Liang, Z., Zhang, K., Chen, K. & Gao, C. Targeted mutagenesis in *zea mays* using TALENs and the CRISPR/Cas system. *J. Genet. Genomics* 41, 63-68 (2014).
24. Christian, M., Qi, Y., Zhang, Y. & Voytas, D. F. Targeted mutagenesis of *Arabidopsis thaliana* using engineered TAL effector nucleases. *G3 (Bethesda)* 3, 1697-1705 (2013).
25. Büschges, R. et al. The barley Mlo gene: A novel control element of plant pathogen resistance. *Cell* 88, 695-705 (1997).
26. Piffanelli, P. et al. A barley cultivation-associated polymorphism conveys resistance to powdery mildew. *Nature* 430, 887-891 (2004).
27. Consonni, C. et al. Conserved requirement for a plant host cell protein in powdery mildew pathogenesis. *Nat. Genet.* 38, 716-720 (2006).
28. Bai, Y. et al. Naturally occurring broad-spectrum powdery mildew resistance in a central american tomato accession is caused by loss of mlo function. *Mol. Plant Microbe In.* 21, 30-39 (2007).
29. Elliott, C. et al. Functional conservation of wheat and rice Mlo orthologs in defense modulation to the powdery mildew fungus. *Mol. Plant Microbe In.* 15, 1069-1077 (2002).
30. Cermak, T. et al. Efficient design and assembly of custom TALEN and other TAL effector-based constructs for DNA targeting. *Nucleic Acids Res.* 39 (2011).
31. Christensen, A. & Quail, P. Ubiquitin promoter-based vectors for high-level expression of selectable and/or screenable marker genes in monocotyledonous plants. *Transgenic. Res.* 5, 213-218 (1996).
32. McDonald, B. A. & Linde, C. Pathogen population genetics, evolutionary potential, and durable resistance. *Annu. Re. Phytopathol.* 40, 349-379 (2002).
33. Cermak, T. et al. Efficient design and assembly of custom TALEN and other TAL effector-based constructs for DNA targeting. *Nucleic Acids Res.* 39, 1-11 (2011).
34. Zhang, Y. et al. Transcription activator-like effector nucleases enable efficient plant 50 genome engineering. *Plant physiol.* 161, 20-27 (2013).
35. Shan, Q. et al. Rapid and efficient gene modification in rice and brachypodium using TALENs. *Mol. Plant* 6, 1365-1368 (2013).
36. Shan, Q. et al. Targeted genome modification of crop plants using a CRISPR-Cas system. *Nat. Biotechnol.* 31, 686-688 (2013).
37. Rasco-Gaunt, S. et al. Procedures allowing the transformation of a range of European elite wheat (*Triticum aestivum* L.) varieties via particle bombardment. *J. Exp Bot.* 52, 865-874 (2001).
38. Xie, K. & Yang, Y. RNA-guided genome editing in plants using a CRISPR-Cas system. *Molecular plant* 6, 1975-1983 (2013).
39. Hein, I. et al. Virus-induced gene silencing-based functional characterization of genes associated with powdery mildew resistance in barley. *Plant physiol.* 138, 2155-2164 (2005).
40. Acevedo-Garcia et al: magical Mystery tour: MLO proteins in plant immunity and beyond. *New Phytologist*. 1-9 (2014)

41. Hsu et al: Development and Applications of CRISPR-Cas9 for Genome Engineering. Cell 157, 1262-1278, 2014
42. Pifanelli et al A barley cultivation-associated polymorphism conveys resistance to powdery mildew. Nature, Vol. 430, 887-891, 2004
43. Wang et al: Simultaneous editing of three homoeoalleles in hexaploid wheat confers heritable resistance to powdery mildew virus. Nature biotehcnology. September; 32(9):947-51, 2014
44. Consonni, C. et al. Conserved requirement for a plant host cell protein in powdery mildew pathogenesis. Nat. Genet. 38, 716-720 (2006).

Sequence Information

SEQ ID NO. 1 Coding sequence of wild type TaMLO-A1:1605 bp; The TALEN target site is indicated underlined.

ATGGCGGAGGACGACGGGTACCCCCGGCGCGGACGCTGCCGGAGACGCC

GTCCTGGGCGGTGGCGCTGGTCTTCGCCGTCATGATCATCGTCTCCGTCC

TCCTGGAGCACGCGCTCCACAAGCTCGGCCAGTGGTTCCACAAGCGGCAC

AAGAACGCGCTGGCGGAGGCGCTGGAGAAGATGAAGGCGGAGCTGATGCT

GGTGGGATTCATC<u>TCGCTGCTGCTCGCCGTCACGCAGGACCCAATCTCCG</u>

<u>GGATATGCATCTCCCA</u>GAAGGCCGCCAGCATCATGCGCCCCTGCAAGGTG

GAACCCGGTTCCGTCAAGAGCAAGTACAAGGACTACTACTGCGCCAAAGA

GGGCAAGGTGGCGCTCATGTCCACGGGCAGCCTGCACCAGCTCCACATAT

TCATCTTCGTGCTAGCCGTCTTCCATGTCACCTACAGCGTCATCATCATG

GCTCTAAGCCGTCTCAAGATGAGAACATGGAAGAAATGGGAGACAGAGAC

CGCCTCCTTGGAATACCAGTTCGCAAATGATCCTGCGCGGTTCCGCTTCA

CGCACCAGACGTCGTTCGTGAAGCGGCACCTGGGCCTGTCCAGCACCCCC

GGCGTCAGATGGGTGGTGGCCTTCTTCAGGCAGTTCTTCAGGTCGGTCAC

CAAGGTGGACTACCTCACCTTGAGGGCAGGCTTCATCAACGCGCACTTGT

CGCAGAACAGCAAGTTCGACTTCCACAAGTACATCAAGAGGTCCATGGAG

GACGACTTCAAAGTCGTCGTTGGCATCAGCCTCCCGCTGTGGGCTGTGGC

GATCCTCACCCTCTTCCTTGATATCGACGGGATCGGCACACTCACCTGGG

TTTCTTTCATCCCTCTCATCATCCTCTTGTGTGTTGGAACCAAGCTAGAG

ATGATCATCATGGAGATGGCCCTGGAGATCCAGGACCGGTCGAGCGTCAT

CAAGGGGGCACCCGTGGTCGAGCCCAGCAACAAGTTCTTCTGGTTCCACC

GCCCCGACTGGGTCCTCTTCTTCATACACCTGACGCTGTTCCAGAACGCG

TTTCAGATGGCACATTTCGTGTGGACAGTGGCCACGCCCGGCTTGAAGGA

CTGCTTCCATATGAACATCGGGCTGAGCATCATGAAGGTCGTGCTGGGGC

TGGCTCTCCAGTTCCTGTGCAGCTACATCACCTTCCCCCTCTACGCGCTA

GTCACACAGATGGGATCAAACATGAAGAGGTCCATCTTCGACGAGCAGAC

AGCCAAGGCGCTGACCAACTGGCGGAACACGGCCAAGGAGAAGAAGAAGG

TCCGAGACACGGACATGCTGATGGCGCAGATGATCGGCGACGCAACACCC

AGCCGAGGCACGTCCCCGATGCCTAGCCGGGGCTCATCGCCGGTGCACCT

GCTTCAGAAGGGCATGGGACGGTCTGACGATCCCCAGAGCGCACCGACCT

CGCCAAGGACCATGGAGGAGGCTAGGGACATGTACCCGGTTGTGGTGGCG

CATCCTGTACACAGACTAAATCCTGCTGACAGGAGAAGGTCGGTCTCTTC

ATCAGCCCTCGATGCCGACATCCCCAGCGCAGATTTTTCCTTCAGCCAGG

GATGA

SEQ ID NO. 2 Coding sequence of wild type TaMLO-B1:1605 bp; The TALEN target site is indicated underlined.

ATGGCGGAGGACGACGGGTACCCCCCAGCGAGGACGCTGCCGGAGACGCC

GTCCTGGGCGGTGGCCCTCGTCTTCGCCGTCATGATCATCGTGTCCGTCC

TCCTGGAGCACGCGCTCCATAAGCTCGGCCAGTGGTTCCACAAGCGGCAC

AAGAACGCGCTGGCGGAGGCGCTGGAGAAGATCAAGGCGGAGCTCATGCT

GGTGGGCTTCATC<u>TCGCTGCTGCTCGCCGTGACGCAGGACCCCATCTCCG</u>

<u>GGATATGCATCTCCGA</u>GAAGGCCGCCAGCATCATGCGGCCCTGCAAGCTG

CCCCCTGGCTCCGTCAAGAGCAAGTACAAAGACTACTACTGCGCCAAACA

GGGCAAGGTGTCGCTCATGTCCACGGGCAGCTTGCACCAGCTGCACATAT

TCATCTTCGTGCTCGCCGTCTTCCATGTCACCTACAGCGTCATCATCATG

GCTCTAAGCCGTCTCAAGATGAGAACCTGGAAGAAATGGGAGACAGAGAC

CGCCTCCCTGGAATACCAGTTCGCAAATGATCCTGCGCGGTTCCGCTTCA

CGCACCAGACGTCGTTCGTGAAGCGGCACCTGGGCCTCTCCAGCACCCCC

GGCGTCAGATGGGTGGTGGCCTTCTTCAGGCAGTTCTTCAGGTCGGTCAC

CAAGGTGGACTACCTCACCTTGAGGGCAGGCTTCATCAACGCGCATTTGT

CGCATAACAGCAAGTTCGACTTCCACAAGTACATCAAGAGGTCCATGGAG

GACGACTTCAAAGTCGTCGTTGGCATCAGCCTCCCGCTGTGGTGTGTGGC

GATCCTCACCCTCTTCCTTGACATTGACGGGATCGGCACGCTCACCTGGA

TTTCTTTCATCCCTCTCGTCATCCTCTTGTGTGTTGGAACCAAGCTGGAG

ATGATCATCATGGAGATGGCCCTGGAGATCCAGGACCGGGCGAGCGTCAT

CAAGGGGGCGCCCGTGGTTGAGCCCAGCAACAAGTTCTTCTGGTTCCACC

GCCCCGACTGGGTCCTCTTCTTCATACACCTGACGCTATTCCAGAACGCG

TTTCAGATGGCACATTTCGTGTGGACAGTGGCCACGCCCGGCTTGAAGAA

ATGCTTCCATATGCACATCGGGCTGAGCATCATGAAGGTCGTGCTGGGGC

TGGCTCTTCAGTTCCTCTGCAGCTATATCACCTTCCCGCTCTACGCGCTC

GTCACACAGATGGGATCAAACATGAAGAGGTCCATCTTCGACGAGCAGAC

GGCCAAGGCGCTGACAAACTGGCGGAACACGGCCAAGGAGAAGAAGAAGG

TCCGAGACACGGACATGCTGATGGCGCAGATGATCGGCGACGCGACGCCC

AGCCGAGGGCGTCGCCCATGCCTAGCCGGGGCTCGTCGCCAGTGCACCT

GCTTCACAAGGGCATGGGACGGTCCGACGATCCCCAGAGCACGCCAACCT

CGCCAAGGGCCATGGAGGAGGCTAGGGACATGTACCCGGTTGTGGTGGCG

CATCCAGTGCACAGACTAAATCCTGCTGACAGGAGAAGGTCGGTCTCGTC

GTCGGCACTCGATGTCGACATTCCCAGCGCAGATTTTTCCTTCAGCCAGG

GATGA

SEQ ID NO. 3 Coding sequence of wild type TaMLO-D1:1605 bp; The TALEN target site is indicated underlined.

ATGGCGGAGGACGACGGGTACCCCCCGGCGCGGACGCTGCCGGAGACGCC

GTCCTGGGCGGTGGCGCTCGTCTTCGCCGTCATGATCATCGTGTCCGTCC

TCCTGGAGCACGCGCTCCACAAGCTCGGCCAGTGGTTCCACAAGCGGCAC

AAGAACGCGCTGGCGGAGGCGCTGGAGAAGATCAAAGCGGAGCTGATGCT

GGTGGGGTTCATC<u>TCGCTGCTGCTCGCCGTGACGCAGGACCCAATCTCCG</u>

<u>GGATATGCATCTCCGA</u>GAAGGCCGCCAGCATCATGCGGCCCTGCAGCCTG

CCCCCTGGTTCCGTCAAGAGCAAGTACAAAGACTACTACTGCGCCAAAAA

GGGCAAGGTGTCGCTAATGTCCACGGGCAGCTTGCACCAGCTCCACATAT

TCATCTTCGTGCTCGCCGTCTTCCATGTCACCTACAGCGTCATCATCATG

GCTCTAAGCCGTCTCAAGATGAGGACATGGAAGAAATGGGAGACAGAGAC

CGCCTCCTTGGAATACCAGTTCGCAAATGATCCTGCGCGGTTCCGCTTCA

CGCACCAGACGTCGTTCGTGAAGCGTCACCTGGGCCTCTCCAGCACCCCC

GGCATCAGATGGGTGGTGGCCTTCTTCAGGCAGTTCTTCAGGTCGGTCAC

CAAGGTGGACTACCTCACCCTGAGGGCAGGCTTCATCAACGCGCATTTGT

CGCATAACAGCAAGTTCGACTTCCACAAGTACATCAAGAGGTCCATGGAG

GACGACTTCAAAGTCGTCGTTGGCATCAGCCTCCCGCTGTGGTGTGTGGC

GATCCTCACCCTCTTCCTTGATATTGACGGGATCGGCACGCTCACCTGGA

TTTCTTTCATCCCTCTCGTCATCCTCTTGTGTGTTGGAACCAAGCTGGAG

ATGATCATCATGGAGATGGCCCTGGAGATCCAGGACCGGGCGAGCGTCAT

CAAGGGGGCGCCCGTGGTTGAGCCCAGCAACAAGTTCTTCTGGTTCCACC

GCCCCGACTGGGTCCTCTTCTTCATACACCTGACGCTGTTCCAGAATGCG

TTTCAGATGGCACATTTCGTCTGGACAGTGGCCACGCCCGGCTTGAAGAA

ATGCTTCCATATGCACATCGGGCTGAGCATCATGAAGGTCGTGCTGGGGC

TGGCTCTTCAGTTCCTCTGCAGCTATATCACCTTCCCGCTCTACGCGCTC

GTCACACAGATGGGATCAAACATGAAGAGGTCCATCTTCGACGAGCAGAC

GGCCAAGGCGCTGACAAACTGGCGGAACACGGCCAAGGAGAAGAAGAAGG

TCCGAGACACGGACATGCTGATGGCGCAGATGATCGGCGACGCGACGCCC

AGCCGAGGGCGTCGCCCATGCCTAGCCGGGGCTCGTCGCCAGTGCACCT

GCTTCACAAGGGCATGGGACGGTCCGACGATCCCCAGAGCACGCCAACCT

CGCCAAGGGCCATGGAGGAGGCTAGGGACATGTACCCGGTTGTGGTGGCG

CATCCAGTGCACAGACTAAATCCTGCTGACAGGAGAAGGTCGGTCTCTTC

GTCGGCACTCGATGCCGACATCCCCAGCGCAGATTTTTCCTTCAGCCAGG

GATGA

SEQ ID NO. 4 The amino acid sequence of wild type TAMLO-A1:534aa

MAEDDGYPPARTLPETPSWAVALVFAVMIIVSVLLEHALHKLGQWFHKRH

KNALAEALEKMKAELMLVGFISLLLAVTQDPISGICISQKAASIMRPCKV

EPGSVKSKYKDYYCAKEGKVALMSTGSLHQLHIFIFVLAVFHVTYSVIIM

ALSRLKMRTWKKWETETASLEYQFANDPARFRFTHQTSFVKRHLGLSSTP

GVRWVVAFFRQFFRSVTKVDYLTLRAGFINAHLSQNSKFDFHKYIKRSME

DDFKVVVGISLPLWAVAILTLFLDIDGIGTLTWVSFIPLIILLCVGTKLE

MIIMEMALEIQDRSSVIKGAPVVEPSNKFFWFHRPDWVLFFIHLTLFQNA

FQMAHFVWTVATPGLKDCFHMNIGLSIMKVVLGLALQFLCSYITFPLYAL

VTQMGSNMKRSIFDEQTAKALTNWRNTAKEKKKVRDTDMLMAQMIGDATP

SRGTSPMPSRGSSPVHLLQKGMGRSDDPQSAPTSPRTMEEARDMYPVVVA

HPVHRLNPADRRRSVSSSALDADIPSADFSFSQG

SEQ ID NO. 5 The amino acid sequence of wild type TaMLO-B1: 534aa.

MAEDDGYPPARTLPETPSWAVALVFAVMIIVSVLLEHALHKLGQWFHKRH

KNALAEALEKIKAELMLVGFISLLLAVTQDPISGICISEKAASIMRPCKL

PPGSVKSKYKDYYCAKQGKVSLMSTGSLHQLHIFIFVLAVFHVTYSVIIM

ALSRLKMRTWKKWETETASLEYQFANDPARFRFTHQTSFVKRHLGLSSTP

GVRWVVAFFRQFFRSVTKVDYLTLRAGFINAHLSHNSKFDFHKYIKRSME

DDFKVVVGISLPLWCVAILTLFLDIDGIGTLTWISFIPLVILLCVGTKLE

MIIMEMALEIQDRASVIKGAPVVEPSNKFFWFHRPDWVLFFIHLTLFQNA

FQMAHFVWTVATPGLKKCFHMHIGLSIMKVVLGLALQFLCSYITFPLYAL

VTQMGSNMKRSIFDEQTAKALTNWRNTAKEKKKVRDTDMLMAQMIGDATP

SRGASPMPSRGSSPVHLLHKGMGRSDDPQSTPTSPRAMEEARDMYPVVVA

HPVHRLNPADRRRSVSSSALDVDIPSADFSFSQG

SEQ ID NO. 6 The amino acid sequence of wild type TaMLO-D1: 534aa

MAEDDGYPPARTLPETPSWAVALVFAVMIIVSVLLEHALHKLGQWFHKRH

KNALAEALEKIKAELMLVGFISLLLAVTQDPISGICISEKAASIMRPCSL

PPGSVKSKYKDYYCAKKGKVSLMSTGSLHQLHIFIFVLAVFHVTYSVIIM

ALSRLKMRTWKKWETETASLEYQFANDPARFRFTHQTSFVKRHLGLSSTP

GIRWVVAFFRQFFRSVTKVDYLTLRAGFINAHLSHNSKFDFHKYIKRSME

DDFKVVVGISLPLWCVAILTLFLDIDGIGTLTWISFIPLVILLCVGTKLE

MIIMEMALEIQDRASVIKGAPVVEPSNKFFWFHRPDWVLFFIHLTLFQNA

FQMAHFVWTVATPGLKKCFHMHIGLSIMKVVLGLALQFLCSYITFPLYAL

VTQMGSNMKRSIFDEQTAKALTNWRNTAKEKKKVRDTDMLMAQMIGDATP

SRGASPMPSRGSSPVHLLHKGMGRSDDPQSTPTSPRAMEEARDMYPVVVA

HPVHRLNPADRRRSVSSSALDADIPSADFSFSQG

SEQ ID NO. 11 The coding sequence of TALENs (TAL-L+TAL-R) in vector pYP010.

ATGGTGGATCTACGCACGCTCGGCTACAGTCAGCAGCAGCAAGAGAAGAT

CAAACCGAAGGTGCGTTCGACAGTGGCGCAGCACCACGAGGCACTGGTGG

GCCATGGGTTTACACACGCGCACATCGTTGCGCTCAGCCAACACCCGGCA

GCGTTAGGGACCGTCGCTGTCACGTATCAGCACATAATCACGGCGTTGCC

AGAGGCGACACACGAAGACATCGTTGGCGTCGGCAAACAGTGGTCCGGCG

CACGCGCCCTGGAGGCCTTGCTCACGGATGCGGGGGAGTTGAGAGGTCCG

```
CCGTTACAGTTGGACACAGGCCAACTTGTGAAGATTGCAAAACGTGGCGG
CGTGACCGCAATGGAGGCAGTGCATGCATCGCGCAATGCACTGACGGGTG
CCCCCCTGAACCTGACCCCGGACCAAGTGGTGGCTATCGCCAGCCACGAT
GGCGGCAAGCAAGCGCTCGAAACGGTGCAGCGGCTGTTGCCGGTGCTGTG
CCAGGACCATGGCCTGACCCCGGACCAAGTGGTGGCTATCGCCAGCAACA
ATGGCGGCAAGCAAGCGCTCGAAACGGTGCAGCGGCTGTTGCCGGTGCTG
TGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGC
TGTGCCAGGACCATGGCCTGACCCCGGACCAAGTGGTGGCTATCGCCAGC
AACGGTGGCGGCAAGCAAGCGCTCGAAACGGTGCAGCGGCTGTTGCCGGT
GCTGTGCCAGGACCATGGCCTGACCCCGGACCAAGTGGTGGCTATCGCCA
GCAACAATGGCGGCAAGCAAGCGCTCGAAACGGTGCAGCGGCTGTTGCCG
GTGCTGTGCCAGGACCATGGCCTGACTCCGGACCAAGTGGTGGCTATCGC
CAGCCACGATGGCGGCAAGCAAGCGCTCGAAACGGTGCAGCGGCTGTTGC
CGGTGCTGTGCCAGGACCATGGCCTGACCCCGGACCAAGTGGTGGCTATC
GCCAGCAACGGTGGCGGCAAGCAAGCGCTCGAAACGGTGCAGCGGCTGTT
GCCGGTGCTGTGCCAGGACCATGGCCTGACCCCGGACCAAGTGGTGGCTA
TCGCCAGCAACAATGGCGGCAAGCAAGCGCTCGAAACGGTGCAGCGGCTG
TTGCCGGTGCTGTGCCAGGACCATGGCCTGACTCCGGACCAAGTGGTGGC
TATCGCCAGCCACGATGGCGGCAAGCAAGCGCTCGAAACGGTGCAGCGGC
TGTTGCCGGTGCTGTGCCAGGACCATGGCCTGACCCCGGACCAAGTGGTG
GCTATCGCCAGCAACGGTGGCGGCAAGCAAGCGCTCGAAACGGTGCAGCG
GCTGTTGCCGGTGCTGTGCCAGGACCATGGCCTGACCCCGGACCAAGTGG
TGGCTATCGCCAGCCACGATGGCGGCAAGCAAGCGCTCGAAACGGTGCAG
CGGCTGTTGCCGGTGCTGTGCCAGGACCATGGCCTGACCCCGGACCAAGT
GGTGGCTATCGCCAGCAACAATGGCGGCAAGCAAGCGCTCGAAACGGTGC
AGCGGCTGTTGCCGGTGCTGTGCCAGGACCATGGCCTGACTCCGGACCAA
GTGGTGGCTATCGCCAGCCACGATGGCGGCAAGCAAGCGCTCGAAACGGT
GCAGCGGCTGTTGCCGGTGCTGTGCCAGGACCATGGCCTGACTCCGGACC
AAGTGGTGGCTATCGCCAGCCACGATGGCGGCAAGCAAGCGCTCGAAACG
GTGCAGCGGCTGTTGCCGGTGCTGTGCCAGGACCATGGCCTGACCCCGGA
CCAAGTGGTGGCTATCGCCAGCAACAATGGCGGCAAGCAAGCGCTCGAAA
CGGTGCAGCGGCTGTTGCCGGTGCTGTGCCAGGACCATGGCCTGACCCCG
GACCAAGTGGTGGCTATCGCCAGCAACGGTGGCGGCAAGCAAGCGCTCGA
AAGCATTGTGGCCCAGCTGAGCCGGCCTGATCCGGCGTTGGCCGCGTTGA
CCAACGACCACCTCGTCGCCTTGGCCTGCCTCGGCGGACGTCCTGCCATG
GATGCAGTGAAAAAGGGATTGCCGCACGCGCCGGAATTGATCAGAAGAGT
CAATCGCCGTATTGGCGAACGCACGTCCCATCGCGTTGCCGGATCCCAGC
TGGTGAAGTCCGAGCTGGAAGAAAAAAAGAGCGAGCTGCGCCACAAGCTC
AAGTACGTGCCCCACGAGTACATCGAGCTGATCGAGATCGCCCGCAACAG
CACCCAAGACCGCATCCTGGAGATGAAAGTGATGGAGTTCTTCATGAAGG
TGTACGGCTACCGCGGCAAGCACCTGGGCGGCTCCCGCAAGCCCGATGGC
GCCATCTACACCGTGGGCTCCCCCATCGACTATGGCGTCATTGTCGACAC
CAAGGCCTACTCCGGCGGCTACAACTTACCCATCGGTCAGGCCGACGAGA
TGCAACGCTACGTGAAGGAGAACCAGACCCGCAATAAGCACATTAATCCC
AACGAGTGGTGGAAGGTGTACCCCTCCTCCGTGACCGAGTTCAAATTCCT
GTTCGTGTCCGGCCACTTCAAGGGCAATTATAAGGCCCAACTGACCCGCC
TGAACCACAAGACCAACTGCAACGGCGCCGTGCTGTCCGTGGAGGAACTG
CTGATCGGCGGCGAGATGATCAAGGCTGGTACCCTGACCCTGGAAGAGGT
GCGCCCAAGTTCAACAATGGTGAAATCAATTTCAGGTCCGGCGGCGGAG
AGGGCAGAGGAAGTCTTCTAACATGCGGTGACGTGGAGGAGAATCCCGGC
CCTAGGATGGACTACAAAGACCATGACGGTGATTATAAAGATCATGACAT
CGATTACAAGGATGACGATGACAAGATGGCCCCCAAGAAGAAGAGGAAGG
TGGGCATTCACGGGGTGCCGGCTAGCATGGTGGATCTACGCACGCTCGGC
TACAGTCAGCAGCAGCAAGAGAAGATCAAACCGAAGGTGCGTTCGACAGT
GGCGCAGCACCACGAGGCACTGGTGGGCCATGGGTTTACACACGCGCACA
TCGTTGCGCTCAGCCAACACCCGGCAGCGTTAGGGACCGTCGCTGTCACG
TATCAGCACATAATCACGGCGTTGCCAGAGGCGACACACGAAGACATCGT
TGGCGTCGGCAAACAGTGGTCCGGCGCACGCGCCCTGGAGGCCTTGCTCA
CGGATGCGGGGAGTTGAGAGGTCCGCCGTTACAGTTGGACACAGGCCAA
CTTGTGAAGATTGCAAAACGTGGCGGCGTGACCGCAATGGAGGCAGTGCA
TGCATCGCGCAATGCACTGACGGGTGCCCCCCTGAACCTGACCCCGGACC
AAGTGGTGGCTATCGCCAGCAACAAGGGCGGCAAGCAAGCGCTCGAAACG
GTGCAGCGGCTGTTGCCGGTGCTGTGCCAGGACCATGGCCTGACCCCGGA
CCAAGTGGTGGCTATCGCCAGCAACAAGGGCGGCAAGCAAGCGCTCGAAA
CGGTGCAGCGGCTGTTGCCGGTGCTGTGCCAGGACCATGGCCTGACCCCG
GACCAAGTGGTGGCTATCGCCAGCAACAAGGGCGGCAAGCAAGCGCTCGA
AACGGTGCAGCGGCTGTTGCCGGTGCTGTGCCAGGACCATGGCCTGACCC
CGGACCAAGTGGTGGCTATCGCCAGCAACATTGGCGGCAAGCAAGCGCTC
GAAACGGTGCAGCGGCTGTTGCCGGTGCTGTGCCAGGACCATGGCCTGAC
CCCGGACCAAGTGGTGGCTATCGCCAGCAACAAGGGCGGCAAGCAAGCGC
TCGAAACGGTGCAGCGGCTGTTGCCGGTGCTGTGCCAGGACCATGGCCTG
ACCCCGGACCAAGTGGTGGCTATCGCCAGCAACATTGGCGGCAAGCAAGC
GCTCGAAACGGTGCAGCGGCTGTTGCCGGTGCTGTGCCAGGACCATGGCC
TGACCCCGGACCAAGTGGTGGCTATCGCCAGCAACGGTGGCGGCAAGCAA
GCGCTCGAAACGGTGCAGCGGCTGTTGCCGGTGCTGTGCCAGGACCATGG
CCTGACCCCGGACCAAGTGGTGGCTATCGCCAGCAACAAGGGCGGCAAGC
AAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAA
GCAAGCGCTCGAAACGGTGCAGCGGCTGTTGCCGGTGCTGTGCCAGGACC
ATGGCCTGACCCCGGACCAAGTGGTGGCTATCGCCAGCAACATTGGCGGC
```

-continued

```
AAGCAAGCGCTCGAAACGGTGCAGCGGCTGTTGCCGGTGCTGTGCCAGGA
CCATGGCCTGACCCCGGACCAAGTGGTGGCTATCGCCAGCAACGGTGGCG
GCAAGCAAGCGCTCGAAACGGTGCAGCGGCTGTTGCCGGTGCTGTGCCAG
GACCATGGCCTGACCCCGGACCAAGTGGTGGCTATCGCCAGCAACATTGG
CGGCAAGCAAGCGCTCGAAACGGTGCAGCGGCTGTTGCCGGTGCTGTGCC
AGGACCATGGCCTGACCCCGGACCAAGTGGTGGCTATCGCCAGCAACGGT
GGCGGCAAGCAAGCGCTCGAAACGGTGCAGCGGCTGTTGCCGGTGCTGTG
CCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTG
TGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGC
TGTGCCAGGACCATGGCCTGACTCCGGACCAAGTGGTGGCTATCGCCAGC
CACGATGGCGGCAAGCAAGCGCTCGAAACGGTGCAGCGGCTGTTGCCGGT
GCTGTGCCAGGACCATGGCCTGACCCCGGACCAAGTGGTGGCTATCGCCA
GCAACAAGGGCGGCAAGCAAGCGCTCGAAAGCATTGTGGCCCAGCTGAGC
CGGCCTGATCCGGCGTTGGCCGCGTTGACCAACGACCACCTCGTCGCCTT
GGCCTGCCTCGGCGGACGTCCTGCCATGGATGCAGTGAAAAAGGGATTGC
CGCACGCGCCGAATTGATCAGAAGAGTCAATCGCCGTATTGGCGAACGC
ACGTCCCATCGCGTTGCCAGATCTCAACTAGTCAAAAGTGAACTGGAGGA
GAAGAAATCTGAACTTCGTCATAAAATTGAAATATGTGCCTCATGAATATA
TTGAATTAATTGAAATTGCCAGAAATTCCACTCAGGATAGAATTCTTGAA
ATGAAGGTAATGGAATTTTTTATGAAAGTTTATGGATATAGAGGTAAACA
TTTGGGTGGATCAAGGAAACCGGACGGAGCAATTTATACTGTCGGATCTC
CTATTGATTACGGTGTGATCGTGGATACTAAAGCTTATAGCGGAGGTTAT
AATCTGCCAATTGGCCAAGCAGATGAAATGGAGCGATATGTCGAAGAAAA
TCAAACACGAAACAAACATCTCAACCCTAATGAATGGTGGAAAGTCTATC
CATCTTCTGTAACGGAATTTAAGTTTTTATTTGTGAGTGGTCACTTTAAA
GGAAACTACAAAGCTCAGCTTACACGATTAAATCATATCACTAATTGTAA
TGGAGCTGTTCTTAGTGTAGAAGAGCTTTTAATTGGTGGAGAAATGATTA
AAGCCGGCACATTAACCTTAGAGGAAGTGAGACGGAAATTTAATAACGGC
GAGATAAACTTTTAATAG
```

SEQ ID NO. 12 The amino acid sequence of the TALENs.

```
MVDLRTLGYSQQQQEKIKPKVRSTVAQHHEALVGHGFTHAHIVALSQHPA
ALGTVAVTYQHIITALPEATHEDIVGVGKQWSGARALEALLTDAGELRGP
PLQLDTGQLVKIAKRGGVTAMEAVHASRNALTGAPLNLTPDQVVAIASHD
GGKQALETVQRLLPVLCQDHGLTPDQVVAIASNNGGKQALETVQRLLPVL
CQDHGLTPDQVVAIASHDGGKQALETVQRLLPVLCQDHGLTPDQVVAIAS
NGGGKQALETVQRLLPVLCQDHGLTPDQVVAIASNNGGKQALETVQRLLP
VLCQDHGLTPDQVVAIASHDGGKQALETVQRLLPVLCQDHGLTPDQVVAI
ASNGGGKQALETVQRLLPVLCQDHGLTPDQVVAIASNNGGKQALETVQRL
LPVLCQDHGLTPDQVVAIASHDGGKQALETVQRLLPVLCQDHGLTPDQVV
AIASNGGGKQALETVQRLLPVLCQDHGLTPDQVVAIASHDGGKQALETVQ
RLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALET
VQRLLPVLCQDHGLTPDQVVAIASNNGGKQALETVQRLLPVLCQDHGLTP
DQVVAIASNGGGKQALESIVAQLSRPDPALAALTNDHLVALACLGGRPAM
DAVKKGLPHAPELIRRVNRRIGERTSHRVAGSQLVKSELEEKKSELRHKL
KYVPHEYIELIEIARNSTQDRILEMKVMEFFMKVYGYRGKHLGGSRKPDG
AIYTVGSPIDYGVIVDTKAYSGGYNLPIGQADEMQRYVKENQTRNKHINP
NEWWKVYPSSVTEFKFLFVSGHFKGNYKAQLTRLNHKTNCNGAVLSVEEL
LIGGEMIKAGTLTLEEVRRKFNNGEINFRSGGGEGRGSLLTCGDVEENPG
PRMDYKDHDGDYKDHDIDYKDDDDKMAPKKKRKVGIHGVPASMVDLRTLG
YSQQQQEKIKPKVRSTVAQHHEALVGHGFTHAHIVALSQHPAALGTVAVT
YQHIITALPEATHEDIVGVGKQWSGARALEALLTDAGELRGPPLQLDTGQ
LVKIAKRGGVTAMEAVHASRNALTGAPLNLTPDQVVAIASNKGGKQALET
VQRLLPVLCQDHGLTPDQVVAIASNKGGKQALETVQRLLPVLCQDHGLTP
DQVVAIASNKGGKQALETVQRLLPVLCQDHGLTPDQVVAIASNIGGKQAL
ETVQRLLPVLCQDHGLTPDQVVAIASNKGGKQALETVQRLLPVLCQDHGL
TPDQVVAIASNIGGKQALETVQRLLPVLCQDHGLTPDQVVAIASNGGGKQ
ALETVQRLLPVLCQDHGLTPDQVVAIASNKGGKQALETVQRLLPVLCQDH
GLTPDQVVAIASHDGGKQALETVQRLLPVLCQDHGLTPDQVVAIASNIGG
KQALETVQRLLPVLCQDHGLTPDQVVAIASNGGGKQALETVQRLLPVLCQ
DHGLTPDQVVAIASNIGGKQALETVQRLLPVLCQDHGLTPDQVVAIASNG
GGKQALETVQRLLPVLCQDHGLTPDQVVAIASHDGGKQALETVQRLLPVL
CQDHGLTPDQVVAIASHDGGKQALETVQRLLPVLCQDHGLTPDQVVAIAS
HDGGKQALETVQRLLPVLCQDHGLTPDQVVAIASNKGGKQALESIVAQLS
RPDPALAALTNDHLVALACLGGRPAMDAVKKGLPHAPELIRRVNRRIGER
TSHRVARSQLVKSELEEKKSELRHKLKYVPHEYIELIEIARNSTQDRILE
MKVMEFFMKVYGYRGKHLGGSRKPDGAIYTVGSPIDYGVIVDTKAYSGGY
NLPIGQADEMERYVEENQTRNKHLNPNEWWKVYPSSVTEFKFLFVSGHFK
GNYKAQLTRLNHITNCNGAVLSVEELLIGGEMIKAGTLTLEEVRRKFNNG
EINF
```

Nucleic acid sequence of Tamlo-A in line Tamlo-R32 (coding sequence) SEQ ID NO. 38

```
  1   ATGGCGGAGG ACGACGGGTA CCCCCCGGCG CGGACGCTGC GGAGACGCC GTCCTGGGCG
 61   GTGGCGCTGG TCTTCGCCGT CATGATCATC GTCTCCGTCC TCCTGGAGCA CGCGCTCCAC
```

-continued

```
 121  AAGCTCGGCC ATGTAAGTCC CCTCACTCCC GCAACAAGAA CAAGAACAAG AACAAGAACA
 181  ACCAGAACCA GAATCAGCTC ATGGCTTCCT TTCCTCCCTT GGTGCGTGTA AGCAGTGGTT
 241  CCACAAGCGG CACAAGAACG CGCTGGCGGA GGCGCTGGAG AAGATGAAGG CGGAGCTGAT
 301  GCTGGTGGGA TTCATCTCGC TGCTGCTCGC CGTCACGCGA AGGTGACCGC GGTGATGATG
 361  ATGATGATGG AACTTGTTCT CGCCCGTGGT GACCCAATCT CCGGGATATG CATCTCCCAG
 421  AAGGCCGCCA GCATCATGCG CCCCTGCAAG GTGGAACCCG GTTCCGTCAA GAGCAAGTAC
 481  AAGGACTACT ACTGCGCCAA AGAGGTAACT AACACAAACA GTTTCTTCTT CTTCTTGTTG
 541  TTTTCCTTCC TGATTGGCTT GGCCTGATTG GTGTGGTGTC TGTTTCTCCT GCAGGGCAAG
 601  GTGGCGCTCA TGTCCACGGG CAGCCTGCAC CAGCTCCACA TATTCATCTT CGTGCTAGCC
 661  GTCTTCCATG TCACCTACAG CGTCATCATC ATGGCTCTAA GCCGTCTCAA GGTGAGCCTT
 721  TCTTTCTTTC TTTCCCGTGC TTCCAGATCC TGCGCGGTTC CCGGGCAAGG TGGCGCTCAT
 781  CGTACGTCTG TCTCAGTTAA ACTGCTACCA ATCCTTAACC TGCTCCGGCA TAATATTCTT
 841  ATTCCTCCCC CCGGCAGATG AGAACATGGA AGAAATGGGA GACAGAGACC GCCTCCTTGG
 901  AATACCAGTT CGCAAATGGT CAGACAATTT TCCAAATGAA ACCTCTTCTG TTTTGATGCG
 961  TTTACAGAGG CAGGCATGAT CAGAGCGAGT GAACTGATGA TATGTTCTTC TCTTTCCCGT
1021  GCTTCCAGAT CCTGCGCGGT TCCGCTTCAC GCACCAGACG TCGTTCGTGA AGCGGCACCT
1081  GGGCCTGTCC AGCACCCCCG GCGTCAGATG GGTGGTGGCC TTCTTCAGGC AGTTCTTCAG
1141  GTCGGTCACC AAGGTGGACT ACCTCACCTT GAGGGCAGGC TTCATCAACG TACGTAATAC
1201  CCCAAAAGCC CCCTCTCCTT CTAGCTCCGT CGGCCATTGC CGCGACGCTT CTGAAATAAG
1261  TACTGTTCCA ACACCAATGA TCACATGCTC TCTCTTTCCA TGATTCTGCG CAGGCGCACT
1321  TGTCGCAGAA CAGCAAGTTC GACTTCCACA AGTACATCAA GAGGTCCATG GAGGACGACT
1381  TCAAAGTCGT CGTTGGCATC AGGTAGGTTG CATTCCATGG ATATGATTAT ACAATTGTCG
1441  TCAGGCTCCA TATGATATTG CTTAGCTTCC ATATGATACA ATACTATCAG TTTGCTGCGT
1501  CATGGTCTTT GCCCCTGCTG GTCCTTGTTG CATGATCTTG ACACATTTGG CCTCTTTTCG
1561  CAGCCTCCCG CTGTGGGCTG TGGCGATCCT CACCCTCTTC CTTGATATCG ACGGTATGGA
1621  CCTTGTCTTT GCCCCCTTCT CTGTTGCCTT GCTGCTAAAA CACTTGTAAT TTATTTGTCT
1681  CGTAACCACC GTTCATTTTC TAACCTTTCC CCCCTTTCTT TCTGCTCATA GGGATCGGCA
1741  CACTCACCTG GGTTTCTTTC ATCCCTCTCA TCGTAAGTGC GAATTTCTCC GCCGAAAGCA
1801  ACAGCCAAAC CCCATTTGAT TGCAATGCGA AATCACACCT AATAATAATT CAAATTGTCA
1861  TTGTCCATCT GTCTTTCCCA GATCCTCTTG TGTGTTGGAA CCAAGCTAGA GATGATCATC
1921  ATGGAGATGG CCCTGGAGAT CCAGGACCGG TCGAGCGTCA TCAAGGGGGC ACCCGTGGTC
1981  GAGCCCAGCA ACAAGTTCTT CTGGTTCCAC CGCCCCGACT GGGTCCTCTT CTTCATACAC
2041  CTGACGCTGT TCCAGAACGC GTTTCAGATG GCACATTTCG TGTGGACAGT GGTACGCCGC
2101  GGATGAACTT GTCAGTTAAT AATATGGGTG TCAAGGCACC AAGTGCTGCT GCTGATGAAC
2161  TGCACTGACA GAGATTTACC TGTGTCGCAG GCCACGCCCG GCTTGAAGGA CTGCTTCCAT
2221  ATGAACATCG GGCTGAGCAT CATGAAGGTC GTGCTGGGGC TGGCTCTCCA GTTCCTGTGC
2281  AGCTACATCA CCTTCCCCCT CTACGCGCTA GTCACACAGG TAATAAAACC GTTGATGAAG
2341  ATCTCTGAAC AATTGCTCTG GGAGAGGAGA AACAGCAGCC TTAATCATCT GTGTGCGCTG
2401  GCTTTGTACG CAGATGGGAT CAAACATGAA GAGGTCCATC TTCGACGAGC AGACAGCCAA
2461  GGCGCTGACC AACTGGCGGA ACACGGCCAA GGAGAAGAAG AAGGTCCGAG ACACGGACAT
```

-continued

```
2521   GCTGATGGCG CAGATGATCG GCGACGCAAC ACCCAGCCGA GGCACGTCCC CGATGCCTAG

2581   CCGGGGCTCA TCGCCGGTGC ACCTGCTTCA GAAGGGCATG GGACGGTCTG ACGATCCCCA

2641   GAGCGCACCG ACCTCGCCAA GGACCATGGA GGAGGCTAGG GACATGTACC CGGTTGTGGT

2701   GGCGCATCCT GTACACAGAC TAAATCCTGC TGACAGGAGA AGGTCGGTCT CTTCATCAGC

2761   CCTCGATGCC GACATCCCCA GCGCAGATTT TTCCTTCAGC CAGGGATGA
```

Nucleic acid sequence of Tamlo-D1 in line Tamlo-R32[10] (coding sequence) SEQ ID NO. 39

```
   1   ATGGCGGAGG ACGACGGGTA CCCCCCGGCG CGGACGCTGC CGGAGACGCC GTCCTGGGCG

61   GTGGCGCTCG TCTTCGCCGT CATGATCATC GTGTCCGTCC TCCTGGAGCA CGCGCTCCAC

121   AAGCTCGGCC ATGTAAGTTC CCTCACTCCT GCAACAAGAA AAAAAAAGC CTCAACCAGA

181   ATCAGCAGCT CAGCTCATGG CTTCCTCTGC TCCCTTGGTG CACCTGCAGT GGTTCCACAA

241   GCGGCACAAG AACGCGCTGG CGGAGGCGCT GGAGAAGATC AAAGCGGAGC TGATGCTGGT

301   GGGGTTCATC TCGCTGCTGC TCCATCTCCG AGAAGGCCGC CAGCATCATG CGGCCCTGCA

361   GCCTGCCCCC TGGTTCCGTC AAGAGCAAGT ACAAAGACTA CTACTGCGCC AAAAAGGTGA

421   GCCTGCTACA AGCTACTCCC GGAGACGGCC GGGAAAAACA CAAACAGATT CCGGCGGCCG

481   GCCGGAGTTT CTTCTTGTTT CCTTCCTGAT TGGCTTGGCC TAATTGGTGT GTGTTTTTCT

541   GGCAGGGCAA GGTGTCGCTA ATGTCCACGG GCAGCTTGCA CCAGCTCCAC ATATTCATCT

601   TCGTGCTCGC CGTCTTCCAT GTCACCTACA GCGTCATCAT CATGGCTCTA AGCCGTCTCA

661   AAGTGAGTCT GTCAGGCCTA CCTGTTCATG CTTCGGTAAA GCAATAAAAC TACTTGCTAC

721   CAATCCCTAA TCTGCTCCCT CAGGCATAAT ATTGTTCCTT CTTTCCTGCT GCAGATGAGG

781   ACATGGAAGA AATGGGAGAC AGAGACCGCC TCCTTGGAAT ACCAGTTCGC AAATGGTCAG

841   ACAATTTCCG AAATGAAACC TGACTGATGC ATTTACAAAC GCACGCAGGC AGGCATGATC

901   AGAGTGAGTG AACTGATGAT ATGTTTTCTC TCTCTTTCCC GTGCCTCCAG ATCCTGCGCG

961   GTTCCGCTTC ACGCACCAGA CGTCGTTCGT GAAGCGTCAC CTGGGCCTCT CCAGCACCCC

1021   CGGCATCAGA TGGGTGGTGG CCTTCTTCAG GCAGTTCTTC AGGTCGGTCA CCAAGGTGGA

1081   CTACCTCACC CTGAGGGCAG GCTTCATCAA CGTACGTACC AAAACAAATC CTCTCCCTCT

1141   AGCTTCGCCA TTGCTGCGAC GCTTCTGAAA TATGTACCGT TCCGACACCA GCGATCTCAT

1201   GTCTTCTCTT TCCACGATTC TGCGCAGGCG CATTTGTCGC ATAACAGCAA GTTCGACTTC

1261   CACAAGTACA TCAAGAGGTC CATGGAGGAC GACTTCAAAG TCGTCGTTGG CATCAGGTAG

1321   GTTACATTCC ATGGATAGGA TTATAAAATT GCCGTCAGGC TCCATATGAT ATTGCTTAGG

1381   TTCCACATGA TACAATACTA TCAGTTTGCT GCGTCATGGT CTTTGCCCCT GCTGGTCTTC

1441   CTTGCGTGAT CTTGACACAT TTGGCCTCTT TTCGCAGCCT CCCGCTGTGG TGTGTGGCGA

1501   TCCTCACCCT CTTCCTTGAT ATTGACGGTA TGGACCTTGC TAAAACACTT GTAATTTGTC

1561   TCGTAACCAC CGTTCATTTT CTAACCTTCC TTTCCCCTTC TTTCTGCTGG CAGGGATCGG

1621   CACGCTCACC TGGATTTCTT TCATCCCTCT CGTCGTAAGT GCGAATTTCT CCGCCGAAAG

1681   CAACAGCCAG CCCCATTTGA TTGCAATGCG AAACCACACC TTAATTGAAA ATGTCATTGT

1741   CTGTCTTGTC TTTCTCAGAT CCTCTTGTGT GTTGGAACCA AGCTGGAGAT GATCATCATG

1801   GAGATGGCCC TGGAGATCCA GGACCGGGCG AGCGTCATCA AGGGGCGCC CGTGGTTGAG

1861   CCCAGCAACA AGTTCTTCTG GTTCCACCGC CCCGACTGGG TCCTCTTCTT CATACACCTG

1921   ACGCTGTTCC AGAATGCGTT TCAGATGGCA CATTTCGTCT GGACAGTGGT ATGTACCAGT
```

```
                          -continued
1981   AATTGGCAGT TCAGTTAGGG ATGCAAGGCA CCAAGTAGTG CTGATGAACT GCACTGACGG

2041   AGATTTACTT GTTCGTAGGC CACGCCCGGC TTGAAGAAAT GCTTCCATAT GCACATCGGG

2101   CTGAGCATCA TGAAGGTCGT GCTGGGGCTG GCTCTTCAGT TCCTCTGCAG CTATATCACC

2161   TTCCCGCTCT ACGCGCTCGT CACACAGGTA ATAAAGCCGT TGATGAAGAT GTCTGAACAA

2221   TTGCTCTGGG AGAGGAGAAA CAGCAGCCTT AATCATGTAA TCGGTGTGAT GGGTTGCAGA

2281   TGGGATCAAA CATGAAGAGG TCCATCTTCG ACGAGCAGAC GGCCAAGGCG CTGACAAACT

2341   GGCGGAACAC GGCCAAGGAG AAGAAGAAGG TCCGAGACAC GGACATGCTG ATGGCGCAGA

2401   TGATCGGCGA CGCGACGCCC AGCCGAGGGG CGTCGCCCAT GCCTAGCCGG GGCTCGTCGC

2461   CAGTGCACCT GCTTCACAAG GGCATGGGAC GGTCCGACGA TCCCCAGAGC ACGCCAACCT

2521   CGCCAAGGGC CATGGAGGAG CTAGGGACA TGTACCCGGT TGTGGTGGCG CATCCAGTGC

2581   ACAGACTAAA TCCTGCTGAC AGGAGAAGGT CGGTCTCTTC GTCGGCACTC GATGCCGACA

2641   TCCCCAGCGC AGATTTTTCC TTCAGCCAGG GATGA
```

Tamlo-R32-A upstream sequence (~3000 bp); ATG start codon in bold and underlined SEQ ID NO. 40

```
   1   GTGCGCCACT GCTATATAGC AGTGGCGCAC CACCATCATG GTGCGCCACT AATAGGGATA

61   TTGGCTATAG CCATTTTTCT AGTAGTGTAA GCACAAGAAA TAAAAAAAAT ATGGAAAACC

121   CTCACATCTC ATCTTAAATT CTCAGAGTTA GTAATACGAA ATTCAACGCA AATCAGGGAG

181   TAGGACAACG AGACGAAAGT GATTCCCCCG TAGCTCTTTT ATTTCGCGAG GGCTCTGATC

241   ATGTATAGCT AGCCATGCAT AGACAACATG ACAGGCATGT TTTGGGTGCC CACAGCACAC

301   ACAAGTTGTG AAACAGTACG TGCATGACTG GGCACAGAGC AGGTTAGAGC AAACCTCCAC

361   ATCACCATAA ATTCCGAGTA GCCACTAGAT TCAGCATGCC TGTTTAGGGT TCTGTACAGT

421   ACGTACCTGG CTACTACTGC TTGCCAATTG AAAAATGATT TAGAGCAAAT TCCAGAATGC

481   CATGACACAT CTGCTTTTAT GTCAAACCCA CTGTTCATAA CAATATTTGT GCGGTGGTGT

541   GCATGAGATA AGATCCGGAT GAGGGTGGCG CCCATAAAAA ATGGGCCATT CATGAACCAG

601   CAGCGTCAAC ACGAACGAGC GACGAAGCCG CGGGCTACGA GCGTCACCAC ACAATATGTT

661   AATGGATCGG GCCGGCCATC CCATCGGCCA TCAGGGTGTG CTGCCAAGCA GATCTCCATG

721   CATGATGCAT CACGGGTGCA CCTAGTAGCC ACATAGATCT CCAGACTCCA GGCATGATGC

781   ATCACGGGTG CATCTGTATA TTCAAACCTA CCATTAACTT TGCCCGATCA GAGGAACCGG

841   TCCGGATCCG ATCGTTAATT CGGCGACCAG TGACTTGATC GCGTCTGTTT AAGCACTAGC

901   AGCTCACTGA TCGCATGGAT CGACCGCTGG TAAGAATAGT ACACCCTGTG CATATACAAG

961   TCCGCGAAAA AGTAGCAGCC ACGAATGCAG TCAACGTTTT TATTTGACCT GACTCGCTCG

1021   ATCAGGCCCG TACTCCACTG GTTGAAACGC CCACTTCGCC GGAGCCGCCT GGTCAGACTT

1081   TTCCACGCAC GACCGACCAT TGAGCAGTCA AAGTTCGGAT GCCACGCCGT CGCTCGCATG

1141   CGGACGTACG TGTGCAAGTC GTCGCAACTT GCGTGCTACA GAAATTCAAA ACAAAACAAA

1201   AAACTTGCG TGGCACAGTA CGAGACTACA AGCGAGTAGA AGCGCACCAC GTATGCCCGT

1261   GTATCTGCAG TAACGGAACC GTGCACGTTT TGGCTAAACG TGCGCATGCA GCAGGGTGCA

1321   CGTCCACGTC CTGCAGGTTT AAGTATATAA TGTAGCTTAC AGTAATTAAC CATGCATGCT

1381   TCGAAATGAA GCACTGCCTG CCGGGCGCCG GCGACCTGAT CCACCACCAC CCGACGCGCG

1441   GCTCGCCGGC GGGAACAGCC AGTCGCGCGC GTGGACCTCT CGCCTCTACC AACGTGTGGC
```

-continued

```
1501 TACGTGTAAC CGTGCTCCGT AAAACCGTGT TGGTTTTACC TTTACCTTTC TCTCGCCCGC
1561 ACACACGTCG CCGCCAAGAC ATGCGTCGCG TCATTTTCTC CAAATAACTT TGGCGCGAAC
1621 GGGTCTCCGA TCGAGCAGCA CCAAATCAAT CAACCCAACG AAAGTGATCC GACGTCACAA
1681 AATTCGATCC CCCGAGAAAC TGGCAGCACT TTTGCCGTTT TCTTGCCGGT CCCAACGAAC
1741 TCTCCGTCCC TCCTAATTTA ATGTCAAAAA AATATAAAAA AATCTCCGCC TGCGTTGATG
1801 ATCCCAATAA CCAGCAAGCT GTCCTACGGG ATCATTCAGG AGCTTTTAGA GCTGCTACTT
1861 GTCATCTCTT TGATGGAATC GCCGATTCGG AGGTTGCTGA AATTTATGCC TGCAAACGAG
1921 CTTTATAGGT GGCGGCCGAA CTCAACACAT CCAAGCTGTT GTTGGAGACG GACTGTGCTA
1981 ATCTAGCAAA GATGTTGTGT GCGCAAGAGA AAACTCTCTC TGCATTTGGA CCTCTGGTGA
2041 AGGAGATCAA GGAGAGGATG AAAATGTTCC AAGAAGTGAA AATGTCTTGC GTAAGGCGTA
2101 GTGCTAATGC TGCCGCGGAT AAGTTAGCTA AGTTGGGTT AAGTGATAGA CTGTGTAAGG
2161 TTTGGTTTGC CGTTCCCCCA GATTGTATTC TGGGCATTGT GTCGGACGAG ATTCCTAATT
2221 TCATTTAATT AGTCAATAAA GCGGCAGTAG TTGATCCTCA AAAAAAATAA CCAGCAAGCT
2281 AGCCGGACGC GTCGGTTTTT GTCCTGCCTA AGCTAGGAGT ATCTCCAAGT AACCTACGCG
2341 GGACAAAACT ATGGCCAGAT AGACACTAGT CAAACGATCG CAACAAGAAA AAAACTAGTC
2401 AAGAAAAATA CTACAGATTA CCTAAAGAAA AAAATAGAA AACCAAAACA AAAATACTGG
2461 TAAAGTGACC GTCCCCGTCA AAAATACTT GCCGACCGAC CGGGTGTCCC CCGTCGCCCC
2521 GGCCCGGTGC CGGCCGAGCA CCCCGCCCAG AGCGCCATCA CTGGATCAAC CACCCCGTCC
2581 AACCGCGCGC TACGAAACAT CGGTCGTTTC TCACGGTGCA ATCTCAGCCG GAAACCGGCG
2641 CTCGCGCGCA TCAGCTGTAG CCTGTAGGTC TCGGGCTCCG CAGCGCCGCT GCCGAGCCAC
2701 CCGGCCGGCG CGCACGCACG CACGCGCTTT GACCCGGCCG CCGATAAAAG GCCCCGCGCG
2761 GCAGCTCCCT CCTACCCGGT TGCCACACCC ACAGTCTGCC ACAGCAGCAA CAAGCTAGAC
2821 ATACCTGCGT GCGTACGTAC GTTTTCGTTT TCCTTTCTTG CTCCGGCCGG CCGGCCGGCC
2881 ACGTAGAATA GATACCTGCC CAGGTACGTA CCTCGTTGGC TCAGACGATC GGCGGTTGGA
2941 CTTGGGTGCG CGCCCTGCCC TGCTCCGGCC AAGGAAAGAG GTTGCGCTAA AGACGGGCGG
3001 ATG
```

Tamlo-R32-B upstream sequence (~3500 bp); ATG start codon in bold and underlined SEQ ID NO. 41

```
  1 CCCCGTAGCT CTTTTATTTC GCGAGGGCTT TGATCATGTA TAGCTAGCCA TAAACAACAT
 61 GACAGGCATG TTTTGGGTGC CCACAGCACA CACAAGTTGT GAAACAGTAC GTACATGACT
121 GGGCACAGAG CAGGTTAGAG GAAACCTCCA CATCATCATA AATTCTGAGG AGCCACTAGA
181 TTCAGCATGT CTGTTTAGGG TTCTGGCTAC TTGCCAATAA AAAAATATTA TGATTTACTA
241 GCATAGATTC CAGAATGCCA TGACATTTCT GCTTTGATTT CAATCCACTG CTCATAACAG
301 AAGCATATGG CCCGGACTCA TTAACTTGGT CGTTCCTCAT GATTTGTTCT AGTCTCGTTT
361 TATCTCACAA GATGCTTGTT CACAAGGTTG TCAGAATCGC GATTCTGAAT CGGATCGGAG
421 CTCCAATGGC AGGATCACAA ATCATAGAAT CTTCACTATC AGGATCGTGA AAACGTAGAT
481 TCTATGAACC AAAATCATAA AATCAGAGGG GTTAGTTTGA ATCGTAAAAT CGTAGAATCG
541 TACAACATAA TCGCGATTCT GACAACCTTG CTTGTTCATT TGCTGCTATA TATATTAGGA
601 CCATGCATAT TGGTCACACG AGGGCAGCGC TGCAAGTGCA AGTCGCCGA GACAAGACTG
661 AGCACCGTTT CATGGGCTTG ATCTCTTGGT AAGCAGCCGC CGCCGGACCA TCATCAGCCA
```

-continued

```
 721   AGAAAGACAC ATTCTTGTGC TACTATATTT GTGCGGTTGC GCGCATGAGA TAAGATCCGG
 781   ATGAGGATGG CGCGCATAAA AAAATGAGCA ATGTCAAAGC AGTGTACCCT GAGCTTCCTT
 841   CCATTCATGA ACCAGTAGCG TCAACTACAG GAACGAGCAA CGAACCGTCA CCTTATATTA
 901   GTGGATCGGG CCCATCCATC CCATCAGGGT GTGCCGTCAA GCAGATCTCC ATGCATGCAT
 961   CTCGGATTGC ACCTAGTAGC CACATAAACA GAGGCTGATT AGTACTACTA CAAAGGTACC
1021   GGCTAGGCCA AATCATCTCG CCTCGTTGAA ATTCAAACCT GCCATTAACT TTCCCCGATC
1081   AGAAGAAACG GTCCGGATCC GATCGTTAAT TCGGCGACCA GTGACTTGAT CTCGTCCGTT
1141   TAAGCACTAT ACTAGCAGCA GATCACTGAT CACATGGATG GACCGCTGCT AAGAATAGTA
1201   TATCCTTCCT GCATATACAA GTCCGCAAAA AGTAGCAGC CACACAAATG CAGTCAACGC
1261   TCCATTTGAC TTGACCCGCT CCATCAGGCC CGTACTCCAC TGGTTGAAAC GCCCACTTCG
1321   CCGGAGCGGC GTGGTCGACT TCTCCACGCA GGGGACCGAC CATGAGCAGT CAAACTTGGG
1381   ATGCCACGTC GACCGACGTG TGCAAGTCGT CGCAACTTGC TTGGCACAGT ACGAGACCAC
1441   AAGCGAGCAG GAGTGCGCCA CGTATACGTG ACGGGCCCGT TTGCCTGCAG TGACGGAACC
1501   GTGCACGCTT TGGCTAAATA TAAACGTGCG CATGCAGCAG GGCTTACAAG AACCATTAAG
1561   TAACTTTCAC GTCCACGTCG TACAGTACAT GTTTATATAT AACGTCGTAA ACTACAGTTA
1621   GCGCATGCTC TAGCGGCATA CGGTGCCAGC CGACTGATGG TCCGGCAAGT TTGGGCTGAT
1681   GACCTACCTG ATGATGTAAA CGTTCAGATG GCCAGCGTTT TGCCTGCGCC CGTGTGATTT
1741   ATGGAATCTG GGTGTTCCAT TTAAAAAAAA AAACCCATTC ATGCTTCGAA ATGAAGCATG
1801   GAGGAAGTCG GACGTCACAC AATTCGATCG ATCGACCCAT CGTTTTTCTC GGCCGGGGAA
1861   GAGGCAAGGC GGGCACAGTT TTGCCCTTTT CGATCGTTTG GTCCGTCCCA ACAGATTCTC
1921   CGTCCCCATT AATCAAGTCC AAAACAGGAA TACATGCAGC AATACTCTAT GCTTGTCCAA
1981   TTAGCAATTA CTCTCACGTC AACCGCTGGC GATTAACAAT GGCTCTCCGT ATGAAAAACT
2041   AACTCGATGG GAGCACCAGG CTAGCCATCG TGCACGCACG TCCCGGCCGG TGAATGTTTC
2101   GACCGTCTGG GTACGAGCCC GACCCGCTCG AAGGTGCCAC GCCCCTGCCT ACCAGGCGCC
2161   GGCGACCTGA TCCACCACCC GACGCGCGGC TCGCCGGCGG GAACAGTCAG TCGCGTTGAC
2221   CTCTCGCCTC TACCAACGTG TGGCTACGTG TAACCGTGGT CCGTAAACCC GTGTTCGTTT
2281   TACCTTACCT TTCTCACGCA CACAATACAT GTTTCGCGTC ATTTTCTCCA CGTAAAACTT
2341   TGGCGCGAAC GGGTCTCCGA TCGAGCAGCA TCAAATCAAT CAACCCAACG AAAGTGATCC
2401   GACGTCACAC AATTCGATTC CCCAAGAAAC GGGGCAGCAC ATTTGCCGTT TCCTTGCCGG
2461   TCCAACGAAC TCTCCGTCCT AATTTAACGT CAGTTTTTTT TCTCCGCCCG CGTTGATGAT
2521   CCCGATAACC AGCAAGCTAG CCAGACGCGT CGGCTTTTGT CCTGCTTAGC TAGGAGTATC
2581   TCCAAGTAAC CTTACCTACG CGGGACAAAA CTATGGCCAG ATATAGATAT ACTAGTCAAA
2641   CGATGGCAAC AAGAACAAAA AAAAACTACT CCCTCCGCTT CTAAATATAA GTTTTCTAG
2701   AGATTTTACT ATAAACTATA TACGGACGTA TATAGACAAA ATTTAAGTGT ATATTCACTT
2761   ATTTTGCTCT GTATGTAGTT TTTTGTTGGA ATCTCTAAAA AGAAATATAG GAGTATTTAG
2821   GAACAGAGGG AGTAGTCAAG AATAATACTA CGGATTCCCT AAAGGAAAAA ATAGAAAAAA
2881   AATACTACTA GTATTTTTTG AGAAATAATA CTACAAGTAA AGTGACCGTC TCTGTCAGAA
2941   AATACTACGG GACCGACCGG GTGTTCCCCC TCGCCCCGGC CCGGTGCCGG CCGAGCACCC
3001   AGAGTGCCAT CACTGGATCA ACCACCCCGT CCAACCTCGC GCTAGGAAAC ATAGCTCGAT
3061   CCCTCAAACA AAAAAAAAAA GGAAACATAG CTCGTATCAG CCGAAACCCG CCACTCGACA
```

-continued

```
3121  TTCGTATCAG CTCTAGGCAG GTCTCCCGCT CCGCAGCGCG CCGCTGCCGA GCCACCCGGC

3181  CGGCGCGCAG GCGCGCACGC ACGCGGTTTG ACCCGGCCGC CGCGCGCCCG CGCCGCGCCG

3241  ATAAAAGGCC CCGCGCGGCA GCTCCCTCCC ACCCGGTTGC CACGCCCACA CTTCGCCAAC

3301  ACACAACGTA CCTGCGTACG TACGCTTTCC ATTTCCTTTC TTGCTCCGGC CGGCCGGCCA

3361  CGTAGAATAG ATACCCGGCC AGGTAGGTAC CTCGTTGGCT CAGACGACCG GCGGCTGGGT

3421  CTCCGGACAA GGAAAGAGGT TGCGCTCGGG GACCGATG
```

Tamlo-R32-D upstream sequence (~3500 bp); ATG start codon in bold and underlined SEQ ID NO. 42

```
   1  GAGGGAAATG TTTTAGAACT GGGCGAGGGC CCGGACTCAT TAACTTGGCT GTTCCTCATG

61  ATCTGTTCTT GTCTCGTTTT ATCTCAGGAG ATGCTTGTTC ATTTGTTGCT ATATAATACT

121  TCCTCCGTTC GGAATTACTT GTCGCAGAAA TGGATGTATC TAGACATATT TTAATTTTAG

181  ATACATTCAT TTTCGAGACA AGTAATTCCG AATGGAGGGA GTACCCATGC ATATTCGTCT

241  CACGAGGGCA GCGCTGCAAA TGCAAAGTCT CGCCGAGACA AGACCGGTCA CCCTTTTCAT

301  GAGCTTGATC TCTTGGTAAG CAGCCCCCGC CGGACCATCA TAATAACTTC ATAAGCCGGG

361  AAAGACCCAT TTGTGGTACG TACTAATACT ATATTTGTGC GGTTGTGCGC ATGAGATAAG

421  ATCCGGTTGA GGGTGGCGCG CATAAAAAAT GGGCTATGTC AAAGCAATAT CCCCTGAGCC

481  TCCATCCATG AACCAGTAGC GTCCGTCAAC TACACGAACG AGCGACGAGG CCGCGCGCTA

541  CGAGCGCCAC CATATACGTA CGTATATATT AGTGGATCGG GCCATTAGCA TAAGATCTCC

601  ATGCATGCAT GTCGGATAGT ACATCTCGAA ATAGTCTTTC GCCCCGCTTT ATCTCGGATG

661  CACCTAGTAG CCACATAGAC AGGCCAAATC ATCGCTTGCT AAAAGAACTG AGCTAGTAGT

721  AGTACTGGCA TCTCTTGATG TGCCTCGTTG AAATTCAAAC CGACCATTAA CTTTCCCCGA

781  TCAGAGGAAC CGGTCCGGAT CCGATCGTTA GTTCGGCGAC GGGCGACTTG ATCCCGTCTG

841  TTTAAGCACT AGTAGTAGCA GATCACTCAT CACATGGACG GACCGCTGCT AATAATTAAT

901  AGTATACCTG CCTGCTGTGC ATATACAAGT CCTGGTAAAA GTAGCAGCCA CACAAATGCA

961  GTCAACGCTT CGTTTGACTT GACTCGCTCA GGCCCGTAGC CGTACTCCAC TGGATCTGGA

1021  TGGAACGCCC GCTTCGCCGG AGCTGCCTGG TCAGACTTCT CCACGCACGC ACGACCGACC

1081  ATGGGCAGTC AAACTTCGGA TGCCACGTCG ACGTCCACGT TGTCGGTCGC ATGCGGACGT

1141  GCGTGTGCAG GTCGTCGGAA CTTGCGTGGT ACAGTACGAG ACTACTCCGT ACAAGCGAGT

1201  AGAAGTGCAC CACGTATACG TGCCGGGCCC GTTTACCTGC AGTAACGGAA CCGTGCACGC

1261  TTTGGCTATA CGTGCGCATG CAGCAGGCTG CACGTCGATG CCGTGCAGGT TTTATAATGT

1321  AGGAGTATAC TGTAACTACC TTACAATTAA TAACCATGGA TGGATGCTTC GAAATGAAGC

1381  ATGGAGGAAG CCCGACGTCA CACAGTTCGA TCGCCCGATC CCTCGTTTTT CCCGGCCGGG

1441  GAAGAGACAA GAGAAACAGA GCTTTGCCCT TTTCGATCGT CTGGTCTGTC CAACAGACT

1501  CTCCGTCCTC ATTAATCAAG TCCAAAACAG GAATACATGC AGCAATACTG TATGCTTGCC

1561  AAATTAGCAA TCACTATCAC GTCAACCGGG GGCGATTAAC AATGGCCCCT CCGTATGAAA

1621  AACTAACTCG ATGGGAGCAC CAGGCTAGCC ATCGTACACG CACGTCCCGG CCGGTGAATG

1681  TTTCGACCGT CTGGGTACGA GTCTGACCCG CTCGAAGGTG CCACGCCCCT GCCTGCCGGG

1741  CGCCGGCGAC CTGATCCACC ACCACCCGAC GCGCGGCTCG CCAGCGGGAA CAGTCAGTCG

1801  CGCGCGTGGA CGGCGAGTCT CGCCTCTACC AACGTGTGGC TACGTGTAAC CGTGCTCCGT

1861  AAAACCGTGT TCGTTTTACC TTACCTTTCT CGCGCGCACA CACGTCGCCG CCAATACATG
```

-continued

```
1921  TTTCGCGTCA TTTTCTCCAC GCAATAACTT TGGCGCGAAC GGGTCTCCGA TCGAGCGGCA
1981  TCAAATCAAT CAACCCAACA AAAGTGATCC GACGTCACAC AATTCGATCC CCCAAGAAAC
2041  GGGGCAGCAC ATTTGCCGTT TTCTTGCCGG TCCCAACGAA CTCTCCGTCC TAATTTAACG
2101  TCAGTTTTTT TTCTCCGCCC GCGTTGATGA TCCCGATAAC GAGCAAGCTA GCCAGACGCG
2161  TCGGTTTTTG TCCTGCCTAG CTAGGAGTAT CTCCAAGTAA CCTACCTACG CGGGACAAAA
2221  CTATGGCCAG ATATAGATAT ACTAGTCAAA CGATGGCAAC AAGAAAAAAA ACTAGTCAAG
2281  AATAATACTC CCTCCATTCT AAATTACTTG TCGCAGGTAT GAATGTATCT AGATGTATTT
2341  TAGTTCTAGA TACATCCATT TCTGCAACGA GTAATTTGAA ACGGAGGGAG TACTACGGAT
2401  TCCCTAAAGA AAAAAATACT ACTAAAAACT AGTACTAGTA GTAAAGTGAC CGTCCCCATC
2461  AAGAAATACT ACGGGACCGA CCGGGTGTCC CCCTCGCCC CGGCCCGGTG CCGGCCGAGC
2521  ACCCAGAGCG CCATCGCTGG ATCAACCACC CCGTCCAACC TCGCGCTAGG AAACATAGGT
2581  CGTTTCAGCC GAAACCCGCC ACTCGACATT CGTATCAGCT CTAGGCAGGT CTCCCGCTCC
2641  GCAGCGCCGC TGCCGAGCCA CCCGGCCGGC GCGCAGGCCT AGGTTTGACC CGGCCGCCGG
2701  GCGCCCGGCC GATAAAAGGC CCCGCGCGGC AGCTCCCTCC CACCCGGTTG CCACGCACAC
2761  ACTTCGCCAC AGCAGAAACA AGCTAGACAC ACAACGTACC TGCGTACGTA CGCTTTCCTT
2821  CTCCTTGCTT GCTCCGGCCG GCCGGCCACG TAGAATAGAT ACCTGGCCAG GTAGGTACCT
2881  CGTTGGCTCA GACGATCGGT GGTTGGGCTC GGGCGCGCGC CTGTCCGGCT GAGGTGGCCG
2941  CCGTTCGCTC CGGCCAAGGA AGAGGTTGT GCTCAGGACG GCGGCGGGG AGCCATG
```

The invention claimed is:

1. A wheat plant having increased resistance to powdery mildew compared to a wild type wheat plant and comparable yield under non-disease conditions compared to a wild type wheat plant, wherein said plant comprises
   a first targeted knock-out mutation which is an insertion and/or a deletion in SEQ ID NO. 43 of TaMLO-A1 allele,
   a second targeted knock-out mutation which is an insertion and/or a deletion in SEQ ID No. 45 of TaMLO-D1 allele, and
   TaMLO-B1 allele does not contain mutations in SEQ ID NO. 44, but expression of the TaMLO-B1 allele is reduced by 5 to 50% compared to wild type expression, wherein said reduced expression of TaMLO-B1 is caused by a mutation in the regulatory region of SEQ ID NO: 41, and
   wherein said wheat plant is Triticum aestivum.

2. The wheat plant according to claim 1, wherein the first targeted knock-out mutation and the second targeted knock-out mutation are introduced using targeted genome modification by using a Transcription Activator Like Effector Nuclease (TALEN), Zinc Finger Nuclease (ZFN) or Clustered Regularly Interspaced Short Palindromic Repeat/Cas9 (CRISPR/Cas9).

3. The wheat plant according to claim 2, wherein said first mutation in the TaMLO-A1 allele and/or said second mutation in the TaMLO-D1 allele is introduced using a TALEN and wherein said TALEN binds to TCGCTGCTGCTCGCCGTgacgcaggacccatctcCGGGA-TATGCATCTCCGA (SEQ ID NO. 13).

4. The wheat plant according to claim 1, wherein said plant does not comprise a transgene.

5. The wheat plant according to claim 1 comprising a-the mutated TaMLO-A1 sequence as shown in SEQ ID No. 38, and the mutated TaMLO-D1 sequence as shown in SEQ ID No. 39.

6. A wheat plant, wherein representative seeds of said wheat plant have been deposited under CGMCC Accession Number 10951 or a plant cell of said wheat plant.

7. A method for producing the wheat plant of claim 1, wherein the method comprises introducing the first knock out mutation by targeted genome modification, introducing the second knock out mutation by targeted genome modification and introducing a mutation in the regulatory region of the TaMLO-B1 allele.

8. The method according to claim 7 wherein the first knock out mutation and the second knock out mutation are introduced by TALEN, ZFN or CRISPR/Cas9.

9. The method according to claim 7, further comprising screening for a plant resistant to powdery mildew.

10. The method according to claim 7 wherein the wheat plant does not contain a transgene.

11. The wheat plant of claim 1, wherein the wheat plant being obtained by a method comprising introducing the first knock out mutation by targeted genome modification, introducing the second knock out mutation by targeted genome modification and introducing the mutation in the regulatory region of TaMLO-B1 allele.

12. A plant part or plant cell of the wheat plant of claim 1 and comprising:
   a first targeted knock-out mutation which is an insertion and/or a deletion in SEQ ID NO. 43 of TaMLO-A1 allele,
   a second targeted knock-out mutation which is an insertion and/or a deletion in SEQ ID No. 45 of TaMLO-D1 allele, and
   TaMLO-B1 allele does not contain mutations in SEQ ID NO. 44, but expression of the TaMLO-B1 allele is reduced by 5 to 50% compared to wild type expression, wherein said reduced expression of TaMLO-B1 is caused by a mutation in the regulatory region of SEQ ID NO: 41; and
   wherein the plant part or plant cell having grown into the wheat plant of claim 1 has increased resistance to powdery mildew compared to a wild type wheat plant and comparable yield under non-disease conditions compared to a wild type wheat plant.

\* \* \* \* \*

UNITED STATES PATENT AND TRADEMARK OFFICE
CERTIFICATE OF CORRECTION

PATENT NO. : 10,988,775 B2
APPLICATION NO. : 15/745479
DATED : April 27, 2021
INVENTOR(S) : Caixia Gao Page 1 of 1

It is certified that error appears in the above-identified patent and that said Letters Patent is hereby corrected as shown below:

In the Claims

Column 115, Claim 5, Line 1, delete "a-the" and insert --the--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*